United States Patent
Gilbert et al.

(10) Patent No.: US 9,320,773 B2
(45) Date of Patent: Apr. 26, 2016

(54) COMPOUNDS AND THERAPEUTIC APPLICATIONS RELATED TO INHIBITION OF DENDRITIC CELL IMMUNORECEPTOR (DCIR) ACTIVITY AND SIGNALING EVENTS

(75) Inventors: Caroline Gilbert, St-Augustin de Desmaures (CA); Alexandra Lambert, Québec (CA); Michel J. Tremblay, Québec (CA)

(73) Assignee: Université Laval, Québec (CA)

( * ) Notice: Subject to any disclaimer, the term of this patent is extended or adjusted under 35 U.S.C. 154(b) by 19 days.

(21) Appl. No.: 13/817,393

(22) PCT Filed: Aug. 4, 2011

(86) PCT No.: PCT/CA2011/000888
§ 371 (c)(1),
(2), (4) Date: Jun. 25, 2013

(87) PCT Pub. No.: WO2012/021964
PCT Pub. Date: Feb. 23, 2012

(65) Prior Publication Data
US 2013/0267461 A1      Oct. 10, 2013

Related U.S. Application Data

(60) Provisional application No. 61/374,742, filed on Aug. 18, 2010.

(51) Int. Cl.
| | |
|---|---|
| *A61K 38/10* | (2006.01) |
| *A61K 38/08* | (2006.01) |
| *A61K 31/7088* | (2006.01) |
| *C07K 14/705* | (2006.01) |
| *C12N 15/113* | (2010.01) |
| *G01N 33/50* | (2006.01) |
| *G01N 33/569* | (2006.01) |
| *A61K 38/00* | (2006.01) |

(52) U.S. Cl.
CPC ............. *A61K 38/10* (2013.01); *A61K 31/7088* (2013.01); *A61K 38/08* (2013.01); *C07K 14/705* (2013.01); *C12N 15/1137* (2013.01); *C12Y 301/03048* (2013.01); *G01N 33/5047* (2013.01); *G01N 33/56988* (2013.01); *A61K 38/00* (2013.01); *C12N 2310/11* (2013.01); *G01N 2333/16* (2013.01)

(58) Field of Classification Search
None
See application file for complete search history.

(56) References Cited

U.S. PATENT DOCUMENTS

| | | | |
|---|---|---|---|
| 7,030,228 B1 * | 4/2006 | Schmitz et al. ............ | 530/389.6 |
| 2004/0171695 A1 | 9/2004 | Tracey et al. | |
| 2007/0087982 A1 | 4/2007 | Nelson et al. | |
| 2010/0061991 A1 | 3/2010 | Lambert et al. | |
| 2012/0039894 A1 | 2/2012 | Lambert et al. | |

FOREIGN PATENT DOCUMENTS

EP            1350510 A1     10/2003

OTHER PUBLICATIONS

Lambert et al, Blood (Aug. 15, 2008) 112(4): 1299-1307.*
Lambert (Blood (Aug. 15, 2008) 112(4): 1299-1307).*
Gengiah (Int J Clin Pharm (2014) 36: 70-85).*
Gilbert et al., "Involvement of Src and Syk Tyrosine Kinases in HIV-1 Transfer from Dendritic Cells to CD4+T Lymphocytes," *J. Immunol.* 178: 2862-2871 (2007).
Lambert et al., "DCIR-mediated enhancement of HIV-1 infection requires the ITIM-associated signal transduction pathway," *Blood* 117(24): 6589-6599 (2011).
International Preliminary Report on Patentability for PCT/CA2011/000888, issued Feb. 19, 2013 (10 pages).
International Search Report for PCT/CA2011/000888, mailed Nov. 22, 2011 (7 pages).
U.S. Appl. No. 13/280,070, filed Oct. 24, 2011 (corresponding to US 2012/0039894 A1, published Feb. 16, 2012).
Weissman et al., "Role of dendritic cells in immunopathogenesis of human immunodeficiency virus infection," Clin Microbiol Rev. 10(2):358-67 (1997).

* cited by examiner

*Primary Examiner* — Marcela M Cordero Garcia
*Assistant Examiner* — Mindy Newman
(74) *Attorney, Agent, or Firm* — Clark & Elbing LLP; Susan M. Michaud

(57) ABSTRACT

The invention is concerned with methods, compounds and pharmaceutical compositions for interfering dendritic cell immunoreceptor (DCIR) activity and signalling events. Described herein are compounds useful in targeting one or more of intracellular modulators and the uses thereof for the prevention or treatment of virus infections, and more particularly for reducing human immunodeficiency virus (HIV) binding, entry and/or replication in human cells. Exemplary compounds include peptides and antisense molecules.

17 Claims, 16 Drawing Sheets

Figure 1
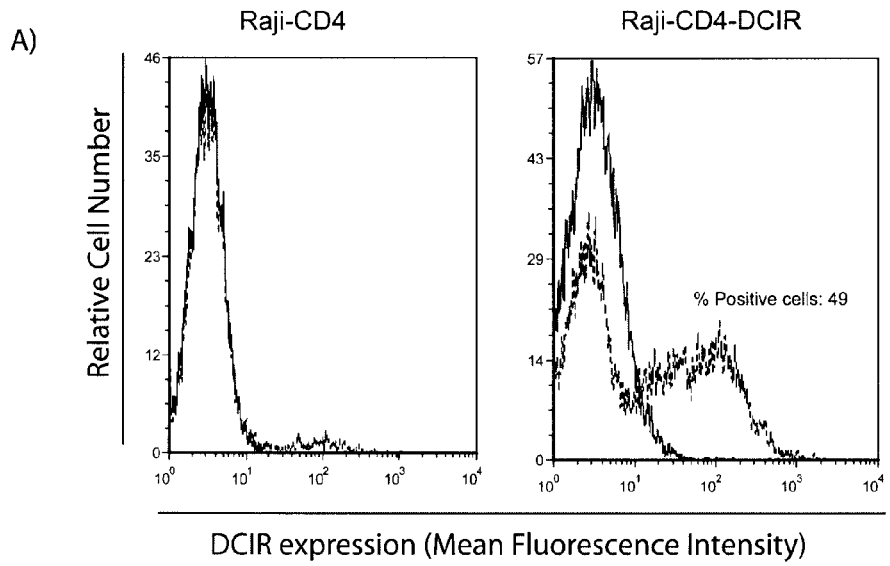
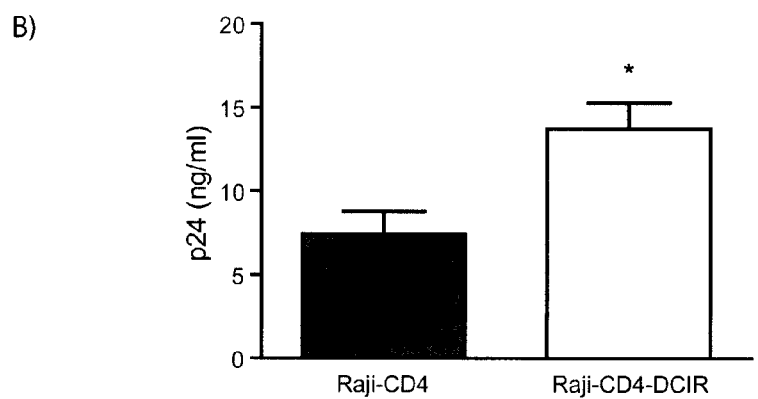
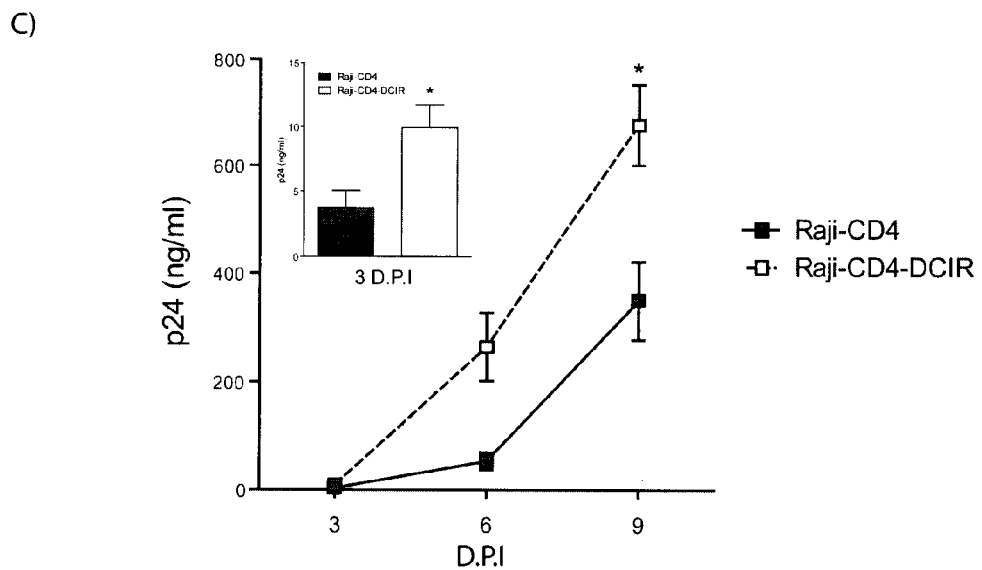

FIGURE 3
3A) Src family tyrosine kinase inhibitor: PP2
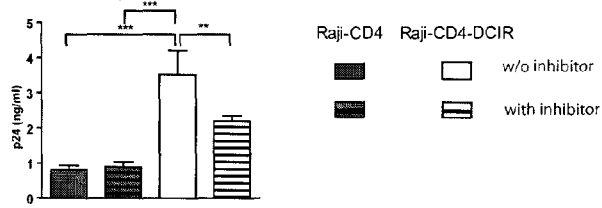
3B)
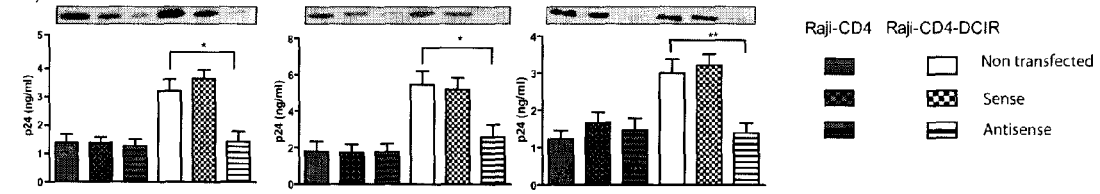
3C) BTK inhibitor: LFM-A13
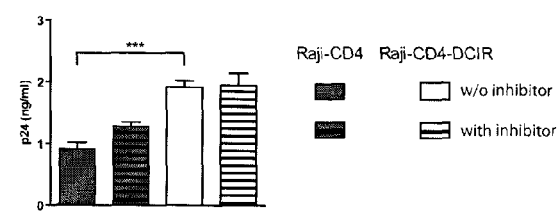
3D) Syk kinase inhibitor: Piceatannol
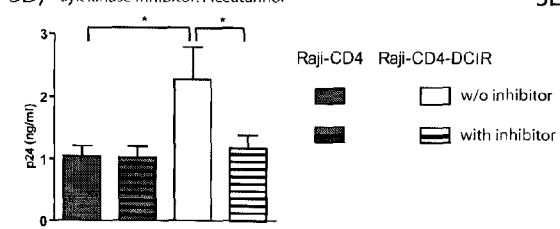
3E)
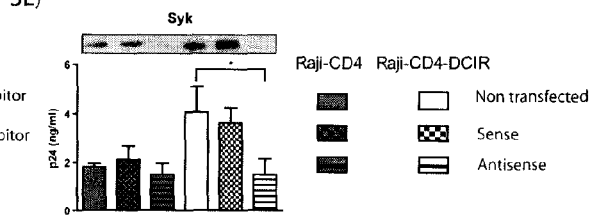
3F) PI-3 kinase inhibitor: Wortmannin

Figure 6
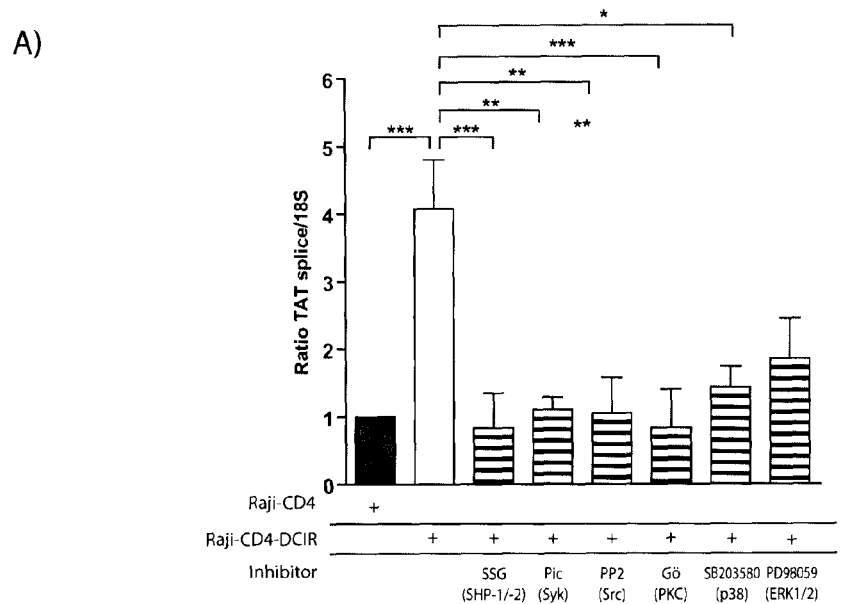
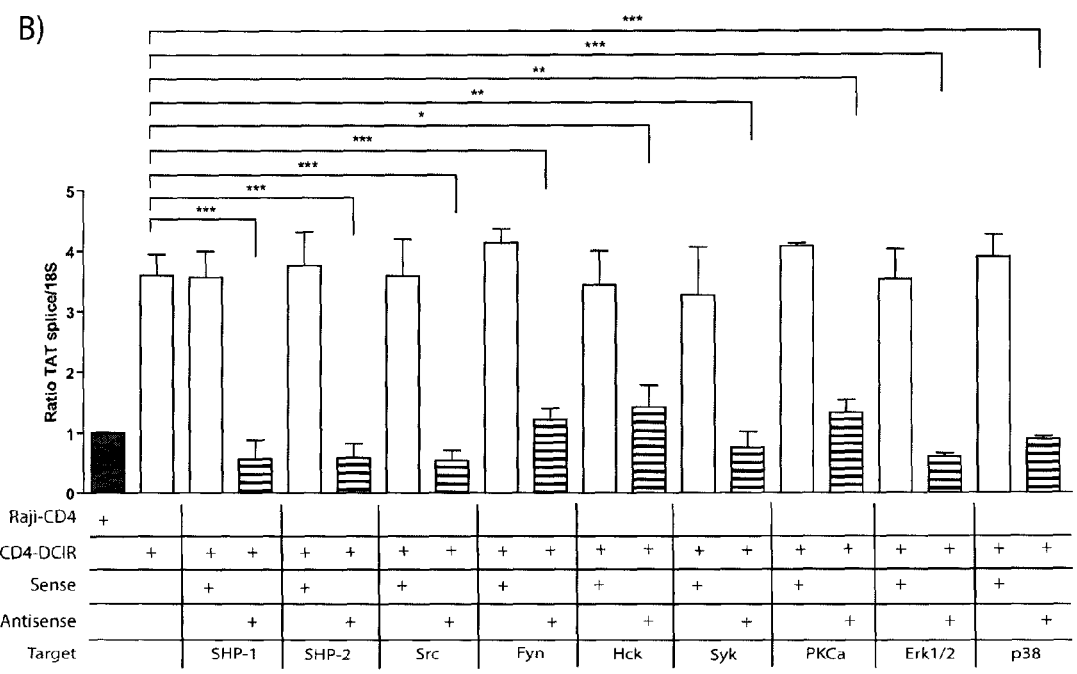

Figure 7
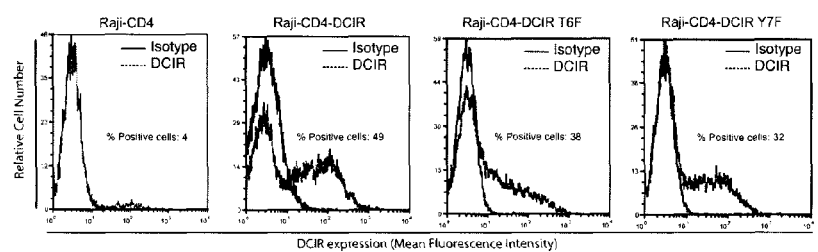
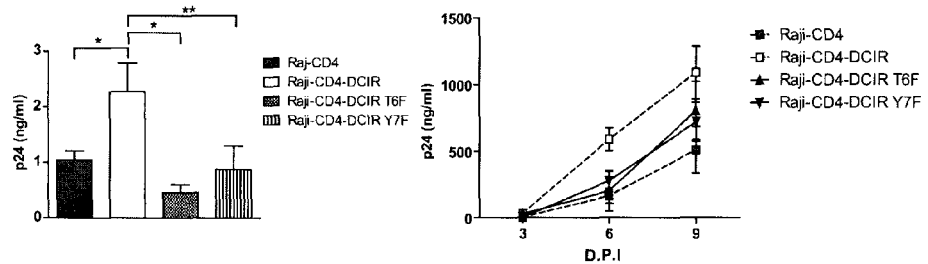
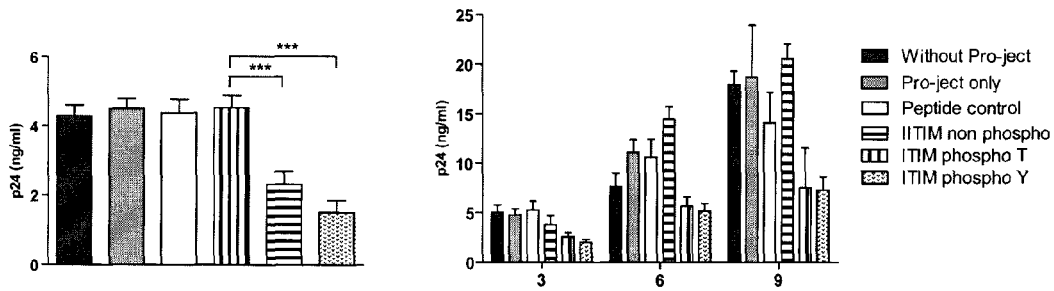

Figure 8

Isoform 1 (SEQ ID NO : 1)

```
mtseityaev rfknefkssg intassaask ertaphksnt gfpkllcasl lifflllais
    ITIM motif                                        Transmembrane domain
ffiafviffq kysqllekkt tkelvhttle cvkknmpvee tawsccpknw ksfssncyfi
           Neck domain                                     CDR domain
stesaswqds ekdcarmeah llvintqeeq dfifqnlqee sayfvglsdp egqrhwqwvd
qtpynesstf whpreqidpn ercvvlnfrk spkrwgwndv nclgpqrsvc emmkihl
            Blocking antibody                    Blocking antibody
              EPS motif
```

Isoform 2 (SEQ ID NO : 60)

```
mtseityaev rfknefkssg intassaask ertaphksnt gfpkllcasl lifflllais
    ITIM motif                                        Transmembrane domain
ffiafvktaw sccpknwksf ssncyfiste saswqdsekd carmeahllv intqeeqdfi
                       CDR domain
fqnlqeesay fvglsdpegq rhwqwvdqtp ynesstfwhp reqidpnerc vvlnfrkspk
                                              Blocking antibody
rwgwndvncl gpqrsvcemm kihl                      EPS motif
         Blocking antibody
```

Isoform 3 (SEQ ID NO : 61)

```
mtseityaev rfknefkssg intassavff qkysqllekk ttkelvhttl ecvkknmpve
    ITIM motif                                      Neck domain
etawsccpkn wksfssncyf istesaswqd sekdcarmea hllvintqee qdfifqnlqe
                     CDR domain
esayfvglsd pegqrhwqwv dqtpynesst fwhpreqidp nercvvlnfr kspkrwgwnd
                                            Blocking antibody
vnclgpqrsv cemmkihl                            EPS motif
         Blocking antibody
```

Isoform 4 (SEQ ID NO : 62)

```
mtseityaev rfknefkssg intassaeta wsccpknwks fssncyfist esaswqdsek
    ITIM motif                                CDR domain
dcarmeahll vintqeeqdf ifqnlqeesa yfvglsdpeg qrhwqwvdqt pynesstfwh
preqidpner cvvlnfrksp krwgwndvnc lgpqrsvcem mkihl
Blocking antibody                   Blocking antibody
EPS motif
```

Figure 9
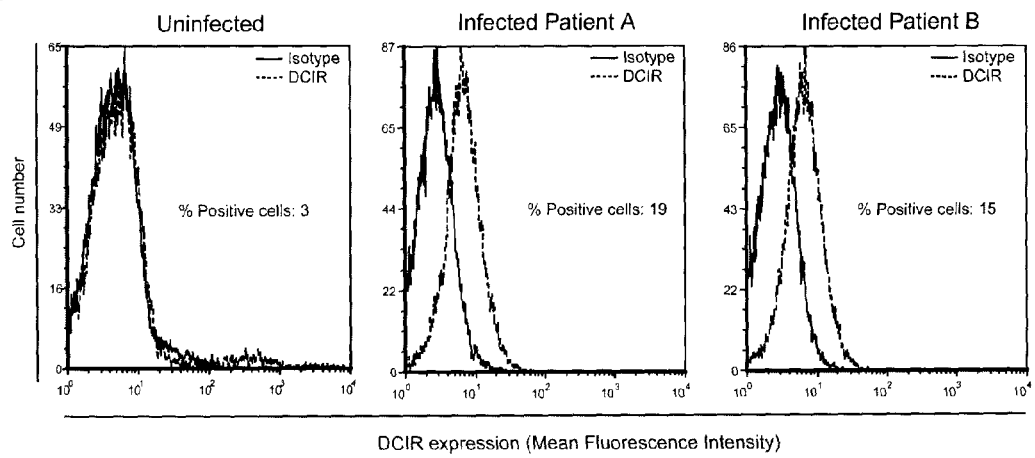
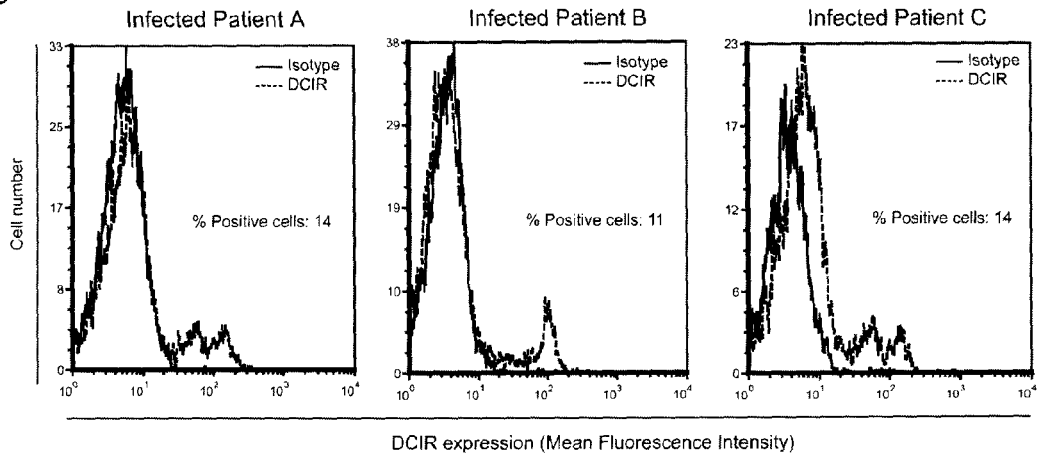
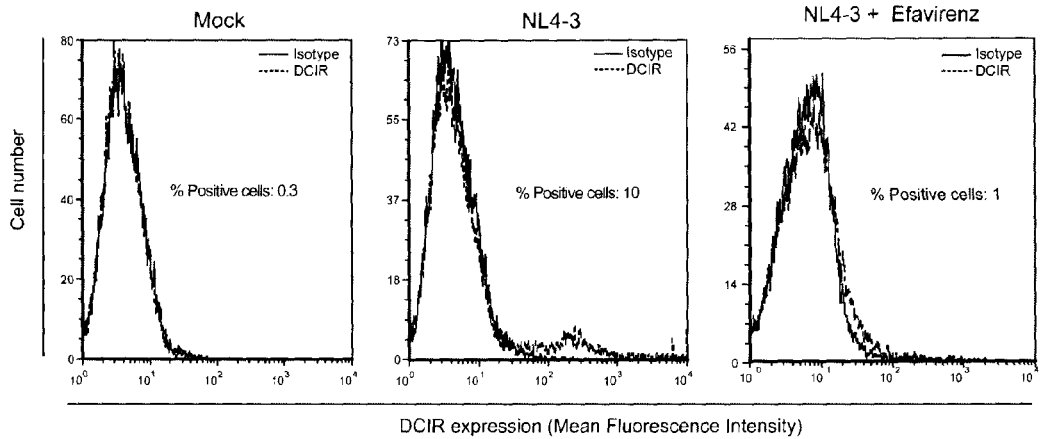

SEQUENCE LISTING

<160> NUMBER OF SEQ ID NOS: 62

<210> SEQ ID NO 1

```
<211> LENGTH: 237
<212> TYPE: PRT
<213> ORGANISM: Homo sapiens

<400> SEQUENCE: 1

Met Thr Ser Glu Ile Thr Tyr Ala Glu Val Arg Phe Lys Asn Glu Phe
1               5                   10                  15

Lys Ser Ser Gly Ile Asn Thr Ala Ser Ser Ala Ser Lys Glu Arg
            20                  25                  30

Thr Ala Pro His Lys Ser Asn Thr Gly Phe Pro Lys Leu Leu Cys Ala
            35                  40                  45

Ser Leu Leu Ile Phe Phe Leu Leu Ala Ile Ser Phe Phe Ile Ala
    50                  55                  60

Phe Val Ile Phe Phe Gln Lys Tyr Ser Gln Leu Leu Glu Lys Lys Thr
65                  70                  75                  80

Thr Lys Glu Leu Val His Thr Thr Leu Glu Cys Val Lys Lys Asn Met
                85                  90                  95

Pro Val Glu Glu Thr Ala Trp Ser Cys Cys Pro Lys Asn Trp Lys Ser
                100                 105                 110

Phe Ser Ser Asn Cys Tyr Phe Ile Ser Thr Glu Ser Ala Ser Trp Gln
            115                 120                 125

Asp Ser Glu Lys Asp Cys Ala Arg Met Glu Ala His Leu Leu Val Ile
    130                 135                 140

Asn Thr Gln Glu Glu Gln Asp Phe Ile Phe Gln Asn Leu Gln Glu Glu
145                 150                 155                 160

Ser Ala Tyr Phe Val Gly Leu Ser Asp Pro Glu Gly Gln Arg His Trp
                165                 170                 175

Gln Trp Val Asp Gln Thr Pro Tyr Asn Glu Ser Ser Thr Phe Trp His
            180                 185                 190

Pro Arg Glu Pro Ser Asp Pro Asn Glu Arg Cys Val Val Leu Asn Phe
        195                 200                 205

Arg Lys Ser Pro Lys Arg Trp Gly Trp Asn Asp Val Asn Cys Leu Gly
    210                 215                 220

Pro Gln Arg Ser Val Cys Glu Met Met Lys Ile His Leu
225                 230                 235

<210> SEQ ID NO 2
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is S, I, V or L
<220> FEATURE:
<221> NAME/KEY: MISC_FEATURE
<222> LOCATION: (2)..(2)
<223> OTHER INFORMATION: Xaa at position 2 is any amino acid or phospho-
      threonine
<220> FEATURE:
<221> NAME/KEY: MISC_FEATURE
<222> LOCATION: (2)..(3)
<223> OTHER INFORMATION: At least one of Xaa at position 2 or 3 is a
      phospho-amino acid
<220> FEATURE:
<221> NAME/KEY: MISC_FEATURE
<222> LOCATION: (3)..(3)
<223> OTHER INFORMATION: Xaa at position 3 is tyrosine or phospho-
      tyrosine
<220> FEATURE:
<221> NAME/KEY: MISC_FEATURE
```

```
<222> LOCATION: (4)..(5)
<223> OTHER INFORMATION: Xaa at position 4 or 5 are independently any
      amino acid
<220> FEATURE:
<221> NAME/KEY: MISC_FEATURE
<222> LOCATION: (6)..(6)
<223> OTHER INFORMATION: Xaa at position 6 is I, V or L

<400> SEQUENCE: 2

Xaa Xaa Xaa Xaa Xaa Xaa
1               5

<210> SEQ ID NO 3
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa at position 3 is threonine or phospho-
      threonine
<220> FEATURE:
<221> NAME/KEY: MISC_FEATURE
<222> LOCATION: (3)..(4)
<223> OTHER INFORMATION: at least one of Xaa at position 3 or 4 is a
      phospho-amino acid
<220> FEATURE:
<221> NAME/KEY: MISC_FEATURE
<222> LOCATION: (4)..(4)
<223> OTHER INFORMATION: Xaa at position 4 is tyrosine or phospho-
      tyrosine

<400> SEQUENCE: 3

Glu Ile Xaa Xaa Ala Glu Val Arg Phe Lys Asn Glu Phe Lys Ser
1               5                   10                  15

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
gaagcatcca ggaagtcagc                                                 20

<210> SEQ ID NO 5
<211> LENGTH: 19
<212> TYPE: DNA
<213> ORGANISM: Artificial Sequence
<220> FEATURE:
<223> OTHER INFORMATION: Synthetic Construct

<400> SEQUENCE: 5
ctattccttc gggcctgtc                                                  19

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
tagagggaca agtggcgttc                                                 20

<210> SEQ ID NO 7
```

```
<211> LENGTH: 18
<212> TYPE: DNA
<213> ORGANISM: Artificial Sequence
<220> FEATURE:
<223> OTHER INFORMATION: Synthetic Construct

<400> SEQUENCE: 7
cgctgagcca gtcagtgt                                            18

<210> SEQ ID NO 8
<211> LENGTH: 24
<212> TYPE: DNA
<213> ORGANISM: Artificial Sequence
<220> FEATURE:
<223> OTHER INFORMATION: Synthetic Construct

<400> SEQUENCE: 8
tatcaaagca acccacccac ctcc                                     24

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
aacaggtctg tgatgcccctt                                         20

<210> SEQ ID NO 10
<211> LENGTH: 15
<212> TYPE: PRT
<213> ORGANISM: Artificial Sequence
<220> FEATURE:
<223> OTHER INFORMATION: Synthetic Construct

<400> SEQUENCE: 10

Glu Ile Thr Tyr Ala Glu Val Arg Phe Lys Asn Glu Phe Lys Ser
1               5                   10                  15

<210> SEQ ID NO 11
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Tyrosine at position 4 is phosphorylated

<400> SEQUENCE: 11

Glu Ile Thr Tyr Ala Glu Val Arg Phe Lys Asn Glu Ser
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Threonine at position 3 is phosphorylated

<400> SEQUENCE: 12

Glu Ile Thr Tyr Ala Glu Val Arg Phe Lys Asn Glu Phe Lys Ser
```

```
<210> SEQ ID NO 13
<211> LENGTH: 15
<212> TYPE: PRT
<213> ORGANISM: Artificial Sequence
<220> FEATURE:
<223> OTHER INFORMATION: Synthetic Construct

<400> SEQUENCE: 13

Lys Glu Asn Phe Lys Arg Phe Val Ala Tyr Glu Thr Ile Glu Ser
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic Construct

<400> SEQUENCE: 14

Glu Ile Thr Tyr Ala Glu Val Arg Phe Lys Asn Glu Phe Lys Ser
1               5                   10                  15

<210> SEQ ID NO 15
<211> LENGTH: 6
<212> TYPE: PRT
<213> ORGANISM: Artificial Sequence
<220> FEATURE:
<223> OTHER INFORMATION: Synthetic Construct

<400> SEQUENCE: 15

Ile Thr Tyr Ala Glu Val
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: The tyrosine at position 3 is phosphorylated

<400> SEQUENCE: 16

Ile Thr Tyr Ala Glu Val
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: The threonine at position 2 is phophorylated

<400> SEQUENCE: 17

Ile Thr Tyr Ala Glu Val
1               5

<210> SEQ ID NO 18
<211> LENGTH: 6
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: The tyrosine at position 3 is phosphorylated

<400> SEQUENCE: 18

Val Ala Tyr Glu Thr Ile
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: The threonine at position 5 is phosphorylated

<400> SEQUENCE: 19

Val Ala Tyr Glu Thr Ile
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

Ile Thr Tyr Ala Glu Val Arg Phe Lys Asn
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: The thyrosine at position 4 is phosphorylated

<400> SEQUENCE: 21

Glu Ile Thr Tyr Ala Glu Val Arg Phe Lys Asn
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: The threonine at position 3 is phosphorylated

<400> SEQUENCE: 22

Glu Ile Thr Tyr Ala Glu Val Arg Phe Lys Asn
1               5                   10

<210> SEQ ID NO 23
```

```
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(0)
<223> OTHER INFORMATION: The tyrosine at position 3 is phosphorylated

<400> SEQUENCE: 23

Val Ala Tyr Glu Thr Ile Lys Asn Phe Arg
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: The threonine at position 5 is phosphorylated

<400> SEQUENCE: 24

Val Ala Tyr Glu Thr Ile Lys Asn Phe Arg
1               5                   10

<210> SEQ ID NO 25
<211> LENGTH: 15
<212> TYPE: PRT
<213> ORGANISM: Artificial Sequence
<220> FEATURE:
<223> OTHER INFORMATION: Synthetic Construct

<400> SEQUENCE: 25

Glu Ile Thr Tyr Ala Glu Val Arg Phe Lys Asn Glu Phe Lys Ser
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: The tyrosine at position 4 is phosphorylated

<400> SEQUENCE: 26

Glu Ile Thr Tyr Ala Glu Val Arg Phe Lys Asn Glu Phe Lys Ser
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: The threonine at position 3 is phosphorylated

<400> SEQUENCE: 27

Glu Ile Thr Tyr Ala Glu Val Arg Phe Lys Asn Glu Phe Lys Ser
1               5                   10                  15
```

<210> SEQ ID NO 28
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: The tyrosine at position 10 is phosphorylated

<400> SEQUENCE: 28

Lys Glu Asn Phe Lys Arg Phe Val Ala Tyr Glu Thr Ile Glu Ser
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (12)..(12)
<223> OTHER INFORMATION: The threonine at position 12 is phosphorylated

<400> SEQUENCE: 29

Lys Glu Asn Phe Lys Arg Phe Val Ala Tyr Glu Thr Ile Glu Ser
1               5                   10                  15

<210> SEQ ID NO 30
<211> LENGTH: 17
<212> TYPE: DNA
<213> ORGANISM: Artificial Sequence
<220> FEATURE:
<223> OTHER INFORMATION: Synthetic Construct

<400> SEQUENCE: 30
catgcttcag gggccgg                                                17

<210> SEQ ID NO 31
<211> LENGTH: 17
<212> TYPE: DNA
<213> ORGANISM: Artificial Sequence
<220> FEATURE:
<223> OTHER INFORMATION: Synthetic Construct

<400> SEQUENCE: 31
ccggcccctg aagcatg                                                17

<210> SEQ ID NO 32
<211> LENGTH: 22
<212> TYPE: DNA
<213> ORGANISM: Artificial Sequence
<220> FEATURE:
<223> OTHER INFORMATION: Synthetic Construct

<400> SEQUENCE: 32
cttgagcagg gtctctgcat cc                                          22

<210> SEQ ID NO 33
<211> LENGTH: 22
<212> TYPE: DNA
<213> ORGANISM: Artificial Sequence
<220> FEATURE:
<223> OTHER INFORMATION: Synthetic Construct

<400> SEQUENCE: 33

```
ggatgcagag accctgctca ag                                              22

<210> SEQ ID NO 34
<211> LENGTH: 20
<212> TYPE: DNA
<213> ORGANISM: Artificial Sequence
<220> FEATURE:
<223> OTHER INFORMATION: Synthetic Construct

<400> SEQUENCE: 34
ctccgcgatg tcatgttcct                                                 20

<210> SEQ ID NO 35
<211> LENGTH: 20
<212> TYPE: DNA
<213> ORGANISM: Artificial Sequence
<220> FEATURE:
<223> OTHER INFORMATION: Synthetic Construct

<400> SEQUENCE: 35
aggaacatga catcgcggag                                                 20

<210> SEQ ID NO 36
<211> LENGTH: 20
<212> TYPE: DNA
<213> ORGANISM: Artificial Sequence
<220> FEATURE:
<223> OTHER INFORMATION: Synthetic Construct

<400> SEQUENCE: 36
ccagtcactc gcaccatcgc                                                 20

<210> SEQ ID NO 37
<211> LENGTH: 20
<212> TYPE: DNA
<213> ORGANISM: Artificial Sequence
<220> FEATURE:
<223> OTHER INFORMATION: Synthetic Construct

<400> SEQUENCE: 37
cagccatggt tcccccccaac                                                20

<210> SEQ ID NO 38
<211> LENGTH: 18
<212> TYPE: DNA
<213> ORGANISM: Artificial Sequence
<220> FEATURE:
<223> OTHER INFORMATION: Synthetic Construct

<400> SEQUENCE: 38
gcgcgcgttc atccgact                                                   18

<210> SEQ ID NO 39
<211> LENGTH: 18
<212> TYPE: DNA
<213> ORGANISM: Artificial Sequence
<220> FEATURE:
<223> OTHER INFORMATION: Synthetic Construct

<400> SEQUENCE: 39
tcagccatct tgcgcgcg                                                   18

<210> SEQ ID NO 40
<211> LENGTH: 18
<212> TYPE: DNA
```

```
<213> ORGANISM: Artificial Sequence
<220> FEATURE:
<223> OTHER INFORMATION: Synthetic Construct

<400> SEQUENCE: 40
agcaccaaca atcaacgg                                                 18

<210> SEQ ID NO 41
<211> LENGTH: 18
<212> TYPE: DNA
<213> ORGANISM: Artificial Sequence
<220> FEATURE:
<223> OTHER INFORMATION: Synthetic Construct

<400> SEQUENCE: 41
ggccccacca gtctactg                                                 18

<210> SEQ ID NO 42
<211> LENGTH: 20
<212> TYPE: DNA
<213> ORGANISM: Artificial Sequence
<220> FEATURE:
<223> OTHER INFORMATION: Synthetic Construct

<400> SEQUENCE: 42
ttttccgagg tagtaccgtg                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic Construct

<400> SEQUENCE: 43
gtgccatgat ggagcctttt                                               20

<210> SEQ ID NO 44
<211> LENGTH: 18
<212> TYPE: DNA
<213> ORGANISM: Artificial Sequence
<220> FEATURE:
<223> OTHER INFORMATION: Synthetic Construct

<400> SEQUENCE: 44
attgaacact accatggt                                                 18

<210> SEQ ID NO 45
<211> LENGTH: 18
<212> TYPE: DNA
<213> ORGANISM: Artificial Sequence
<220> FEATURE:
<223> OTHER INFORMATION: Synthetic Construct

<400> SEQUENCE: 45
tggtaccatc acaagtta                                                 18

<210> SEQ ID NO 46
<211> LENGTH: 20
<212> TYPE: DNA
<213> ORGANISM: Artificial Sequence
<220> FEATURE:
<223> OTHER INFORMATION: Synthetic Construct

<400> SEQUENCE: 46
agccgccgcc gccgccgcca                                               20
```

<210> SEQ ID NO 47
<211> LENGTH: 21
<212> TYPE: DNA
<213> ORGANISM: Artificial Sequence
<220> FEATURE:
<223> OTHER INFORMATION: Synthetic Construct

<400> SEQUENCE: 47
atggcggcgg cggcggcggc a                                             21

<210> SEQ ID NO 48
<211> LENGTH: 20
<212> TYPE: DNA
<213> ORGANISM: Artificial Sequence
<220> FEATURE:
<223> OTHER INFORMATION: Synthetic Construct

<400> SEQUENCE: 48
acacacagcc cattccaggt                                               20

<210> SEQ ID NO 49
<211> LENGTH: 20
<212> TYPE: DNA
<213> ORGANISM: Artificial Sequence
<220> FEATURE:
<223> OTHER INFORMATION: Synthetic Construct

<400> SEQUENCE: 49
acctggaatg ggctgtgtgt                                               20

<210> SEQ ID NO 50
<211> LENGTH: 17
<212> TYPE: DNA
<213> ORGANISM: Artificial Sequence
<220> FEATURE:
<223> OTHER INFORMATION: Synthetic Construct

<400> SEQUENCE: 50
gataaagaag cagcgaa                                                  17

<210> SEQ ID NO 51
<211> LENGTH: 17
<212> TYPE: DNA
<213> ORGANISM: Artificial Sequence
<220> FEATURE:
<223> OTHER INFORMATION: Synthetic Construct

<400> SEQUENCE: 51
ttcgctgctt ctttatc                                                  17

<210> SEQ ID NO 52
<211> LENGTH: 20
<212> TYPE: DNA
<213> ORGANISM: Artificial Sequence
<220> FEATURE:
<223> OTHER INFORMATION: Synthetic Construct

<400> SEQUENCE: 52
ccatatttcc cgctcgcgtg                                               20

<210> SEQ ID NO 53
<211> LENGTH: 20
<212> TYPE: DNA
<213> ORGANISM: Artificial Sequence
<220> FEATURE:

<223> OTHER INFORMATION: Synthetic Construct

<400> SEQUENCE: 53
cacgcgagcg ggaaatatgg                                           20

<210> SEQ ID NO 54
<211> LENGTH: 19
<212> TYPE: DNA
<213> ORGANISM: Artificial Sequence
<220> FEATURE:
<223> OTHER INFORMATION: Synthetic Construct

<400> SEQUENCE: 54
ttctcgaccc catcctggc                                            19

<210> SEQ ID NO 55
<211> LENGTH: 19
<212> TYPE: DNA
<213> ORGANISM: Artificial Sequence
<220> FEATURE:
<223> OTHER INFORMATION: Synthetic Construct

<400> SEQUENCE: 55
gccaggatgg ggtcgagaa                                            19

<210> SEQ ID NO 56
<211> LENGTH: 18
<212> TYPE: DNA
<213> ORGANISM: Artificial Sequence
<220> FEATURE:
<223> OTHER INFORMATION: Synthetic Construct

<400> SEQUENCE: 56
gtcttgttca gctcctgc                                             18

<210> SEQ ID NO 57
<211> LENGTH: 18
<212> TYPE: DNA
<213> ORGANISM: Artificial Sequence
<220> FEATURE:
<223> OTHER INFORMATION: Synthetic Construct

<400> SEQUENCE: 57
gcaggagctg aacaagac                                             18

<210> SEQ ID NO 58
<211> LENGTH: 18
<212> TYPE: DNA
<213> ORGANISM: Artificial Sequence
<220> FEATURE:
<223> OTHER INFORMATION: Synthetic Construct

<400> SEQUENCE: 58
atagagggcc acaaaggt                                             18

<210> SEQ ID NO 59
<211> LENGTH: 18
<212> TYPE: DNA
<213> ORGANISM: Artificial Sequence
<220> FEATURE:
<223> OTHER INFORMATION: Synthetic Construct

<400> SEQUENCE: 59
acctttgtgg ccctctat                                             18

```
<210> SEQ ID NO 60
<211> LENGTH: 204
<212> TYPE: PRT
<213> ORGANISM: Homo sapiens

<400> SEQUENCE: 60

Met Thr Ser Glu Ile Thr Tyr Ala Glu Val Arg Phe Lys Asn Glu Phe
1               5                   10                  15

Lys Ser Ser Gly Ile Asn Thr Ala Ser Ser Ala Ala Ser Lys Glu Arg
            20                  25                  30

Thr Ala Pro His Lys Ser Asn Thr Gly Phe Pro Lys Leu Leu Cys Ala
        35                  40                  45

Ser Leu Leu Ile Phe Phe Leu Leu Ala Ile Ser Phe Phe Ile Ala
    50                  55                  60

Phe Val Lys Thr Ala Trp Ser Cys Cys Pro Lys Asn Trp Lys Ser Phe
65                  70                  75                  80

Ser Ser Asn Cys Tyr Phe Ile Ser Thr Glu Ser Ala Ser Trp Gln Asp
                85                  90                  95

Ser Glu Lys Asp Cys Ala Arg Met Glu Ala His Leu Leu Val Ile Asn
            100                 105                 110

Thr Gln Glu Gln Asp Phe Ile Phe Gln Asn Leu Gln Glu Ser
        115                 120                 125

Ala Tyr Phe Val Gly Leu Ser Asp Pro Glu Gly Gln Arg His Trp Gln
130                 135                 140

Trp Val Asp Gln Thr Pro Tyr Asn Glu Ser Ser Thr Phe Trp His Pro
145                 150                 155                 160

Arg Glu Pro Ser Asp Pro Asn Glu Arg Cys Val Val Leu Asn Phe Arg
                165                 170                 175

Lys Ser Pro Lys Arg Trp Gly Trp Asn Asp Val Asn Cys Leu Gly Pro
            180                 185                 190

Gln Arg Ser Val Cys Glu Met Met Lys Ile His Leu
        195                 200

<210> SEQ ID NO 61
<211> LENGTH: 198
<212> TYPE: PRT
<213> ORGANISM: Homo sapiens

<400> SEQUENCE: 61

Met Thr Ser Glu Ile Thr Tyr Ala Glu Val Arg Phe Lys Asn Glu Phe
1               5                   10                  15

Lys Ser Ser Gly Ile Asn Thr Ala Ser Ser Ala Val Phe Phe Gln Lys
            20                  25                  30

Tyr Ser Gln Leu Leu Glu Lys Lys Thr Thr Lys Glu Leu Val His Thr
        35                  40                  45

Thr Leu Glu Cys Val Lys Lys Asn Met Pro Val Glu Glu Thr Ala Trp
    50                  55                  60

Ser Cys Cys Pro Lys Asn Trp Lys Ser Phe Ser Ser Asn Cys Tyr Phe
65                  70                  75                  80

Ile Ser Thr Glu Ser Ala Ser Trp Gln Asp Ser Glu Lys Asp Cys Ala
                85                  90                  95

Arg Met Glu Ala His Leu Leu Val Ile Asn Thr Gln Glu Gln Asp
            100                 105                 110

Phe Ile Phe Gln Asn Leu Gln Glu Ser Ala Tyr Phe Val Gly Leu
        115                 120                 125

Ser Asp Pro Glu Gly Gln Arg His Trp Gln Trp Val Asp Gln Thr Pro
```

```
                130             135             140
Tyr Asn Glu Ser Ser Thr Phe Trp His Pro Arg Glu Pro Ser Asp Pro
145                 150                 155                 160

Asn Glu Arg Cys Val Val Leu Asn Phe Arg Lys Ser Pro Lys Arg Trp
                165                 170                 175

Gly Trp Asn Asp Val Asn Cys Leu Gly Pro Gln Arg Ser Val Cys Glu
                180                 185                 190

Met Met Lys Ile His Leu
        195

<210> SEQ ID NO 62
<211> LENGTH: 165
<212> TYPE: PRT
<213> ORGANISM: Homo sapiens

<400> SEQUENCE: 62

Met Thr Ser Glu Ile Thr Tyr Ala Glu Val Arg Phe Lys Asn Glu Phe
1               5                   10                  15

Lys Ser Ser Gly Ile Asn Thr Ala Ser Ser Ala Glu Thr Ala Trp Ser
                20                  25                  30

Cys Cys Pro Lys Asn Trp Lys Ser Phe Ser Ser Asn Cys Tyr Phe Ile
            35                  40                  45

Ser Thr Glu Ser Ala Ser Trp Gln Asp Ser Glu Lys Asp Cys Ala Arg
        50                  55                  60

Met Glu Ala His Leu Leu Val Ile Asn Thr Gln Glu Glu Gln Asp Phe
65                  70                  75                  80

Ile Phe Gln Asn Leu Gln Glu Gly Ser Ala Tyr Phe Val Gly Leu Ser
                85                  90                  95

Asp Pro Glu Gly Gln Arg His Trp Gln Trp Val Asp Gln Thr Pro Tyr
            100                 105                 110

Asn Glu Ser Ser Thr Phe Trp His Pro Arg Glu Pro Ser Asp Pro Asn
            115                 120                 125

Glu Arg Cys Val Val Leu Asn Phe Arg Lys Ser Pro Lys Arg Trp Gly
        130                 135                 140

Trp Asn Asp Val Asn Cys Leu Gly Pro Gln Arg Ser Val Cys Glu Met
145                 150                 155                 160

Met Lys Ile His Leu
            165
```

US 9,320,773 B2

COMPOUNDS AND THERAPEUTIC APPLICATIONS RELATED TO INHIBITION OF DENDRITIC CELL IMMUNORECEPTOR (DCIR) ACTIVITY AND SIGNALING EVENTS

RELATED APPLICATIONS

This patent application is a national stage filing under 35 U.S.C. §371 of international application No. PCT/CA2011/000888 filed on Aug. 4, 2011 which claimed priority to U.S. provisional application No. 61/374,742 filed on Aug. 18, 2010, the entire content of which is incorporated herein by reference.

FIELD OF THE INVENTION

The present invention relates to fields of medicine. The present invention concerns compounds and methods for interfering dendritic cell immunoreceptor (DCIR) activity and signaling events, more particularly for reducing human immunodeficiency virus (HIV) binding, entry and/or replication.

BACKGROUND OF THE INVENTION

It is now well-established that HIV-1 infection causes a slow but progressive impairment of the immune system and that a relentless destruction of CD4+ T cells represents another hallmark of HIV-1 infection.

HIV-1 uses primarily dendritic cells (DC) to penetrate the mucosal epithelium[1, 2]. The virus is then transferred and disseminated from this entry site[3] to T-cell zones in secondary lymphoid organs, where it can productively infect CD4+ T cells. The infection causes depletion of CD4+ T cells[4, 5], progressive impairment of the immune system, as well as chronic hyperactivation of both CD4+ and CD8+ T cells[4, 6, 7].

The initial attachment step of HIV-1 to DCs may occur through several interactions between the virus and the target cell surface (reviewed in[8, 9]). Recently, it was shown that the dendritic cell immunoreceptor (DCIR) can behave as an attachment factor for HIV-1[18]. This association results in trans infection of CD4+ T cells[13-17]. DCIR also contributes to cis-infection, that is, infection of surrounding CD4+ T cells by virions produced by DCs productively infected with HIV-1. It has also been shown that multiples isoforms of DCIR exists[22] and that the neck domain of the transmembrane isoform is important for HIV-1 binding and infection of DCs[18].

Phosphorylation and dephosphorylation are amongst the most important post-translational protein modifications often resulting in major changes in protein function and cellular function. Although it is known that of DCIR contains a ITIM domain and that phosphorylation of the ITIM domain plays an important role in the function of the receptor[25,26], nothing is known about the recruitment of the phosphatases or tyrosine kinases (TKs) after HIV-1 attachment to DCIR. Therefore, the precise contribution of DCIR-mediated intracellular signal transducers in virus capture, transfer and infection remains unknown and there is a particular need for compounds and method that would target one or more DCIR intracellular signalling events triggered following a physical interaction between DCIR and a virus particle.

Therefore, there is a need for the prevention and treatment of virus infections in subjects, more particularly in humans infected with or susceptible of HIV-1 infection. There is also a need for methods, compounds and pharmaceutical compositions for inhibiting dendritic cell immunoreceptor (DCIR) signalling in a mammalian cell.

SUMMARY OF THE INVENTION

According to a first aspect, the present invention relates to a method for inhibiting dendritic cell immunoreceptor (DCIR) signalling in a mammalian cell. In one embodiment, the method comprises contacting said mammalian cell with a compound interfering with an intracellular modulator participating in DCIR signalling, wherein said intracellular modulator is selected from the group consisting of: Spleen tyrosine kinase (Syk), Protein kinase C alpha (PKC-α), Hemopoietic cell kinase (Hck), FYN oncogene related to SRC, FGR, YES (Fyn), v-src sarcoma (Src), Extracellular signal-regulated kinases 1/2 (ERK 1/2), Mitogen-activated protein kinase 12 (MAPK or p38), Non receptor tyrosine phosphatase 1 (SHP-1), and Non receptor tyrosine phosphatase 2 (SHP-2).

Particular aspects of the present invention concern methods for the prevention or treatment of a human immunodeficiency virus (HIV) infection. In one embodiment, the method comprises administering to a subject in need thereof a compound interfering with an intracellular signalling event triggered following a physical interaction between HIV and a dendritic cell immunoreceptor (DCIR). In preferred embodiments the intracellular modulator is selected from the intracellular modulators listed hereinbefore.

Additional aspects concerns methods for reducing binding to, entry into and/or replication within the mammalian cell of viruses whose infection is directly related to a physical interaction with the DCIR of the cell to be infected. In preferred embodiment, the method is for reducing human immunodeficiency virus (HIV) binding, entry and/or replication.

In one embodiment, the DCIR comprises a ITIM motif ITYAEV (SEQ ID NO. 15) and the compound interferes indirectly with a binding interaction between said ITIM motif and the intracellular modulator. In another embodiment, the compound interferes indirectly with a binding interaction involving a Src homology-2 domain (SH2)-containing tyrosine phosphatase of the intracellular modulator. In a further embodiment, the compound interferes indirectly phosphorylation of the tyrosine on the ITIM motif and/or interferes indirectly phosphorylation of the threonine on the ITIM motif, thereby reducing internalization of DCIR in the mammalian cell.

In one particular embodiment, compounds for use according to the method of the invention includes peptides and mixtures of peptides comprising an amino acid sequence as set forth in SEQ ID NO. 2 and defined hereinafter. In another embodiment, the compound is a peptide comprising an amino acid sequence as set forth in SEQ ID NO. 15 and defined hereinafter. In further embodiments, the compound consists of consists of a polypeptide, or a mixture of polypeptides, of SEQ ID NOs 11, 12, 16, 17, 21, 22, 26 and 27 as defined herein.

In another particular embodiment, compounds for use according to the method of the invention is an antisense molecule comprising at least 10 nucleotides complementary to the coding strand of at least one of Syk, PKC-α, Hck, Fyn, Src, ERK 1/2, p38, SHP-1, and SHP-2. In preferred embodiments the antisense molecule comprises a nucleic acid sequence selected from the group consisting of: SEQ ID NO. 30, SEQ ID NO. 36, SEQ ID NO.38, SEQ ID NO.40, SEQ ID NO.42, SEQ ID NO.44, SEQ ID NO.54, SEQ ID NO.50, SEQ ID NO.58, SEQ ID NO.46, SEQ ID NO.56, SEQ ID NO.32, and SEQ ID NO.34.

According to another aspect, the present invention relates to a peptide comprising an amino acid sequence as set forth in SEQ ID NO.2:

```
Xaa₁Xaa₂Xaa₃Xaa₄Xaa₅Xaa₆     (SEQ ID NO.: 2)
``` wherein
Xaa$_1$ is S, I, V or L;
Xaa$_2$ is any amino acid or phospho-threonine;
Xaa$_3$ is tyrosine or phospho-tyrosine;
Xaa$_4$ or Xaa$_5$ is any amino acid;
Xaa$_6$ is I, V or L;
at least one of Xaa$_2$ or Xaa$_3$ is a phosphorylated residue.

According to another aspect, the present invention relates to a peptide comprising an amino acid sequence as set forth in SEQ ID NO.15:

```
ITYAEV          (SEQ ID NO.: 15)
``` wherein at least one of the threonine (T) or tyrosine (Y) residue is phosphorylated.

According to another aspect, the present invention relates to polynucleotides, including but not limited to antisense molecules. In one embodiment, the polynucleotide comprises at least 10 nucleotides complementary to the coding strand of one or more intracellular modulator as defined herein. In particular embodiments the intracellular modulator is selected among Syk, PKC-α, Hck, Fyn, Src, ERK 1/2, p38, SHP-1, and SHP-2. In preferred embodiments, the polynucleotide comprises a nucleic acid sequence selected from the group consisting of: SEQ ID NO. 30, SEQ ID NO.36, SEQ ID NO.38, SEQ ID NO.40, SEQ ID NO.42, SEQ ID NO.44, SEQ ID NO.54, SEQ ID NO.50, SEQ ID NO.58, SEQ ID NO.46, SEQ ID NO.56, SEQ ID NO.32, and SEQ ID NO.34.

The peptide(s) and/or polynucleotide(s) of the invention may further comprise a label and or has been modified (e.g. deletion, addition or substitution). Preferably the peptide(s) and/or polynucleotide(s) of the invention are for an administration to a human subject. Accordingly, related aspects of the present invention concerns pharmaceutical compositions comprising one or more peptide and/or one or more polynucleotide as defined herein.

Another related aspect concerns the use of such peptide(s), polynucleotide(s) and/or pharmaceutical compositions for inhibiting dendritic cell immunoreceptor (DCIR) signalling in a mammalian cell. Another related aspect concerns the use of such peptide(s), polynucleotide(s) and/or pharmaceutical compositions comprising the same for the prevention and/or treatment of a mammalian virus infection, including but not limited to prevention and/or treatment human immunodeficiency virus (HIV) infection. Additional types of virus infection which could benefit from the present invention include for instance, those infections caused by viruses of the immunodeficiency viruses family, hepaciviruses and herpes viruses.

According to a further aspect, the present invention relates to a method for the prevention or treatment of a virus infection in a mammal, the method comprising administering to a mammal in need thereof a compound inhibiting intracellular production and/or accumulation of free radicals in the mammalian cell. According to this method, inhibition of the intracellular production and/or accumulation of free radicals reduces expression of DCIR and reduces virus entry or capture into the mammalian cell by DCIR. In particular embodiments the compound is selected from the group consisting of: catalase, inhibitors of nitrogen oxygen syntase, and/or inhibitors of NADPH oxydase.

Yet, a further aspect of the invention concerns a method for the prevention and/or treatment of a virus infection in a mammal, the method comprising administering to a subject in need thereof an inhibitor of apoptosis. According to this method, the inhibitor of apoptosis reduces expression of DCIR and thereby reduces virus entry or capture into the mammalian cell by DCIR. In a particular embodiment the inhibitor of apoptosis is a caspase inhibitor.

Additional features of the invention will be apparent from review of the disclosure, figures, and description of the invention below.

BRIEF DESCRIPTION OF THE FIGURES

FIG. 1 shows that HIV-1 binding/entry and replication is increased in Raji-CD4 cells stably transduced with DCIR. FIG. 1A: Raji-CD4 cells were infected either with a retroviral control vector (left panel) or a retroviral vector encoding for human DCIR (right panel). Forty-eight hours after infection, cells expressing high levels of DCIR were isolated by flow cytometry based on eGFP expression. Surface expression of DCIR was monitored by flow cytometry using a combination of PE-labelled anti-DCIR antibody (dotted lines) and a control isotype-matched antibody (continuous lines). Data shown correspond to a single experiment representative of three independent experiments. FIG. 1B: Raji-CD4 and Raji-CD4-DCIR cells were exposed to NL4-3 for 60 min. After three washes with PBS to remove non-adsorbed virus, cell-associated virus (attached and internalized) was quantified by measuring the p24 content. Data shown correspond to the means±SD of triplicate samples from three independent experiments. The asterisk denotes statistically significant data (*, P<0.05). FIG. 1C: Raji-CD4 and Raji-CD4-DCIR were exposed to NL4-3 for 2 hours. After three washes with PBS to remove excess virus, cells were maintained in culture for up to 9 days. Cell-free culture supernatants were collected at the indicated time points and assayed for p24 content. Data shown correspond to the means±SD of triplicate samples from three independent experiments. The asterisk denotes statistically significant data (*, P<0.05). D.P.I., Days post-infection.

FIG. 2A: Raji-CD4 and Raji-CD4-DCIR cells were either left untreated or treated with SSG (100 µg/ml) for 10 min at 37° C. Thereafter, cells were pulsed with NL4-3 for 60 min. After three washes with PBS to remove non-adsorbed virus, cell-associated virus was quantified by measuring the p24 content. Data shown correspond to the means±SD of triplicate samples from three combined independent experiments. The asterisk denotes statistically significant data (*, P<0.05; **, P<0.01). FIG. 2B: Cells were either left untransfected or transfected with a sense or antisense oligonucleotide specific for the signalling protein of interest. Next, cells were pulsed with NL4-3 for 60 min. After three washes with PBS to eliminate unbound virus, cell-associated virus was quantified by measuring the p24 content. Data shown correspond to the means±SD of triplicate samples from three combined independent experiments. The asterisk denotes statistically significant data (*, P<0.05; **, P<0.01). After gene silencing, the diminution of the targeted protein was verified by western blots, provided as an insert for each graph.

FIG. 3 shows DCIR-mediated enhancing effect on HIV-1 binding/entry requires tyrosine kinase families Src, Tec and Syk. Experimental procedures used here are similar to the ones described in FIG. 2 except that the following inhibitors and oligonucleotides were tested: Src family tyrosine kinase inhibitor PP2 (10 μM) (FIG. 3A), oligonucleotides specific for Src (FIG. 3B), BTK inhibitor LFM-A13 (25 μM) (panel C), Syk kinase inhibitor piceatannol (10 μM) (FIG. 3D), oligonucleotides specific for Syk (FIG. 3E), and PI3K inhibitor wortmannin (50 nM) (FIG. 3F).

FIG. 6 shows that signalling proteins responsible for the DCIR-mediated enhancing effect on HIV-1 binding/entry are also required to achieve a superior virus infection. FIG. 6A: Raji-CD4 and Raji-CD4-DCIR were either left untreated or preincubated with tyrosine phosphatase inhibitor SSG (100 μg/ml); Syk inhibitor piceatannol (10 μM); Src inhibitor PP2 (10 μM); classical PKC inhibitor Gö6976 (1 μM); MAPK p38 inhibitor SB203580 (2 μM), MAP kinase inhibitor PD98059 (20 nM) for 10 min. FIG. 6B: Raji-CD4 and Raji-CD4-DCIR were treated with Oligofectamine and then either left untreated or exposed to a sense or an antisense oligonucleotide against different signalling proteins during 5 hours. Next, cells were exposed to NL4-3 for 24 hours. Virus infection was determined by real-time PCR of spliced Tat mRNA. Data shown correspond to the means±SD of triplicate samples from three independent experiments. The asterisk denotes statistically significant data (*, P<0.05; ***, P<0.001).

FIG. 7 shows that DCIR-mediated enhancing effect on HIV-1 replication requires phosphorylation of the ITIM domain. FIG. 7A: Raji-CD4 cells were transduced with a retroviral vector expressing either a wild-type form of DCIR, a T6F mutant of DCIR, or a Y7F mutant of DCIR. Surface expression level of DCIR was assessed by flow cytometry using a combination of PE-labelled anti-DCIR antibody (dotted lines) and a control isotype-matched antibody (continuous lines). Data shown correspond to a single experiment representative of three independent experiments. FIG. 7B: For the virus binding/entry assay shown in the left panel, the indicated cell lines were exposed to NL4-3. For the infection assay shown in the right panel, the same cells were exposed to NL4-3 for 2 hours at 37° C., and then maintained in culture for 9 days. FIG. 7C: IM-MDDCs were treated with Pro-Ject only, with a control peptide or an ITIM peptide, either not phosphorylated or phosphorylated on the tyrosine or threonine residue, during 5 min at 37° C. Next, cells were pulsed with NL4-3balenv for 60 min at 37° C. and washed extensively before measuring the p24 content (left panel). In some experiments, similarly treated IM-MDDCs were pulsed with NL4-3balenv for 2 hours at 37° C., washed extensively and maintained in complete culture medium supplemented with GM-CSF and IL-4. Cell-free culture supernatants were quantified by measuring the p24 content. Data shown correspond to the means of triplicate samples from 3 independent experiments. The asterisk denotes statistically significant data (*, P<0.05; ***, P<0.001).

FIG. 8 shows the amino acid sequences and domains of the four isoforms of DCIR known in humans: SEQ ID NO:1 (Isoform 1), SEQ ID NO:60 (Isoform 2), SEQ ID NO:61 (Isoform 3), and SEQ ID NO:62 (Isoform 4).

FIG. 9 shows that HIV-1 induces DCIR expression in CD4$^+$ T cells under both in vivo and in vitro conditions. Purified CD4$^+$ T cells were isolated from uninfected healthy donors and two HIV-1-infected aviremic/treated persons (FIG. 9A) or three viremic/treatment-naive patients (FIG. 9B). Next, cells (1×10$^6$) were stained with the R-PE-labeled anti-DCIR monoclonal Ab. Expression of DCIR is shown as a dotted line, whereas the continuous line represents staining obtained with an isotype-matched irrelevant control Ab. For uninfected healthy donors, data shown correspond to a single experiment representative of 5 distinct donors. (FIG. 9C) Purified human primary CD4$^+$ T cells (1×10$^6$) were pulsed or not with NL4-3 (100 ng of p24). Three days later, DCIR expression was evaluated by flow cytometric analysis through the use of a R-PE-labeled anti-DCIR monoclonal Ab. Expression of DCIR is shown as a dotted line, whereas the continuous line represents results obtained with an isotype-matched irrelevant control Ab. Data shown correspond to a single experiment representative of 3 independent experiments.

FIG. 16A: Mitogen-activated CD4+ T cells (1×10$^6$) were first either left untreated or treated for 1 h with the caspase inhibitor Z-VAD-FMK (50 nM), after which $H_2O_2$ (30 µM) was added, where indicated. DCIR expression was monitored 16 h later by flow cytometry. Expression of DCIR is shown as a dotted line, whereas the continuous line represents staining obtained with an isotype-matched irrelevant control Ab. Data shown correspond to a single experiment representative of 3 independent experiments. FIG. 16B: Mitogen-stimulated CD4+ T cells (1×10$^6$) were first treated for 16 h with $H_2O_2$ (i.e. 30 µM). Thereafter, DCIR surface expression and caspase activation were monitored by flow cytometric analysis using a double-staining method consisting of FITC-VAD-FMK followed by the R-PE-conjugated anti-DCIR. Data shown correspond to a single experiment representative of 4 independent experiments.

FIG. 17A: Cells were next exposed to NL4-3 (100 ng of p24) for 1 h at 37° C., extensively washed to remove unabsorbed virons before assessing the p24 content. FIG. 17B: Cells were first incubated with NL4-3 (100 ng of p24) for 2 h at 37° C., washed extensively to remove input virus and cultured in complete culture RPMI-1640 medium supplemented with rhIL-2 for the indicated number of days. Cell-free supernatants were collected and assayed for the p24 content. FIG. 17C: Cells were exposed to NL4-3 (100 ng of p24) for 2 h at 37° C., next washed extensively to remove input virus, and finally co-cultured with autologous CD4+ T cells in complete culture RPMI-1640 medium supplemented with rhIL-2 for the indicated number of days. Cell-free supernatants were collected and assayed for the p24 content. Virus production at day 2 is depicted in the small inserts (FIGS. 17B and C). FIG. 17D: Cells were exposed to NL4-3 (100 ng of p24) for 2 h at 37° C., washed extensively to remove input virus, and maintained in complete culture medium supplemented with rhIL-2 for 3 days. Next, DCIR-negative and -positive cells (used as transmitter cells) were isolated with magnetic beads and co-cultured with uninfected CD4+ T cells (used as recipient cells). Cell-free supernatants were collected at 3 days following initiation of the co-culture and assayed for the p24 content. FIG. 17E: Cells were first exposed to NL4-3 for 2 h at 37° C. Cells were extensively washed to remove unabsorbed virions and half of the cells were used to estimate the percentage of cells positive for surface DCIR and intracellular p24. FIG. 17F: The other half was maintained for 3 days in culture before assessing both DCIR and p24. Data shown represent the means±SD of triplicate samples and correspond to a single experiment representative of three independent experiments. Asterisks denote statistically significant data (*, P<0.05; , P<0.01; *, P<0.001).

DETAILED DESCRIPTION OF THE INVENTION

A) General Overview of the Invention

The inventors have discovered DCIR intracellular signalling events triggered following a physical interaction between DCIR and virus particles. More particularly, the inventors have found that the followings proteins are intracellular modulators participating in DCIR signalling: Spleen tyrosine kinase (Syk), Protein kinase C alpha (PKC-α), Hemopoietic cell kinase (Hck), FYN oncogene related to SRC, FGR, YES (Fyn), v-src sarcoma (Src), Extracellular signal-regulated kinases 1/2 (ERK 1/2), Mitogen-activated protein kinase 12 (MAPK or p38), Non receptor tyrosine phosphatase 1 (SHP-1), and Non receptor tyrosine phosphatase 2 (SHP-2). Accordingly, the inventors have found the pharmacological significance of targeting one or more of these intracellular modulators in the prevention or treatment of virus infections.

Figure 19:
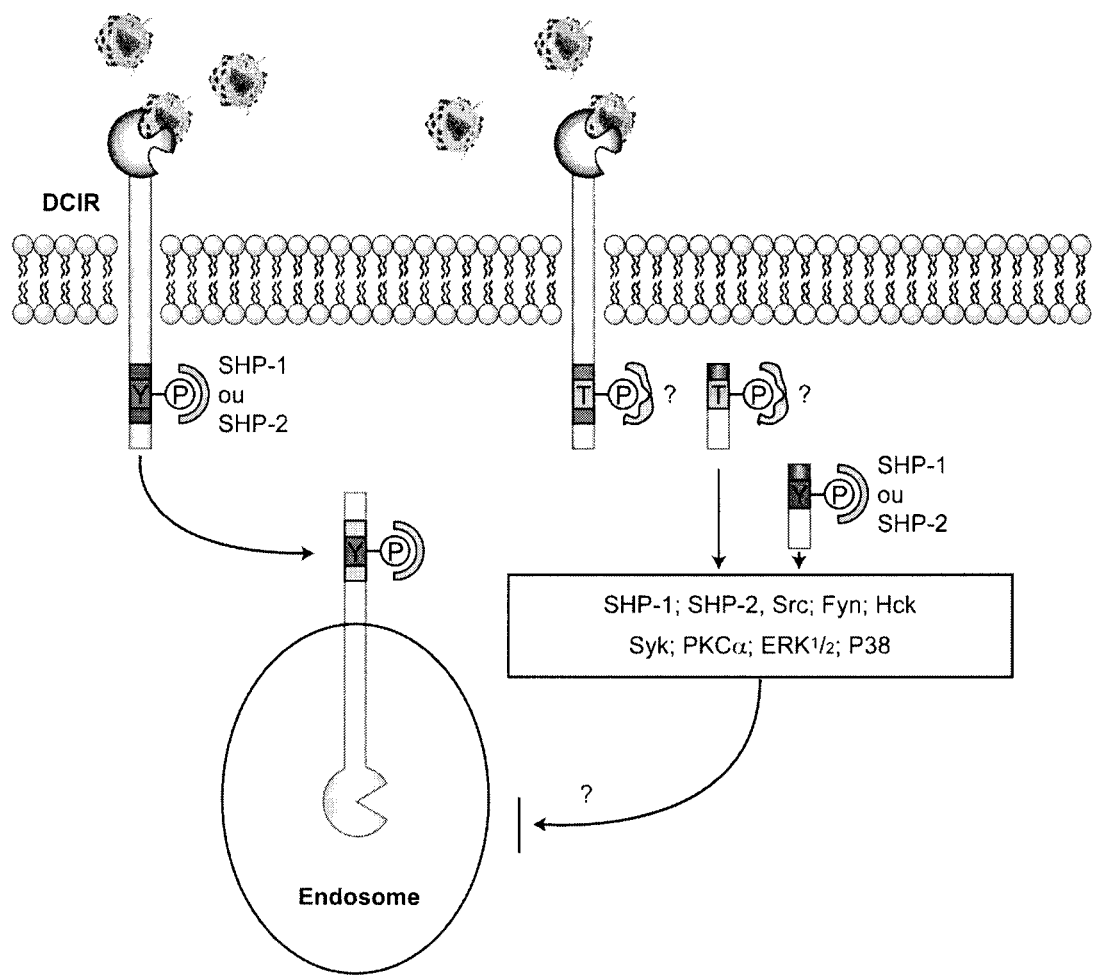
FIG. 19 is a schema illustrating that phosphorylated peptides similar to ITIM motif of DCIR, block interaction of this lectin with several proteins involved after HIV-1 interaction.

The present inventors have also found that it is possible to reduce internalization of DCIR in the mammalian cell by interfering with phosphorylation of the tyrosine residue and/or by interfering with phosphorylation of the threonine residue, of the ITIM motif of DCIR. Accordingly, the inventors have found the pharmacological significance of interfering directly or indirectly with the phosphorylation of one or both of these residues and described herein are compounds capable of interfering, at least indirectly with a binding interaction between the ITIM motif and intracellular modulators, and more particularly compounds interfering at least indirectly with a binding interaction involving a Src homology-2 domain (SH2)-containing tyrosine phosphatase of the intracellular modulator as illustrated in FIG. 19

In addition, the inventors have found that intracellular production and/or accumulation of free radicals in a virus-infected mammalian cell is related to an increase expression of DCIR and to a greater virus entry or capture cell by DCIR. Therefore, it may be possible to reduce virus entry and/or capture into the mammalian cell by DCIR by inhibiting intracellular production and/or accumulation of free radicals in the cell.

The inventors have also found that apoptosis may increase expression of DCIR. Therefore, the inventors propose to prevent or treat virus infection in mammals by administering inhibitor of apoptosis capable of reducing expression of DCIR.

B) Definitions

For the purpose of the present invention the following terms are defined below.

As used herein and in the appended claims, the singular forms “a”, “an”, and “the” include plural referents unless the context clearly indicates otherwise. Thus, for example, reference to “a compound” includes one or more of such compounds and reference to “the method” includes reference to equivalent steps and methods known to those of ordinary skill in the art that could be modified or substituted for the methods described herein.

As used herein the term “subject” includes living organisms having or susceptible of virus infection. In preferred embodiments, the subject is a human patient in need of treatment, including but not limited to, a human patient having HIV or susceptible to a HIV infection. The term “subject” includes animals such as mammals. As used herein the term “mammal” or “mammalian”, in connection with cell, refers to cell susceptible of virus infection, including, but not limited to, infections by immunodeficiency viruses. The term mammal includes, but is not limited to, species such as human, a cat, horse, bovine, or mouse.

“DCIR” or “dendritic cell immunoreceptor” as used herein refers to a gene and the corresponding expressed receptor that is present at the surface of a cell's subject (e.g. a mammalian cell) and which is involved in initial attachment and entry of HIV-1 into mammalian cells. DCIR is also known as C-type lectin DDB27, C-type lectin domain family 4 member A, C-type lectin superfamily member 6, CLECSF6. This transmembrane protein is found on the surface of most antigen-presenting cells (i.e. DCs, monocytes, macrophages and B cells), as well as on granulocytes; on DCs, it is differentially expressed, depending on their maturation status[22]. In addition, LPS, IL-4 and TNFα down regulate its expression on neutrophils[23]. To date, four isoforms of DCIR are known in humans: two soluble isoforms, with or without a neck domain, and two transmembrane isoforms, with or without a neck domain[22] and all have an ITIM motifs as illustrated in FIG. 8. DCIR is a C-type lectin a family of proteins which includes DCAR, dectin-2, BDCA-2, MCL and MINCLE. DCIR is the only member of the DCIR family containing an immunoreceptor tyrosine-based inhibitory motif (ITIM)[21,22]. The amino acid sequences of human DCIR are provided in FIG. 8 and as SEQ ID NO:1 (Isoform 1), SEQ ID NO:60 (Isoform 2), SEQ ID NO:61 (Isoform 3), and SEQ ID NO:62 (Isoform 4). The amino acid sequences of the various human isoforms (and other species) can also be found on GenBank™: human DCIR isoform 1 (237 aa; Acc. No. NP_057268.1), human DCIR isoform 2 (204 aa; Acc. No. NP_919432.1), human DCIR isoform 3 (198 aa; Acc. No. NP_919429.2), human DCIR isoform 4 (165 aa; Acc. No. NP_919430.1).

“Intracellular modulator” as used herein refers to a gene and the corresponding expressed protein participating in DCIR intracellular signalling events triggered following a physical interaction between DCIR and a virus particle. In accordance with the present invention, reference is made more particularly to the following proteins:

| Common Name | Acronym | Gene ID | Chromosome Location (Human) | Isoform (mRNA) Accession # | Protein Accession # | OMIM ™ Number |
|---|---|---|---|---|---|---|
| Spleen tyrosine kinase | SYK | 6850 | 9q22.2 | NM_003177 | P43405 | 600085 |
| Protein kinase C, alpha | PRKCA | 5578 | 17q24.2 | NM_002737 | P17252 | 176960 |
| Hemopoietic cell kinase | HCK | 3055 | 20q11.21 | | P08631 | 142370 |
| FYN oncogene related to SRC, FGR, YES | FYN | 2534 | 6q21 | NM_002037, NM_153047, NM_153048 | P06241 | 137025 |
| v-src sarcoma | SRC | 6714 | 20q11.23 | NM_005417, NM_198291 | P12931 | 190090 |
| Extracellular signal-regulated kinases 1 | ERK1/2 or MAPK1 | 5594 | 22q11.21 | NM_001040056, NM_001109891, NM_002745, NM_002746, NM_138957 NM_138957 | P28482 | 176948 |
| Extracellular signal-regulated kinases 2 | ERK 1/2 or MAPK3 | 5595 | 16p11.2 | | P27361 | 601795 |
| Mitogen-activated protein kinase 12 | P38 or MAPK12 | 6300 | 22q13.32 | NM_002969 | P53778 | 602399 |
| Non receptor tyrosine phosphatase 1 | SHP-1 | 5777 | 12p13.31 | NM_002831, NM_080548 | P29350 | 176883 |

-continued

| Common Name | Acronym | Gene ID | Chromosome Location (Human) | Isoform (mRNA) Accession # | Protein Accession # | OMIM ™ Number |
|---|---|---|---|---|---|---|
| Non receptor tyrosine phosphatase 2 | SHP-2 | 5781 | 12q24.13 | NM_002834 | Q06124 | 607785 |

As used herein, a "compound interfering with an intracellular modulator" refers to any compound capable of interfering directly, or indirectly with the DCIR intracellular signalling events involving one or more of the intracellular modulator listed hereinbefore. The invention encompasses all of the possible combinations of interference with 2, 3, 4, 5, 6 or more intracellular modulators. Examples of interference include, inhibiting or competing with a binding interaction between the ITIM motif of DCIR and the intracellular modulator(s). Other examples include inhibiting, reducing or blocking expression of the intracellular modulator(s). In accordance with particular embodiments of the present invention, examples of compounds interfering with an intracellular modulator include, but are not limited to, peptides and antisense molecules.

As used herein, the term "polypeptide" or "peptide" refers to an isolated or artificial amino acid sequence. The term is intended to encompass complete proteins, fragments thereof, artificially synthesized amino acid sequences and polypeptide comprising chemically modified amino acid residues (e.g. phosphorylation, glycosylation, label, tag, etc.).

The term "oligonucleotide" or "polynucleotide" as used herein refers to any DNA, RNA sequence or nucleic acid molecule comprised of two or more ribo- or deoxyribonucleotides, preferably more than three. The exact size of the oligonucleotide will depend on various factors and on the particular application and use of the oligonucleotide. This term includes DNA and fragments thereof, RNA and fragments thereof, cDNAs and fragments thereof, expressed sequence tags, artificial sequences including randomized artificial sequences. In some embodiments the polynucleotide is an antisense molecule.

The term "antisense" or "antisense molecule" as used herein refers to a single-stranded polynucleotide capable of specifically hybridizing to a target sequence. In preferred embodiments, antisense molecules according to the invention hybridize specifically to the coding strand of at least one of the intracellular modulator defined herein. The present invention encompass antisense oligonucleotides which comprise nucleotide analogues to improve the stability of the antisense molecule and/or to improve its membrane permeability. Exemplary embodiment of nucleotide analogues are known in the art. A few examples of nucleotide analogues are however provided herein. Suitable antisenses, interfering RNAs or other nucleic acid-based therapeutics according to the invention are those which are capable of interfering dendritic cell immunoreceptor (DCIR) activity and signaling events, more capable of reducing human immunodeficiency virus (HIV) binding, entry and/or replication.

With respect to single-stranded nucleic acids, particularly oligonucleotides such as antisense molecules, the term "specifically hybridizing" or "hybridizing specifically" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a polynucleotide of the invention, to the substantial exclusion of hybridization of the oligonucleotide with single-stranded nucleic acids of non-complementary sequence. Appropriate conditions enabling specific hybridization of single-stranded nucleic acid molecules of varying complementarity are well known in the art. For instance, one common formula for calculating the stringency conditions required to achieve hybridization between nucleic acid molecules of a specified sequence homology is set forth below (Sambrook et al., 1989, Molecular Cloning: A Laboratory Manual, Cold Spring Harbor Laboratory Press):

$$T_m = 81.5° C. + 16.6 \log [Na+] + 0.41(\% G+C) - 0.63(\% \text{formamide}) - 600/\#bp \text{ in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5 with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. With regard to the nucleic acids of the current invention, a moderate stringency hybridization is defined as hybridization in 6×SSC, 5×Denhardt's solution, 0.5% SDS and 100 µg/ml denatured salmon sperm DNA at 42° C. and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes. Interfering RNAs and/or antisenses according to the invention are preferably capable of hybridizing to a desired sequence under high stringency conditions.

C) Pharmaceutical Applications

The discovery of the identity of intracellular modulators participating in DCIR intracellular signalling events triggered following a physical interaction between DCIR and virus particles opens new avenues of prevention and treatment of virus infections.

As indicated hereinbefore and exemplified hereinafter, one aspect of the invention concerns methods, compounds and pharmaceutical compositions for inhibiting dendritic cell immunoreceptor (DCIR) signalling in a mammalian cell.

Another aspect of the invention concerns methods, compounds, and pharmaceutical compositions for the prevention or treatment of a virus infection in a mammal including, but not limited to, human immunodeficiency virus (HIV) infections.

The principles of the present invention may be applicable to any DCIR-expressing cell including, but not limited to, antigen-presenting cells (e.g. DCs, monocytes, macrophages and B cells), and granulocytes. The methods of the invention can be carried out in vivo and/or in vitro.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians.

As used herein, the terms "treatment" or "treating" of a subject includes the application or administration of a suitable compound, or composition of the invention as defined herein to a subject (or application or administration of a compound or composition of the invention to a cell or tissue from a subject) with the purpose of delaying, stabilizing, curing, healing, alleviating, relieving, altering, remedying, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement, remission, slowing disease progression or severity, stabilization, diminishing of symptoms or making the injury, pathology or condition more tolerable to the subject, slowing in the rate of degeneration or decline, making the final point of degeneration less debilitating, or improving a subject's physical or mental well-being. In some embodiments, the term "treating" can include increasing a subject's life expectancy and/or delay before additional treatments are required (e.g. joint replacement surgery).

As used herein, the term "prevention or treatment of a virus infection" includes blocking, reducing, inhibiting the binding to, the entry into and/or replication of viruses within a mammalian cell. In particular embodiments, the methods, compounds and composition of the invention are for addressing infections by immunodeficiency viruses (e.g. human HIV, feline FIV, bovine BIV, equine infectious anemia virus (EIAV), murine leukemia virus (MLV)), hepaciviruses (e.g. hepatitis C virus), and/or herpes viruses (e.g. herpes simplex virus 1 (HSV-1), herpes simplex virus 2 (HSV-1)).

In particular embodiments the DCIR comprises a ITIM motif ITYAEV (SEQ ID NO.15) the compound interferes directly or indirectly with a binding interaction between said ITIM motif and said intracellular modulator. For instance, the compound may interfere directly or indirectly with a binding interaction involving a Src homology-2 domain (SH2)-containing tyrosine phosphatase of the intracellular modulator. More particularly the compound may interfere directly or indirectly with phosphorylation of the tyrosine on the ITIM motif and/or interfere directly or indirectly with phosphorylation of the threonine on the ITIM motif.

In accordance with some embodiments of the invention, such compounds may include, for example, those compounds which may block phosphorylation of the tyrosine and/or blocks phosphorylation of threonine of the ITIM motif ITYAEV (SEQ ID NO. 15).

In particular embodiments the compound inhibits the activity or expression of one or more of intracellular modulator as defined herein.

In some embodiments, the compound consists of a polypeptide comprising an amino acid sequence as set forth in SEQ ID NO.2, SEQ ID NO: 11, SEQ ID NO: 12, SEQ ID NO: 15, SEQ ID NO: 16, SEQ ID NO: 17, SEQ ID NO: 21, SEQ ID NO: 22, SEQ ID NO: 26 and SEQ ID NO: 27 as defined herein. The compound may also consist of one or more peptides as defined herein and mixtures thereof.

In some embodiments, the compound consists of an antisense molecule. Preferably the antisense molecule comprises at least 10 nucleotides complementary to the coding strand of at least one of the intracellular modulator. Examples of antisense molecules include those listed in Table 1 hereinafter, homologs of these sequences having a substantial percentage of identity or similarity with the antisense molecules of Table 1, and mixtures thereof. In particular embodiments the intracellular modulator is selected from SHP-1, SHP-2, Src, Fyn, Hck, Syk, PKCα, ERK1/2 and/or p38 and the antisense molecules preferentially comprises a nucleic acid sequence selected from the group consisting of: SEQ ID NO. 30, SEQ ID NO.36, SEQ ID NO.38, SEQ ID NO.40, SEQ ID NO.42, SEQ ID NO.44, SEQ ID NO.54, SEQ ID NO.50, SEQ ID NO.58, SEQ ID NO.46, SEQ ID NO.56, SEQ ID NO.32, and SEQ ID NO.34.

Some related aspects of the present invention concerns compounds, compositions and methods for reducing human immunodeficiency virus (HIV) binding, entry and/or replication. The present invention more particularly encompasses compounds capable of modulating dendritic cell immunoreceptor (DCIR) expression and/or activity, compounds capable of modulating DCIR expression, compounds capable of modulating the interaction between HIV and DCIR and compounds capable of modulating the events triggered by HIV and DCIR interaction. Such compounds may include, for example, pharmacological inhibitors SHP-1, SHP-2, Src, Fyn, Hck, Syk, PKCα, ERK1/2 and/or p38. In a further related aspect, the compound modulates one or more events triggered by HIV and DCIR interaction.

In addition, the invention encompasses compounds, compositions and methods for preventing or reducing virus entry and/or capture into the mammalian cell by DCIR by inhibiting intracellular production and/or accumulation of free radicals in the cell. Therefore, some aspects of the invention relates to the use of free radicals inhibitors, antioxidants and/or scavengers, including but not limited to, catalase, inhibitors of nitrogen oxygen syntase, inhibitors of NADPH oxydase, and/or N-acetyl-cysteine (NAC), for the prevention or treatment of a virus infection in a mammal.

The invention further encompasses compounds, compositions and methods for preventing or treating virus infections in mammals by administering an inhibitor of apoptosis, more particularly inhibitors of apoptosis capable of reducing expression of DCIR. Examples include, but are not limited to, caspase inhibitors such as Benzyloxycarbonyl-Val-Ala-Asp (OMe) fluoromethylketone (Z-VAD-FMK), or ICE-like protease inhibitor or nuclear translocation of Apoptosis Inducing Factor (AIF) inhibitor such as N-acetyl-cysteine (NAC). Related aspects the invention concerns methods comprising administering to a subject in need a compound reducing apoptosis triggered by the intrinsic apoptotic pathway following virus infection.

D) Peptides

According to particular embodiments of the invention, the compound interfering with an intracellular modulator participating in DCIR signalling and/or the compound interfering with an intracellular signalling event triggered following a physical interaction between HIV and a dendritic cell immunoreceptor (DCIR), is a peptide.

In preferred embodiments the peptide comprises an amino acid sequence as set forth in SEQ ID NO. 2:

```
Xaa₁Xaa₂Xaa₃Xaa₄Xaa₅Xaa₆        (SEQ ID NO.: 2)
``` wherein
$Xaa_1$ is S, I, V or L;
$Xaa_2$ is any amino acid or phospho-threonine;
$Xaa_3$ is tyrosine or phospho-tyrosine;
$Xaa_4$ or $Xaa_5$ is any amino acid;
$Xaa_6$ is I, V or L;
at least one of $Xaa_2$ or $Xaa_3$ is a phosphorylated residue.

Peptides (polypeptides) of the present invention include non-naturally occurring (e.g., isolated and/or substantially purified) peptides which comprise an amino acid sequence as set forth in SEQ ID NO.2. In accordance with the present invention, the peptide is preferentially not DCIR (SEQ ID NO.1) or none of its naturally occurring isoforms. Nevertheless, the peptide of the present invention may have from 6 to 46 consecutive amino acids of DCIR (SEQ ID NO.1) and it may be overlapping with the amino acid sequence ITYAEV (SEQ ID NO.15). The 6 to 46 consecutive amino acids may correspond, for example, to the amino acid sequence of the intracellular region of DCIR (SEQ ID NO.1).

In accordance with an embodiment of the invention, the peptide comprises an amino acid sequence as set forth in SEQ ID NO.2, wherein $Xaa_2$ is a phospho-threonine and $X_2$ is a tyrosine.

In accordance with an embodiment of the invention, the peptide comprises an amino acid sequence as set forth in SEQ ID NO.2, wherein $Xaa_2$ is a threonine and $Xaa_3$ is a phospho-tyrosine.

In accordance an additional embodiment of the invention, the peptide comprises an amino acid sequence as set forth in SEQ ID NO.2, wherein $Xaa_1$ is I.

In accordance another embodiment of the invention, the peptide comprises an amino acid sequence as set forth in SEQ ID NO.2, wherein $Xaa_5$ is V.

In accordance with yet another embodiment of the invention, the peptide comprises an amino acid sequence as set forth in SEQ ID NO.2, wherein $Xaa_4$ is A.

In accordance a particular embodiment of the invention, the peptide comprises an amino acid sequence as set forth in SEQ ID NO.2, wherein $Xaa_5$ is E.

In one particular embodiment, the peptide comprises an amino acid sequence as set forth in SEQ ID NO. 15: ITYAEV (SEQ ID NO.15) wherein at least one of the threonine (T) or tyrosine (Y) residue is phosphorylated.

In other particular embodiments, the peptide comprises, and more preferably consists of any of the peptides defined in Table 2A and Table 2B, and mixtures thereof. Particular examples include:
(i) EI<u>T</u>YAEVRFKNEFKS (SEQ ID NO: 12), wherein the threonine is phosphorylated;
(ii) EIT<u>Y</u>AEVRFKNES (SEQ ID NO: 11), wherein the tyrosine is phosphorylated;
(iii) IT<u>Y</u>AEV (SEQ ID NO: 16), wherein the tyrosine is phosphorylated;
(iv) I<u>T</u>YAEV (SEQ ID NO: 17), wherein the threonine is phosphorylated;
(v) VA<u>Y</u>ETI (SEQ ID NO: 18), wherein the tyrosine is phosphorylated;
(vi) VA<u>Y</u>ETI (SEQ ID NO: 19), wherein the threonine is phosphorylated;
(vii) EIT<u>Y</u>AEVRFKN (SEQ ID NO: 21), wherein the tyrosine is phosphorylated;
(viii) EI<u>T</u>YAEVRFKN (SEQ ID NO: 22), wherein the threonine is phosphorylated;
(ix) VA<u>Y</u>ETIKNFR (SEQ ID NO: 23), wherein the tyrosine is phosphorylated;
(x) VAYE<u>T</u>IKNFR (SEQ ID NO: 24), wherein the threonine is phosphorylated;
(xi) EIT<u>Y</u>AEVRFKNEFKS (SEQ ID NO: 26), wherein the tyrosine is phosphorylated;
(xii) EI<u>T</u>YAEVRFKNEFKS (SEQ ID NO: 27), wherein the threonine is phosphorylated;
(xiii) KENFKRFVA<u>Y</u>(PO₃H2)ETIES (SEQ ID NO: 28), wherein the tyrosine is phosphorylated; and
(xiv) KENFKRFVAYE<u>T</u>IES (SEQ ID NO: 29) wherein the threonine is phosphorylated.

Peptides of the present invention may also be associated with a foreign amino acid sequence or to a compound such as a label.

As is known in the art, it may be of interest to modify the biological activity of a polypeptide by amino acid substitution, insertion or deletion. For example, modification of a polypeptide may result in an increase in the polypeptide's biological activity, may modulate its toxicity, may result in changes in bioavailability or in stability, or may modulate its immunological activity or immunological identity. Accordingly, the present invention encompasses peptide variants of the peptide defined herein, (e.g. variants of SEQ ID NOs.: 2, 11, 12, 15, 16, 17, 18, 19, 21, 22, 23, 24, 26, 27, 28, and 29 as defined herein), the variant having at least one amino acid insertion, or deletion or having at least one amino acid replaced by conservative substitution, the variant having substantially the same, or having an improved, biological activity, compared to the reference peptide. Exemplary embodiments of conservative substitutions are shown in Table 1A under the heading of "preferred substitutions". If such substitutions result in a undesired property, then more substantial changes, denominated "exemplary substitutions" in Table 1A, or as further described below in reference to amino acid classes, may be introduced and the products screened.

Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties: Group 1 (hydrophobic or aliphatic): norleucine, methionine (Met), Alanine (Ala), Valine (Val), Leucine (Leu), Isoleucine (Ile); Group 2 (neutral or hydrophilic): Cysteine (Cys), Serine (Ser), Threonine (Thr); Group 3 (acidic): Aspartic acid (Asp), Glutamic acid (Glu); Group 4 (basic): Asparagine (Asn), Glutamine (Gln), Histidine (His), Lysine (Lys), Arginine (Arg); Group 5 (residues that influence chain orientation): Glycine (Gly), Proline (Pro); and Group 6 (aromatic): Tryptophan (Trp), Tyrosine (Tyr), Phenylalanine (Phe). Non-conservative substitutions will entail exchanging a member of one of these classes for another.

Thus, in some cases, the basic amino acids Lys, Arg and His may be interchangeable; the acidic amino acids Asp and Glu may be interchangeable; the neutral polar amino acids Ser, Thr, Cys, Gln, and Asn may be interchangeable; the non-polar aliphatic amino acids Gly, Ala, Val, Ile, and Leu are interchangeable but because of size Gly and Ala are more closely related and Val, Ile and Leu are more closely related to each other, and the aromatic amino acids Phe, Trp and Tyr may be interchangeable. It should be further noted that if the polypeptides are made synthetically, substitutions by amino acids, which are not naturally encoded by DNA (non-naturally occurring or unnatural amino acid) may also be made. A non-naturally occurring amino acid is to be understood herein as an amino acid which is not naturally produced or found in a mammal. A non-naturally occurring amino acid comprises a D-amino acid, an amino acid having an acetylaminomethyl group attached to a sulfur atom of a cysteine, a pegylated amino acid, etc. The inclusion of a non-naturally occurring amino acid in a defined polypeptide sequence will therefore generate a derivative of the original polypeptide.

TABLE 1A

Amino acid substitution

| Original residue | Exemplary substitution | Exemplary conservative substitution |
|---|---|---|
| Ala (A) | Val, Leu, Ile, Gly, Ser | Val |
| Arg (R) | Lys, Gln, Asn | Lys |
| Asn (N) | Gln, His, Lys, Arg, Asp | Gln |
| Asp (D) | Glu, Asn | Glu |
| Cys (C) | Ser, Ala | Ser |
| Gln (Q) | Asn; Glu | Asn |
| Glu (E) | Asp, Gln | Asp |
| Gly (G) | Ala, Pro | Ala |
| His (H) | Asn, Gln, Lys, Arg, | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile, Tyr | Leu |
| Phe (F) | Met, Leu, Val, Ile, Ala, Tyr | Tyr, Leu |
| Pro (P) | Ala, Gly | Ala, Gly |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, norleucine | Leu |

Polypeptides of the present invention may comprise for example, those containing amino acid sequences modified either by natural processes, such as posttranslational processing or by chemical modification techniques which are known in the art. Modifications may occur anywhere in a polypeptide including the polypeptide backbone, the amino acid side chains and the amino- or carboxy-terminus. A given polypeptide may contain many types of modifications. It is to be understood herein that more than one modification to the polypeptides described herein are encompassed by the present invention to the extent that the biological activity is substantially similar to the original polypeptide. Polypeptide modification may comprise, for example, amino acid insertion, deletion and substitution (i.e., replacement), either conservative or non-conservative (e.g., D-amino acids) in the polypeptide sequence where such changes do not substantially alter the overall biological activity of the polypeptide.

Generally, the degree of similarity and identity between two peptides or protein is determined herein using the Blast2 sequence program (Tatiana A. Tatusova, Thomas L. Madden (1999), "Blast 2 sequences—a new tool for comparing protein and nucleotide sequences", FEMS Microbiol Lett. 174: 247-250) using default settings, i.e., blastp program, BLOSUM62 matrix (open gap 11 and extension gap penalty 1; gapx dropoff 50, expect 10.0, word size 3) and activated filters.

Percent identity is therefore indicative of amino acids which are identical in comparison with the original peptide and which may occupy the same or similar position.

Percent similarity is indicative of amino acids which are identical and those which are replaced with conservative amino acid substitution in comparison with the original peptide at the same or similar position.

Variants of the present invention therefore comprise those which may have at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with an original sequence or a portion of an original sequence.

Further exemplary embodiments of variants are those having at least 85% sequence identity to a sequence described herein and 85%, 86%, 87%, 88%, 89%, 90%, 91%, 92%, 93%, 94%, 95%, 96%, 97%, 98%, 99% or 100% sequence similarity with an original sequence or a portion of an original sequence.

Other exemplary embodiments of variants are those having at least 90% sequence identity to a sequence described herein and 90%, 91%, 92%, 93%, 94%, 95%, 96%, 97%, 98%, 99% or 100% sequence similarity with an original sequence or a portion of an original sequence.

Additional exemplary embodiments of variants are those having at least 95% sequence identity to a sequence described herein and 95%, 96%, 97%, 98%, 99% or 100% sequence similarity with an original sequence or a portion of an original sequence.

Yet additional exemplary embodiments of variants are those having at least 97% sequence identity to a sequence described herein and 97%, 98%, 99% or 100% sequence similarity with an original sequence or a portion of an original sequence.

For a purpose of concision Table 1B hereinafter illustrates exemplary embodiments of individual variants encompassed by the present invention and comprising the specified % sequence identity and % sequence similarity. Each "X" is to be construed as defining a given variant.

For some embodiments the compound for use according to the methods described herein (e.g. methods for interfering with an intracellular modulator participating in DCIR signalling; methods for the prevention or treatment of virus infections) is a polypeptide. Therefore, an additional aspect of the invention concerns methods as defined herein, the method comprising contacting the mammalian cell (e.g. introducing into an infected cell or a cell susceptible to virus infection) with a polypeptide of the invention.

Generally, an important factor in the administration of polypeptides is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins, lipids and other compounds, which have the ability to translocate polypeptides across a cell membrane, have been described. For example, "membrane translocation polypeptides" have amphiphilic or hydrophobic amino acid subsequences that have the ability to act as membrane-translocating carriers. A polypeptide according to the invention can be linked to suitable peptide sequences for facilitating its uptake into cells. Other suitable chemical moieties that provide enhanced cellular uptake can also be linked, either covalently or non-covalently, the polypeptides of the invention. Other suitable having the ability to transport polypeptides across cell membranes may also be used as illustrated in FIG. 19

A suitable polypeptide can also be introduced into an animal cell, preferably a mammalian cell, via liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell. In certain embodiments, it may be desirable to target a liposome using targeting moieties that are specific to a particular cell type, tissue, and the like. Targeting of liposomes using a variety of targeting moieties (e.g., ligands, receptors, and monoclonal antibodies) has been previously described.

intracellular modulator defined herein (e.g. SHP-1, SHP-2, Src, Fyn, Hck, Syk, PKCα, ERK1/2 and p38).

The present invention encompasses polynucleotides comprising modified nucleotide/nucleoside including, without limitation, phosphorothioate-, methylphosphonate- or morpholino-modification of one or more nucleotide/nucleoside and any other suitable modification which could increase the stability and/or half-life of the polynucleotide.

In some embodiment the polynucleotide is an antisense molecule inhibiting the expression of at least one of the intracellular modulator. More preferably the antisense molecule is adapted for administration to a human subject.

Delivery of polynucleotides, including antisense molecules, according to the invention may be carried using means for introducing polynucleotides into a cell that are well known in the art. Any suitable procedure for introducing foreign nucleotide sequences into host cells can be used. Possible techniques include, but are not limited to, the use of calcium phosphate transfection, DEAE-dextran-mediated

TABLE 1B

Percent (%) sequence identity

| | | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 |
|---|---|---|---|---|---|---|---|---|---|---|---|---|---|---|---|---|---|---|---|---|---|---|---|---|---|---|---|
| Percent (%) sequence similarity | 75 | X | | | | | | | | | | | | | | | | | | | | | | | | | |
| | 76 | X | X | | | | | | | | | | | | | | | | | | | | | | | | |
| | 77 | X | X | X | | | | | | | | | | | | | | | | | | | | | | | |
| | 78 | X | X | X | X | | | | | | | | | | | | | | | | | | | | | | |
| | 79 | X | X | X | X | X | | | | | | | | | | | | | | | | | | | | | |
| | 80 | X | X | X | X | X | X | | | | | | | | | | | | | | | | | | | | |
| | 81 | X | X | X | X | X | X | X | | | | | | | | | | | | | | | | | | | |
| | 82 | X | X | X | X | X | X | X | X | | | | | | | | | | | | | | | | | | |
| | 83 | X | X | X | X | X | X | X | X | X | | | | | | | | | | | | | | | | | |
| | 84 | X | X | X | X | X | X | X | X | X | X | | | | | | | | | | | | | | | | |
| | 85 | X | X | X | X | X | X | X | X | X | X | X | | | | | | | | | | | | | | | |
| | 86 | X | X | X | XX | X | X | X | X | X | X | X | X | | | | | | | | | | | | | | |
| | 87 | X | X | X | X | X | X | X | X | X | X | X | X | X | | | | | | | | | | | | | |
| | 88 | X | X | X | X | X | X | X | X | X | X | X | X | X | X | | | | | | | | | | | | |
| | 89 | X | X | X | X | X | X | X | X | X | X | X | X | X | X | X | | | | | | | | | | | |
| | 90 | X | X | X | X | X | X | X | X | X | X | X | X | X | X | X | X | | | | | | | | | | |
| | 91 | X | X | X | X | X | X | X | X | X | X | X | X | X | X | X | X | X | | | | | | | | | |
| | 92 | X | X | X | X | X | X | X | X | X | X | X | X | X | X | X | X | X | X | | | | | | | | |
| | 93 | X | X | X | X | X | X | X | X | X | X | X | X | X | X | X | X | X | X | X | | | | | | | |
| | 94 | X | X | X | X | X | X | X | X | X | X | X | X | X | X | X | X | X | X | X | X | | | | | | |
| | 95 | X | X | X | X | X | X | X | X | X | X | X | X | X | X | X | X | X | X | X | X | X | | | | | |
| | 96 | X | X | X | X | X | X | X | X | X | X | X | X | X | X | X | X | X | X | X | X | X | X | | | | |
| | 97 | X | X | X | X | X | X | X | X | X | X | X | X | X | X | X | X | X | X | X | X | X | X | X | | | |
| | 98 | X | X | X | X | X | X | X | X | X | X | X | X | X | X | X | X | X | X | X | X | X | X | X | X | | |
| | 99 | X | X | X | X | X | X | X | X | X | X | X | X | X | X | X | X | X | X | X | X | X | X | X | X | X | |
| | 100 | X | X | X | X | X | X | X | X | X | X | X | X | X | X | X | X | X | X | X | X | X | X | X | X | X | X |

E) Polynucleotides

According to particular embodiments of the invention, the compound interfering with an intracellular modulator participating in DCIR signalling and/or the compound interfering with an intracellular signalling event triggered following a physical interaction between HIV and a dendritic cell immunoreceptor (DCIR), is a polynucleotide. Additional aspects of the invention also concerns polynucleotides comprising at least 10 nucleotides complementary to the coding strand of one or more of the intracellular modulator defined herein.

Polynucleotides in accordance with the invention include, but are not limited to, antisense molecules, siRNA, ribozymes etc. and the like. In preferred embodiments, the polynucleotides comprises at least ten (10) nucleotides (e.g. about 10, 15, 20, 25, 30, 35, 40, 45, 50 or more nucleotides) and these at least ten (10) nucleotides are complementary to the coding strand (e.g., complementary to nucleotides 10 to 30, or 10 to 40; or 15 to 30, or from 22 to 52, etc.) of one or more of the transfection, polybrene, protoplast fusion, electroporation, lipid-mediated delivery (e.g., liposomes), microinjection, particle bombardment, introduction of naked DNA, plasmid vectors, viral vectors (both episomal and integrative) and any of the other well known methods for introducing cloned genomic DNA, cDNA, synthetic DNA or other foreign genetic material into a host cell.

Conventional viral and non-viral based gene transfer methods could also possibly be used to introduce nucleic acids into mammalian cells or target tissues. Methods of non-viral delivery of nucleic acids include lipofection, microinjection, ballistics, virosomes, liposomes, immunoliposomes, polycation or lipid:nucleic acid conjugates, naked DNA, artificial virions, and agent-enhanced uptake of DNA.

F) Pharmaceutical Compositions and Formulations

A related aspect of the invention concerns pharmaceutical compositions comprising one or more of the compounds of the invention described herein. As indicated hereinbefore, the compounds of the invention may be useful in: (i) inhibiting dendritic cell immunoreceptor (DCIR) signalling in a mammalian cell, (ii) reducing binding to, entry into and/or replication of a virus within the mammalian cell; and (iii) prevention or treatment of a human immunodeficiency virus (HIV) infection.

As used herein, the term "pharmaceutical composition" refers to the presence of at least one compound of the invention as defined herein and at least one pharmaceutically acceptable carrier or vehicle. Particular examples of representative compounds of the invention include peptides comprising SEQ ID NO. 2, 11, 12, 15, 16, 17, 18, 19, 21, 22, 23, 24, 26, 27, 28, or 29 as defined herein as defined herein, and antisense molecules comprising SEQ ID NO. 30, SEQ ID NO.36, SEQ ID NO.38, SEQ ID NO.40, SEQ ID NO.42, SEQ ID NO.44, SEQ ID NO.54, SEQ ID NO.50, SEQ ID NO.58, SEQ ID NO.46, SEQ ID NO.56, SEQ ID NO.32, or SEQ ID NO.34. The pharmaceutical composition of the present invention are formulated by methods known to those skilled in the art. Suitable compositions may include solids, liquids, oils, emulsions, gels, aerosols, inhalants, capsules, pills, patches and suppositories.

"Pharmaceutically acceptable vehicle" refers to a diluent, adjuvant, excipient, or carrier with which a compound is administered. The term "pharmaceutically acceptable" refers to drugs, medicaments, inert ingredients etc., which are suitable for use in contact with the tissues of humans and lower animals without undue toxicity, incompatibility, instability, irritation, allergic response, and the like, commensurate with a reasonable benefit/risk ratio. It preferably refers to a compound or composition that is approved or approvable by a regulatory agency of the Federal or State government or listed in the U.S. Pharmacopoeia or other generally recognized pharmacopoeia for use in animals and more particularly in humans. The pharmaceutically acceptable vehicle can be a solvent or dispersion medium containing, for example, water, ethanol, polyol (for example, glycerol, propylene glycol, and liquid polyethylene glycol), suitable mixtures thereof, and vegetable oils. Additional examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Prevention of the action of microorganisms can be achieved by addition of antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of injectable compositions can be brought about by including in the composition an agent which delays absorption, for example, aluminum monostearate or gelatin.

In preferred embodiments, administering one or more of the compounds of the invention to a subject comprises administering a therapeutically effective amount. As used herein, the term "therapeutically effective amount" means the amount of compound that, when administered to a subject for treating or preventing a particular disorder, disease or condition, is sufficient to effect such treatment or prevention of that disorder, disease or condition. Dosages and therapeutically effective amounts may vary for example, depending upon a variety of factors including the activity of the specific agent employed, the age, body weight, general health, gender, and diet of the subject, the time of administration, the route of administration, the rate of excretion, and any drug combination, if applicable, the effect which the practitioner desires the compound to have upon the subject and the properties of the compounds (e.g. bioavailability, stability, potency, toxicity, etc), and the particular disorder(s) the subject is suffering from. In addition, the therapeutically effective amount may depend on the subject's blood parameters (e.g. lipid profile, insulin levels, glycemia), the severity of the disease state, organ function, or underlying disease or complications. Such appropriate doses may be determined using any available assays including the assays described herein. When one or more of the compounds of the invention is to be administered to humans, a physician may for example, prescribe a relatively low dose at first, subsequently increasing the dose until an appropriate response is obtained.

G) Screening Assays

The invention encompasses assays and related methods for identifying compounds which have the ability to impair or even to interfere dendritic cell immunoreceptor (DCIR) activity and signaling events, including assays and methods particularly for identifying compounds capable of reducing human immunodeficiency virus (HIV) binding, entry and/or replication.

Those skilled in the art understand that once an interaction between two binding partners is discovered, several types of assays (e.g., cell based and/or biochemical assays) may be carried out to identify compounds capable of impairing or inhibiting this interaction. Several libraries of molecules are commercially available and may be used to identify putative inhibitors.

In an exemplary embodiment of the invention, a suitable compound may be identified by a method which may comprise contacting a test compound with a cell expressing DCIR and measuring DCIR activity and signalling events. In one embodiment, one can measure ability of a test compound to interfere with the activity of an intracellular modulator participating in DCIR signalling, and more particularly at least one of Syk, PKC-α, Hck, Fyn, Src, ERK 1/2, p38, SHP-1, and SHP-2. A diminution of DCIR activity and/or of one or more related signalling events may thus be indicative of a compound having a desired activity and compound utility in the prevention or treatment of virus infections in a mammal. Test compounds include, but are not limited to, antibodies, antigen binding fragment thereof, proteins, peptides, a small molecules etc.

In a particular aspect the present invention relates to a method for identifying a compound that reduces HIV infection of DCIR expressing cells or that reduces HIV propagation by DCIR expressing cells. The method comprises contacting a test compound with a cell expressing DCIR and measuring HIV replication (e.g., amount of virus produced) or HIV propagation (e.g. infection of or transmission to CD4$^+$ T-cells). A diminution of HIV replication or propagation in the presence of the test compound may be indicative of a compound capable of reducing HIV infection of DCIR expressing cells or HIV dissemination by DCIR expressing cells. Conceivably, the method may also be carried out using recombinant proteins, e.g., DCIR or recombinant DCIR with a preparation containing HIV or HIV-like particles. The cell used in the screening method may preferably carry a CD4 receptor. The cell may also preferably carry suitable HIV co-receptor(s).

In accordance with an embodiment of the invention, the DCIR expressing cell may be a CD4-positive cell. In accordance with a further embodiment of the invention, the DCIR expressing cell may be a CCR5-positive cell. In accordance with yet a further embodiment of the invention, the DCIR expressing cell may be a CXCR4-positive cell. As described herein dendritic cells are suitable for screening for HIV inhibitors. The dendritic cell may be an immature dendritic cell.

Exemplary compounds that may be used in such screening methods includes without limitation, interfering RNAs, antisense RNAs, ribozymes, deoxyribozymes, proteins or peptides, antibodies or antibody fragments or small molecules.

EXAMPLES

The Examples set forth hereinafter provide results showing that HIV-1 induces DCIR expression in CD4$^+$ T cells and results showing that DCIR-mediated enhancement of HIV-1 requires the ITIM-associated signal transduction pathway. Also provided are exemplary compounds according to the invention and methods for assaying the same invention for in vitro and ex vivo efficacy.

Materials and Methods

Reagents.

IL-4 was purchased from R&D systems (Minneapolis, USA), whereas granulocyte macrophage-colony stimulating factor (GM-CSF) was purchased from Genscript (Piscataway, USA). The culture medium consisted of RPMI-1640 supplemented with 10% foetal bovine serum (FBS), penicillin G (100 U/ml), streptomycin (100 U/ml), glutamine (2 mM), which were all purchased from Wisent (St-Bruno, Canada) and of Primocine™ that was bought from Amaxa Biosystems (Gaithersburg, USA). The culture medium for 293T cells was made of Dulbecco's modified Eagle's medium (DMEM) (Invitrogen, Burlington, Canada) supplemented with 10% FBS, penicillin G (100 U/ml), streptomycin (100 U/ml), and glutamine (2 mM).

SHP-1 inhibitor SSG was provided by Glaxo-Wellcome Ltd (Oakville, Canada). Syk inhibitor piceatannol, Src inhibitor PP2, protein kinase C (PKC) inhibitor Gö6976, PKA inhibitor H89, p38 inhibitor SB203580, MEK1 inhibitor PD98059, BTK inhibitor LFM-A13 and phosphatidylinositol 3-kinase (PI3K) inhibitor Wortmannin were all purchased from Calbiochem (San Diego, USA).

Antibodies.

Phycoerithrin (PE)-labeled anti-DCIR monoclonal antibodies (clone 216110) and corresponding isotypes were purchased from R&D systems (Minneapolis, USA). Antibodies against Syk was purchased from Upstate Biotechnology (Lake Placid, USA); SHP-1 (C-19), SHP-2 (C-18), Fgr (N-47), Lyn (44), Lck (3A5), Hck (N-30), PKC-α (C-20) and actin (1-19) antibodies were obtained from Santa Cruz (Santa Cruz, USA); while antibodies recognizing p38, Erk1/2 (137F5) and Src were purchased from Cell signalling (New England Biolabs, Pickering, Canada). A Fyn antibody was a kind gift from Paul H. Naccache (Centre Hospitalier Universitaire de Québec-CHUL). Antibodies specific for PKCα were purchased from BD Biosciences (Mississauga, Canada) and those directed against PKC-α were obtained from Signalway Antibody (Tearland, USA).

Cells.

Human embryonic kidney 293T cells were cultured in DMEM supplemented with 10% FBS. The Raji-CD4 cell line is a B cell line carrying the Epstein-Barr virus that has been rendered susceptible to HIV-1 infection by stable transfection with a cDNA encoding human CD4. These cells were cultured in RPMI-1640 medium supplemented with 10% FBS along with 1 mg/mL of the selective agent G418 (GIBCO-BRL, Gaithersburg, USA). Raji-CD4 cells stably expressing DCIR were obtained following retroviral transduction. In brief, wild type cDNA encoding for human DCIR was subcloned in the dicistronic retroviral vector MSCV-IRES-eGFP. Next, 293T cells were cotransfected by the CalPhos mammalian transfection kit with the vector MSCV-DCIR-IRES-eGFP or MSCV-IRES-eGFP (used as a control), SV-ψ$^-$-env$^-$-MLV (a gag-pol-encoding vector) and HCMV-G (VSVG) (codes for the vesicular stomatitis virus glycoprotein). The virus-containing medium was harvested 48 hours later, passed through a 0.22-μM cellulose acetate syringe filter, ultracentrifuged and stored at −80° C. Transduction of Raji-CD4 cells was carried out by mixing cells with serially diluted virus supernatants in culture medium supplemented with 3% serum. After 24 hours of culture with viral supernatants, culture medium supplemented 10% serum was added. After 24 additional hours, cells were washed extensively and those expressing high levels of DCIR were isolated by FACS based on eGFP expression. DCIR was monitored by FACS after obtaining enough cells for the assays. Primary human DCs were generated from purified human monocytes (i.e. CD14$^+$ cells). Briefly, peripheral blood was obtained from healthy donors and peripheral blood mononuclear cells (PBMCs) were prepared by centrifugation on a Ficoll-Hypaque density gradient. Next, CD14$^+$ cells were isolated from fresh PBMCs by using a monocyte-positive selection kit according to the manufacturer's instructions (MACS CD14 microbeads, STEMCell Technologies, Vancouver, Canada)[27]. Briefly, CD14$^+$ cells were cultured in six-well plates at a density of 10$^6$ cells/ml in 3 ml of RPMI-1640 medium supplemented with 10% FBS. To generate immature monocyte-derived dendritic cells (IM-MDDCs), purified monocytes were cultured in complete culture medium that was supplemented every other day with GM-CSF (1,000 U/ml) and IL-4 (200 U/ml) for 7 days. Experiments were performed with cell preparations that contained a minimal amount of contaminants (i.e. DC: purity >95%)[27].

Flow Cytometric Analysis.

Cell surface expression of DCIR was monitored by flow cytometric analysis (Epics ELITE ESP, Coulter Electronics, Burlington, Canada). Cells (1×10$^6$ cells) were incubated for 30 min with a pool of human serum to block the unspecific binding. After washing, the cells were incubated with PE-labeled anti-DCIR (0.25 μg) for 45 min at 4° C. and then washed twice with PBS and 0.5% BSA. Non-specific staining was determined by using an isotype-matched irrelevant control antibody. After two final washes with PBS, cells were fixed in 2% paraformaldehyde for 30 min and analyzed.

Production of Viral Stocks for Binding/Entry and Infection Assays.

Virions were produced upon transient transfection of human embryonic kidney 293T cells as previously described[31]. The HIV-1 infectious molecular clones used in this study include NL4-3 (provided by the AIDS Repository Reagent Program, Germantown, USA), which was used in assays with parental Raji-CD4 cells (DCIR-negative) and Raji-CD4-DCIR transfectants and NL4-3balenv (provided by R. Pomerantz, Thomas Jefferson University, Philadelphia, USA)[32], which was used in assays with DCs. The pNL4-3balenv vector was generated by replacing the env gene of the T-tropic HIV-1 strain, NL4-3, with that of the macrophage-tropic HIV-1 Bal strain, thus resulting in an infectious molecular clone with macrophage-tropic properties. The virus-containing supernatants were filtered through a 0.22 μm cellulose acetate syringe filter, ultracentrifuged and normalized for virion content using an in-house sensitive double-antibody sandwich enzyme-linked immunosorbent assay (ELISA) specific for the viral p24 protein[33]. Preparations of NL4-3 were produced also by infecting Raji-CD4 cells. Briefly, cells ($5 \times 10^6$ cells) were incubated with NL4-3 (at a ratio of 10 ng of p24 per $1 \times 10^5$ cells) for 2 hours at 37° C. Cells were then washed extensively to eliminate non-internalized virions and maintained in culture for 6 days. Virions were purified and quantified as described above.

Virus Binding/Entry and Infection Assays in Raji-CD4-DCIR Cells.

Where indicated, parental Raji-CD4 cells (DCIR-negative) or Raji-CD4-DCIR transfectants ($1 \times 10^6$) were pretreated with the indicated amount of a pharmacological inhibitor for 10 min or transfected with sense or antisense oligonucleotides as described below. Cells were then pulsed with NL4-3 (100 ng of p24) for 60 min at 37° C. Next the virus-cell mixture was washed 3 times with PBS to remove unbound virus and resuspended in PBS containing 1% BSA. To assess binding/entry, the p24 content was determined by our in-house ELISA assay[33].

Figure 5:
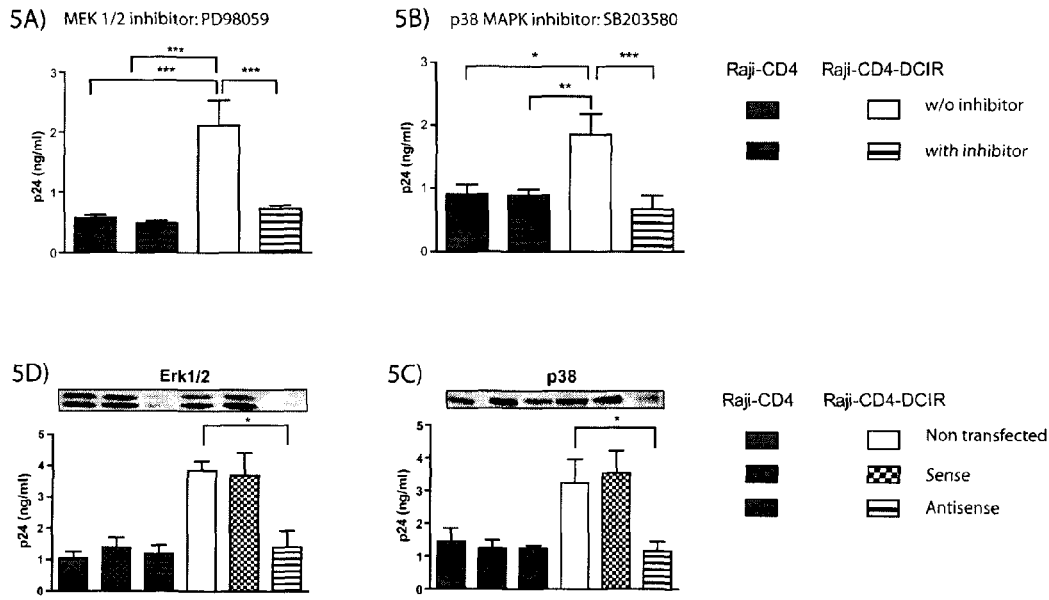
FIG. 5 shows DCIR-mediated enhancing effect on HIV-1 binding/entry involves ERK1/2 and p38. Experimental procedures used here are similar to the ones described in FIG. 2 except that the following inhibitors and oligonucleotides were tested: ERK1/2 inhibitor PD98059 (20 nM) (panel A), p38 inhibitor SB203580 (2 μM) (panel B), and oligonucleotides specific for ERK1/2 (panel C) and p38 (panel D).

For the infection assay shown on FIGS. 1 and 5, Raji-CD4 and Raji-CD4-DCIR ($1 \times 10^6$ cells) were exposed to NL4-3 (100 ng of p24) for 2 hours at 37° C. After three washes with PBS to remove excess virus, cells were maintained in culture for up to 9 days. Cell-free culture supernatants were collected at the indicated time points and assayed for p24 content.

For the infection assay performed before measuring Tat mRNA, Raji-CD4 and Raji-CD4-DCIR cells were treated with the indicated inhibitor or transfected with the indicated oligonucleotide (as described below). Cells were then pulsed with NL4-3 during 24 hours. Next, the RNA of the cells was isolated with the Illustra™ RNAspin Mini Isolation Kit (GE Healthcare Life Sciences). The expression level of Tat mRNA was measured by real-time PCR, as described below.

Electrophoresis and Western Blotting.

Raji-CD4 and Raji-CD4-DCIR cells ($1 \times 10^6$ cells) were either left untreated or treated with sense and antisense oligonucleotides. The equivalent of $2 \times 10^4$ cells was transferred into 2x sample buffer[34]. Samples were boiled for 10 min and kept at $-20°$ C. until subjected to a western blot analysis. In brief, samples were loaded onto SDS/PAGE 10%. Proteins were then transferred to Immobilon™ PVDF membranes (Millipore Corporation, Bedford, USA). Immunoblotting were performed with antibodies describe previously depending of oligonucleotide transfected. To measure the amount of protein loaded in the gel, the membrane was stripped again and immunoblotted with anti-actin (dilution 1:5000) for 1 hour at room temperature. Proteins were detected with an enhanced chemiluminescence reagent (Pierce) followed by exposure to Kodak films.

Gene Silencing of Different Signalling Proteins with Sense and Antisense Oligonucleotides.

Raji-CD4 and Raji-CD4-DCIR cells ($1 \times 10^6$ cells) were washed with OptiMEM (Invitrogen Life Technologies) without serum and antibiotics. The phosphorothioate oligodeoxynucleotides (Listed in Table 1) (Invitrogen Life Technologies) were transfected at a final concentration of 10 µM/well[35] using Oligofectamine according to the manufacturer's instructions (Invitrogen Life Technologies). Silencing efficiency was monitored by western blot analysis.

Real-Time PCR.

Expression levels of TAT splice transcripts were determined using a Rotor-Gene™ system (Corbett Life Science). Total RNA ($1 \times 10^6$ cells) was isolated using an RNA extraction kit (GE). After elution, the amount and quality of RNA was assessed by measuring the absorbance at 260 and 280 nm. RNA was reverse-transcribed using Superscript® III Reverse Transcriptase (Invitrogen). We then proceeded to qRT-PCR quantification of transcripts by using TaqMan™ Universal PCR MaterMix system from Applied Biosystems with primers designed for TAT splice (TAT splice-F [GAAG-CATCCAGGAAGTCAGC] (SEQ ID NO: 4), TAT splice-R [CTATTCCTTCGGGCCTGTC] (SEQ ID NO: 5), 18S-F [TAGAGGGACAAGTGGCGTTC] (SEQ ID NO: 6) and 18S-R [CGCTGAGCCAGTCAGTGT] (SEQ ID NO: 7)). Normalization on 18S mRNA levels was performed to obtain final expression values. A standard curve was drawn for each gene of interest using serial dilutions of pooled RNA from all samples. The sequences for the probes are: for TAT splice 5' d FAM-TATCAAAGCAACCCACCCACCTCC-BHq-1 3' (SEQ ID NO: 8), and for 18S 5' d FAM-AACAGGTCTGT-GATGCCCTT-BHQ-1 3' (SEQ ID NO: 9). Two microliters of cDNA was used in each reaction. Primers were used at 5 µM in the reaction and probes at 2 µM.

ITIM Peptides Transfection in IM-MDDCs.

The following short competitive peptides were used in our study: non-phosphorylated ITIM (TAMRA-EITYAEVR-FKNEFKS-OH; SEQ ID NO: 10), ITIM phosphorylated on tyrosine (TAMRA-EITY($PO_3H_2$)AEVRFKNES-OH; SEQ ID NO: 11) or threonine residue (TAMRA-EIT($PO_3H_2$)YAE-VRFKNEFKS-OH; (SEQ ID NO: 12), and a control peptide (TAMRA-KENFKRFVAYETIES-OH; SEQ ID NO: 13). The listed peptides were introduced into IM-MDDCs ($1 \times 10^6$ cells) with the Pro-Ject™ transfection system (Pierce Biotechnology). Complexes were formed by incubating 100 µg of ITIM peptides with 10 µl of the Pro-Ject™ reagent in a total volume of 100 µl of PBS. As all peptides were labeled with TAMRA, the transfection efficiency was controlled by FACS analysis.

HIV-1 Binding and Virus Infection Assays.

For assessing binding/entry, IM-MDDCs ($3 \times 10^5$ cells in a final volume of 300 µl) transfected with one of the ITIM peptides were exposed to NL4-3balenv (30 ng of p24) for 60 min at 37° C. After 3 washes with PBS, cells were resuspended in PBS containing 1% BSA. The p24 content was determined by ELISA. As for susceptibility of IM-MDDCs to HIV-1 infection, it was assessed by initially exposing $3 \times 10^5$ cells to NL4-3balenv (30 ng) for 2 hours at 37° C. After 3 washes with PBS, cells were maintained in complete RPMI-1640 culture medium supplemented with GM-CSF and IL-4 in 96-well plates in a final volume of 200 µl. Every 3 days and for a period lasting 9 days, half of the medium was removed and kept frozen at $-20°$ C. until assayed. Virus production was estimated by measuring p24 levels in culture supernatants by ELISA, as described above.

Statistical Analysis:

Statistical analyses were carried out according to the methods outlined in Zar[36] and Sokal and Rohlf[37]. Means were compared using Student's t test, or a single-factor ANOVA followed by Dunnett's multiple comparison when more than two means were considered. P values of less than 0.05 were deemed statistically significant. Calculations were performed with the GraphPad Prism™ software.

Example 1

The Transduced Raji-CD4-DCIR Cell Line Expresses DCIR and Allows HIV-1 Binding/Entry and Infection To study the impact of DCIR signalling in the context of acute infection with HIV-1, and also to limit the contribution of other lectins to these processes, we used a cell line stably-transfected with DCIR. We selected Raji-CD4 cells as previous studies have utilized them as an experimental model system to study the role of DC-SIGN in HIV-1 capture and transfer processes[30, 38]. Briefly, Raji-CD4 cells were transduced with a retroviral vector expressing the human c-type lectin DCIR. To confirm that the stably transfected cell line, named Raji-CD4-DCIR, expressed DCIR, flow cytometry analysis was performed and the result shows that a significant proportion of such transduced cells are positive for DCIR after several cell passages (FIG. 1A). Furthermore, we verified that expression of CD4, the HIV-1 primary receptor leading to fusion and cis infection, was the same for both Raji-CD4 and Raji-CD4-DCIR cell lines (data not shown). Importantly, we also verified that the DCIR expressed on the cell line was able to play its functional role with regard to virus binding/entry and infection[18]. Results of virus binding/entry and infection assays are illustrated in FIGS. 1B and 1C, respectively. These data show that the Raji-CD4-DCIR cell line binds more virus and that, consequently, infection is amplified in these cells in comparison with the parental Raji-CD4 cells. As we validated the model, these cells were used for our subsequent studies.

Example 2

Importance of Kinases and Phosphatases in Signalling Mediated by DCIR in HIV-1 Binding/Entry and Infection Tyrosine Phosphatases SHP-1 and SHP-2 are Involved in DCIR Signalling Induced by HIV-1.

Figure 2:
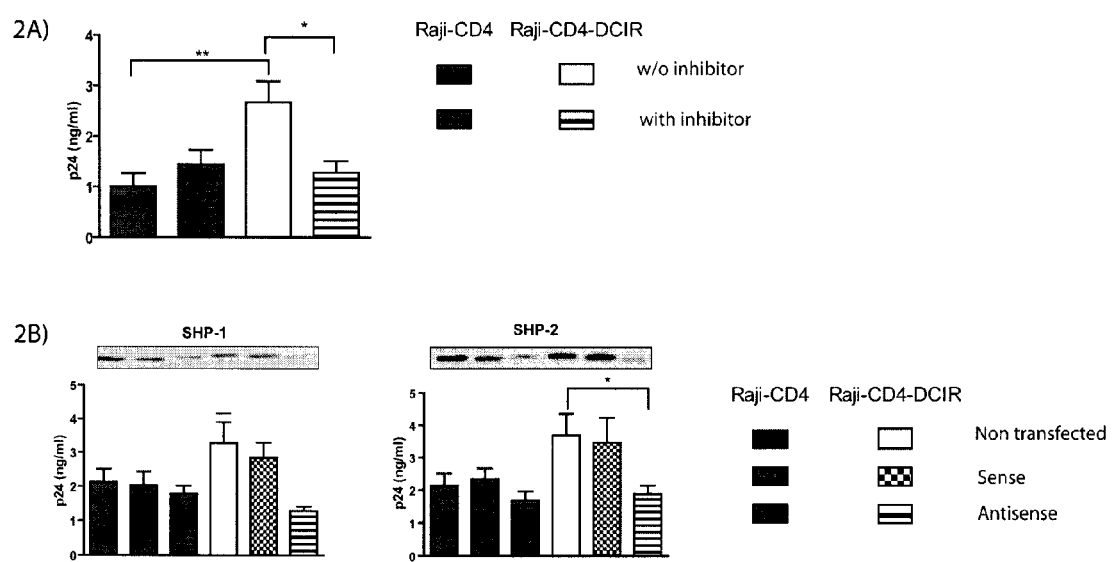
FIG. 2 shows DCIR-mediated enhancing effect on HIV-1 binding/entry involves SHP-1 and SHP-2.

As stated previously, following engagement of DCIR, phosphorylation of a tyrosine occurs on its cytoplasmic tail. It has been demonstrated that DCIR then recruits via its ITIM motif tyrosine phosphatases SHP-1 and SHP-2 but not SHIP[26]. Therefore, to evaluate the involvement of tyrosine phosphatases in DCIR signalling after HIV-1 binding, we used sodium stibogluconate (SSG), a potent in vitro inhibitor of protein tyrosine phosphatases (PTPases) such as SHP-1, SHP-2 and PTP-1B[39]. Raji-CD4-DCIR cells were pretreated with SSG for 10 min before pulsing with X4-tropic HIV-1 strain NL4-3. This treatment decreases HIV-1 binding/entry in DCIR-expressing cells, while it has no similar effect in Raji-CD4 cells (FIG. 2A).

To determine more specifically which PTPases are implicated in the signal transduced by DCIR after HIV-1 binding, we used specific antisense oligonucleotides directed against SHP-1 and SHP-2 DNA. All antisense oligonucleotides used herein are listed in Table 1. Following transfection, the involvement of SHP-1 and -2 was evaluated by a p24 test and we observed a significant decrease as shown in FIG. 2B. It must be noted that western blot (inserts in FIG. 2B) and an actin-like control (data not shown) were performed systematically in all antisense oligonucleotide assays presented in this work. These results suggest that SHP-1 and SHP-2 are involved in the signalling induced by DCIR after HIV-1 binding.

Example 3

Tyrosine Kinase Families Src and Syk are Involved in the HIV-1-Mediated DCIR Signalosome Tyrosine phosphatases SHP-1 and SHP-2 are recruited to the phosphorylated ITIM domain of DCIR, but nothing is known about TKs involved in the phosphorylation of this region[26]. We thus next assessed whether tyrosine kinase families Src, Tec and Syk were responsible for this process.

Among several non-receptor tyrosine kinase (NRTK) families, Src kinases, by their myristoylation domain, and TKs recruited to the cell membrane are the most susceptible signal transducers to initiate a tyrosine phosphorylation event following HIV-1 ligation on DCIR. The possible involvement of Src was assessed using the specific inhibitor PP2. Data shown in FIG. 3A indicate that HIV-1 binding/entry is decreased in presence of the inhibitor. These data suggest that signalling induced by DCIR is dependent on the activity of Src kinases. In order to specify which Src(s) are involved in the DCIR signalosome, we proceeded to transfection with antisense oligonucleotides against Src, Fyn, Fgr, Lyn and Hck. The results indicate that Src, Fyn and Hck are participating to the DCIR-mediated binding/entry of HIV-1 (FIG. 3B), but Fgr and Lyn do not (data not shown).

The Tec family comprises NRTKs, among which the Bruton's tyrosine kinase (BTK) is crucial for the maturation of B lineage cells. Moreover, BTK shares a feature with the Src family kinase, namely a Src homology 3 (SH3) domain[40]. In BTK, this domain may be involved in the regulation of kinase activity in a manner different from that of Src. This kinase is fully activated upon tyrosine phosphorylation of its catalytic domain by TKs of the Src family and recruitment to the cellular membrane by PI3K[41]. We tested the possible implication of BTK in the DCIR signal transduction with an inhibitor, LFM-A13, which showed that BTK is not involved in the DCIR signalosome induced by HIV-1 (FIG. 3C).

The third family of NRTKs possibly involved in DCIR signal transduction is the Syk family. It is known that Syk acts in several endocytosis/phagocytosis-signalling pathways, especially after DC-SIGN stimulation[28, 42]. Moreover, it has been shown that Syk can be recruited by tyrosine phosphorylation of the ITAM-like motif of dectin-1 and CLEC-2[43]. We thus investigated whether DCIR ITIM motif was able to recruit Syk. Cells were first treated with the Syk inhibitor piceatannol before virus exposure. Pretreatment of Raji-CD4-DCIR cells with piceatannol significantly decreases HIV-1 binding/entry (FIG. 3D). The specificity of the piceatannol-dependent effect was confirmed by the inability of the inactive analog trans-stilbene to induce a comparable decrease in HIV-1 binding/entry (data not shown). The importance of Syk was further confirmed by using a specific antisense oligonucleotide (FIG. 3E).

Activation of Syk can regulate the activity of PI3K[44]. To investigate the role of this important cellular sensor, two selective pharmacological inhibitors of PI3K, wortmannin and LY294002, were used before pulsing cells with HIV-1. No modulation of virus binding/entry was observed with either inhibitor (FIG. 3F and data not shown). Based on these observations, we concluded that DCIR stimulation by HIV-1 is independent of PI3K activation.

Example 4

PKC-α but not PKA is Involved in DCIR Signalling Induced by HIV-1

Figure 4:
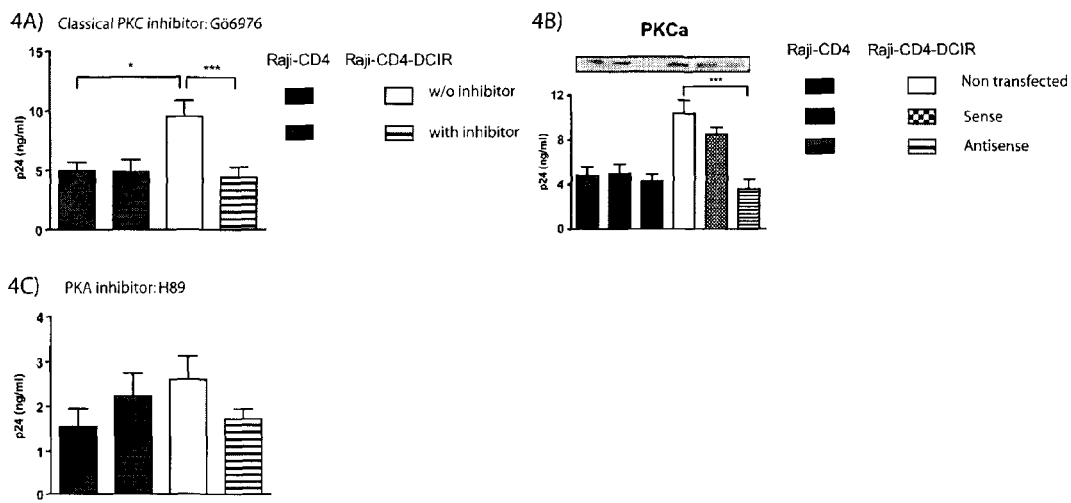
FIG. 4 shows DCIR-mediated enhancing effect on HIV-1 binding/entry involves PKC-α. Experimental procedures used here are similar to the ones described in FIG. 2 except that the following inhibitors and oligonucleotides were tested: classical PKC inhibitor Gö6976 (1 μM) (panel A), oligonucleotides specific for PKC-α (panel B), and PKA inhibitor H89 (10 μM) (panel C).

The serine and threonine kinases are also participating in several signalling cascades and in regulation of protein activity. For example, the turn off of SHP-1 is regulated by Ser591 phosphorylation, which is achieved by PKCs[45]. Moreover, Syk has been recently identified as a substrate for PKC[46]. To determine the role of classical PKCs, the inhibitor Gö6976 was used. The result illustrated on FIG. 4A show that classical PKCs play a role in DCIR-directed binding/entry of HIV-1.

However, classical PKCs comprise four distinct isoforms (i.e. α, BI, BII and γ). To discriminate between them, Raji-CD4 and Raji-CD4-DCIR cells were transfected with sense or antisense oligonucleotides specific for each one. Our findings indicate that PKC-α is the only classical PKC isoform which plays a role in the signalling induced by DCIR after virus attachment (FIG. 4B and data not shown for the three others isoforms).

PKA regulates a number of cellular processes important for immune activation and control. Activation of PKA by an increase of the intracellular level of cAMP represents one mechanism for regulating antigen receptor signalling[47]. The possible implication of this kinase in DCIR signalling was tested by using the specific inhibitor H89. PKA is not participating to the DCIR-mediated binding/entry of HIV-1 (FIG. 4C).

Example 5

ERK1/2 and p38 are Involved in DCIR Signalling Induced by HIV-1

Up to this point, we studied several kinases involved at the beginning of the signaling pathways. To complete this study, we focused on kinases intervening more downstream in the signalling cascade such as the classical mitogen-activated protein (MAP) kinases ER1/2 and p38. Cells were pretreated either with PD98059, an inhibitor of ERK1/2[48], or SB203580, an inhibitor of p38[49]. The results depicted in FIGS. 5A and 5B show that both inhibitors induce a significant decrease in HIV-1 DCIR binding/entry in Raji-CD4-DCIR cells but not in parental Raji-CD4 cells. The implication of these kinases in the DCIR signalosome, was confirmed by using specific antisense oligonucleotides (FIGS. 5C and 5D, respectively). Altogether these results suggest that the DCIR signalling pathway includes activation of ERK1/2 and p38.

Example 6

HIV-1 Replication is Increased by the Virus-Mediated Engagement of DCIR and Subsequent Signalling Through SHP-1, SHP-2, Src, Fyn, Hck, Syk, PKC-α, ERK1/2, and p38

Virus production is augmented in cells transiently expressing DCIR[18]. We therefore next verified the contribution of the signal transducers identified above in the process of virus replication. Results displayed in FIG. 6A demonstrate that signal transducers involved in DCIR-mediated HIV-1 entry/binding are also important for productive virus infection. These observations are corroborated when using antisense oligonucleotides against each protein of interest (FIG. 6B). It can be concluded that the DCIR-mediated enhancement in virus production requires SHP-1, SHP-2, Src, Fyn, Hck, Syk, PKC-α, ERK1/2 and p38.

Example 7

DCIR-Dependent Increase in Virus Replication Necessitates Tyrosine and Threonine Residues in the ITIM Motif of DCIR The ITIM motif of DCIR, ITYAEV, contains two contiguous potential sites of phosphorylation, a threonine and a tyrosine. Nevertheless, nothing is known about the importance of these amino acids in signaling by DCIR. To investigate the importance of these amino acids in the observed phenomenon, we constructed two mutants of DCIR, namely T6F, in which the threonine was replaced by a phenylalanine and Y7F, where the tyrosine was replaced by a phenylalanine. Next, using the same experimental procedure that we used for Raji-CD4-DCIR, we constructed stable cell lines expressing these two DCIR mutants. The surface expression of both forms of DCIR was evaluated by flow cytometry and we found that wild-type DCIR, DCIR-T6F and DCIR-Y7F were expressed at comparable levels (FIG. 7A).

To determine whether two amino acids is required for triggering the DCIR signaling cascade, an HIV-1 binding/entry assay was performed on these cell types and the results show a statistically weaker HIV-1 binding/entry in cells bearing threonine and tyrosine mutants (FIG. 7B, left panel). Moreover, the decrease in virus binding is reflected in HIV-1 infection (FIG. 7B, right panel).

To confirm the importance of the two amino acids in a more physiologically relevant model, an ITIM peptide, phosphorylated or not on the threonine or the tyrosine, was introduced in IM-MDDCs. The peptides were inserted in the cells with the Pro-Ject™ lipidic delivery system and, 15 min later, HIV-1 binding/entry and infection assays were performed. The presence of the peptides inside the cells was confirmed by flow cytometry (data not shown). A decrease in virus binding/entry and replication was seen in the presence of the synthetic peptides (FIG. 7C, left and right panels). This original approach permits to conclude that the phosphorylated peptides, probably compete with the intracellular ITIM domain of DCIR. Therefore, it can be proposed that the recruitment of signalling protein(s) to the phosphorylated ITIM domain of DCIR is important for HIV-1 attachment, internalisation and infection.

Example 8

DCIR is Up-Regulated in CD4$^+$ T Cells from HIV-1-Infected Persons and Following Acute Infection In Vitro DCIR has been detected in CD4$^+$ T cells originating from patients with active RA, a chronic disease characterized by a state of persistent inflammation and immune activation. Because a systemic inflammatory disorder and immune hyperactivation represent also key features of the HIV-1 infection, we first assessed DCIR expression in CD4$^+$ T cells isolated from infected individuals. To this end, the level of ex vivo DCIR expression was evaluated by flow cytometry in peripheral blood CD4$^+$ T cells from two HIV-1-infected aviremic/treated patients. Results depicted in FIG. 9A clearly indicate that DCIR is expressed in this cell subset in the context of a natural infection as opposed to what is seen in cells from uninfected healthy donors. Flow cytometry analyses were also performed on circulating CD4$^+$ T cells from additional seropositive individuals but who were this time viremic and treatment-naive. Again an up-regulation of DCIR expression was detected in such samples (FIG. 9B), which supports the concept that HIV-1 infection promotes expression of this C-type lectin receptor on the surface of circulating CD4$^+$ T cells. A cell activation marker was also monitored as well (i.e. HLA-DR) and a positive correlation was found between DCIR and HLA-DR since both cell surface constituents were found to be increased in CD4$^+$ T cells from viremic/treatment-naive persons compared to uninfected control samples (data not shown).

In an attempt to investigate further the capacity of HIV-1 to promote DCIR expression, in vitro studies were performed using human primary CD4⁺ T cells acutely infected with X4- and R5-using virus isolates (i.e. NL4-3 and NL4-3/Balenv, respectively). Exposure of purified CD4⁺ T cells to NL4-3 for 3 days triggers DCIR expression on the cell surface (FIG. 9C). Similar observations were made when infection was carried out in parallel with the two tested viral isolates. For example, DCIR was detected in 9.0±1.5% and 8.6±0.8% of CD4⁺ T cells inoculated with NL4-3 and NL4-3/Balenv, respectively (n=3) (data not shown). In some experiments, cells were first pre-treated with the antiretroviral drug efavirenz (EFV) before virus infection. This experimental strategy was used to decipher if the virus-mediated induction of DCIR requires a complete replicative cycle (i.e. productive infection). Treatment of purified CD4⁺ T cells with EFV reduced significantly the percentage of DCIR-expressing cells, thus indicating that productive infection with HIV-1 is mandatory to lead to DCIR expression. Altogether these results suggest that HIV-1 drives DCIR expression in vivo and in vitro in CD4⁺ T cells, a cell population recognized as a major cellular reservoir for HIV-1.

Experiments were also performed with Vpr- or Nef-deleted mutant to define the possible contribution of each single gene in the virus-mediated induction of DCIR expression on the surface of CD4⁺ T cells. Induction of DCIR was similar when cells were acutely infected with wild-type and Vpr- or Nef-deleted mutant viruses (data not shown).

Example 9

HIV-1 Induces DCIR Expression in Both Infected and Bystander CD4⁺ T Cells

Figure 10:
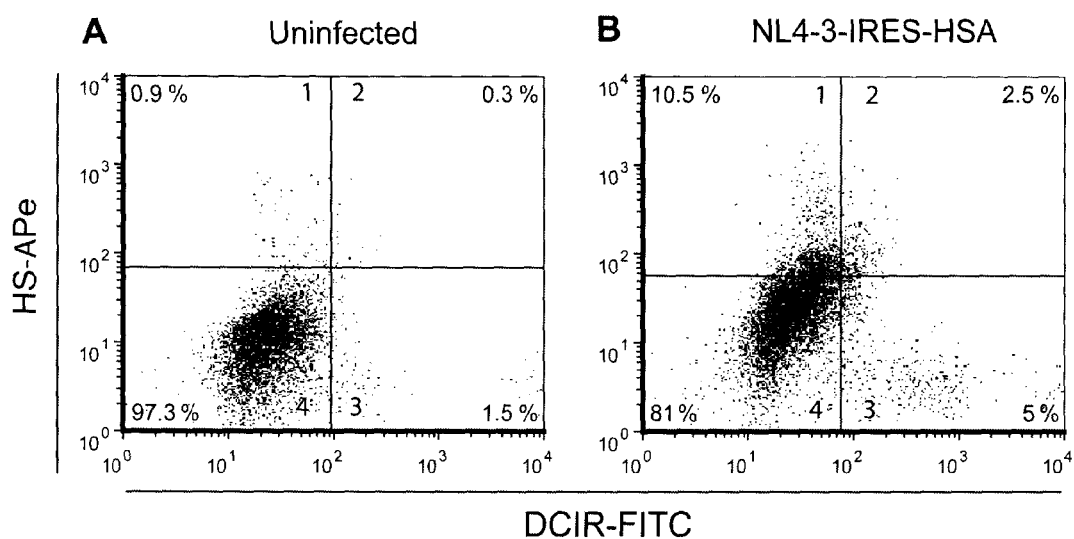
FIG. 10 shows that DCIR is expressed in both virus-infected and bystander CD4$^+$ T cells. Cells (1×10$^6$) were either left (FIG. 10A) uninfected or (FIG. 10B) infected with NL4-3-IRES-HSA reporter virus (100 ng of p24). Three days later, a double-stain flow cytometric method was performed to assess the percentages of DCIR-expressing and HSA-positive cells. Data shown correspond to a single experiment representative of 3 independent experiments.

We next set out to determine whether induction of DCIR occurs in virus-infected and/or bystander cells. This fundamental question was addressed through the use of a novel HIV-1 reporter construct, NL4-3-IRES-HSA, which, unlike most of the previous reporter constructs, will lead to the production of fully competent virions [89]. This $X_4$-tropic infectious molecular clone of HIV-1 codes for all viral genes, with no deletions in env, vpr, or nef. It also expresses a cell surface reporter molecule, the murine heat-stable antigen (HSA), which permits the detection by flow cytometry of cells productively infected with HIV-1 through the surface expression of the HSA molecule. Briefly, human primary CD4⁺ T cells were exposed to NL4-3-IRES-HSA for 3 days and surface expression of HSA and DCIR was monitored by flow cytometry. Data shown in Table 5 demonstrate that 15.8±3.1% of cells are productively infected with HIV-1 (i.e. HSA-positive), whereas DCIR is expressed in 5.0±0.8% of cells and 2.3±0.2% of cells express both HSA and DCIR (n=3) (a representative donor is depicted in FIG. 10). Therefore, about 46% of DCIR-expressing cells are infected with HIV-1 and 56% of DCIR-positive cells are uninfected. It can be concluded that HIV-1 infection of CD4⁺ T cells promotes membrane expression of this C-type lectin surface receptor in both virus-infected and bystander cells.

Example 10

DCIR Expression in Bystander Cells is Due to Soluble Factors Produced by CD4⁺ T Cells Productively Infected with HIV-1

Figure 11:
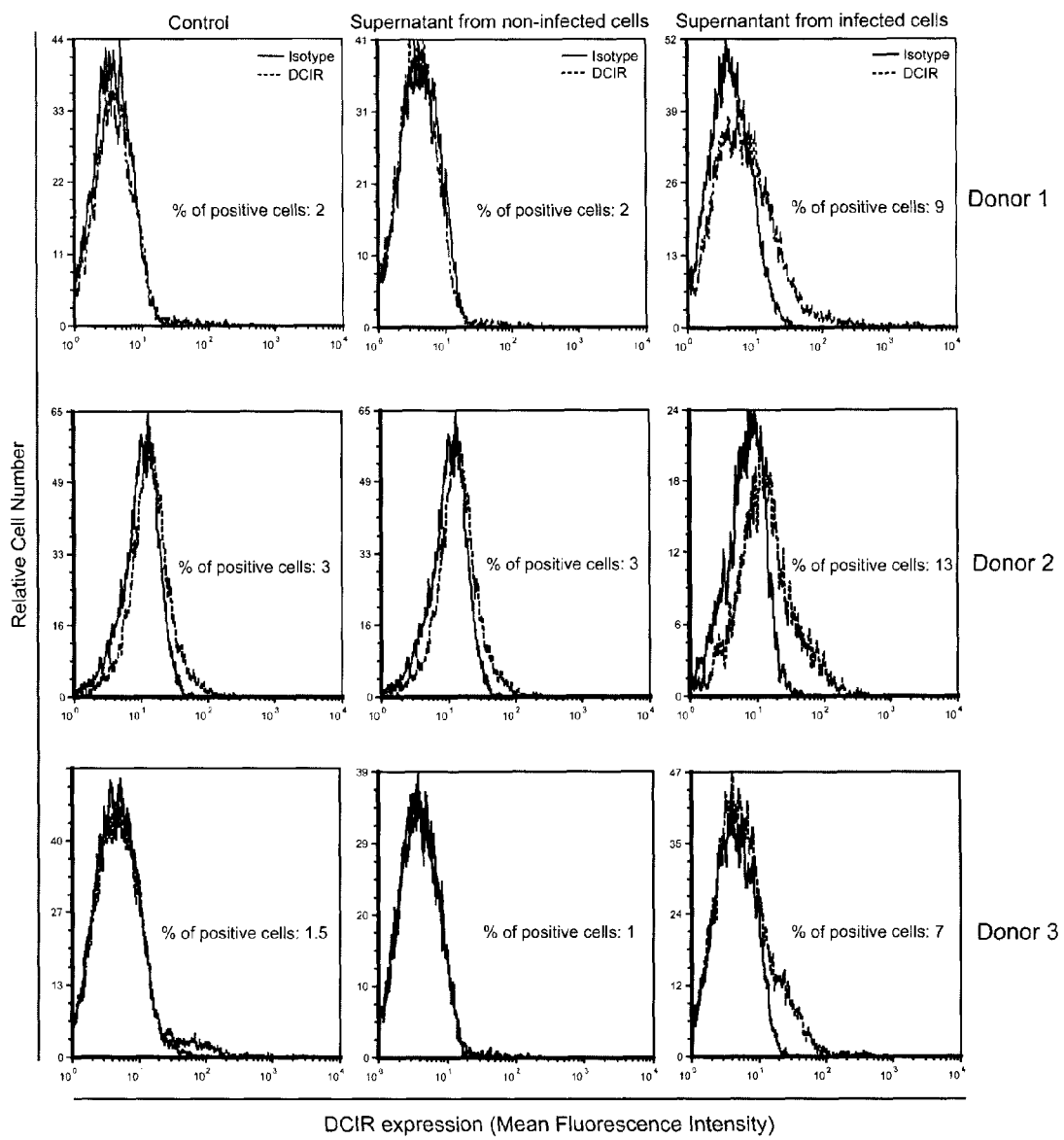
FIG. 11 shows that soluble factors secreted by virus-infected cells promote DCIR expression. Cell-free supernatants from mock- and HIV-1-infected cells were used to treat purified CD4$^+$ T cells. DCIR expression was monitored 3 days later by flow cytometry. Expression of DCIR is shown as a dotted line, whereas the continuous line represents staining obtained with an isotype-matched irrelevant control Ab. Data shown correspond to studies performed with three distinct donors.

Our previous findings indicate that HIV-1 induces DCIR expression not only in virus-infected but also in bystander cells as well. Our next set of experiments was aimed at defining the possible involvement of soluble factors produced by infected cells in the up-regulation of DCIR seen in bystander cells. To this end, human primary CD4⁺ T cells were cultured with cell-free culture supernatants from HIV-1-infected cells and DCIR expression was monitored by flow cytometry. As shown in FIG. 11, exposure of CD4⁺ T cells to supernatants originating from cells acutely infected with HIV-1 is sufficient per se to drive DCIR expression in the three distinct donors studied.

Example 11

Figure 12:
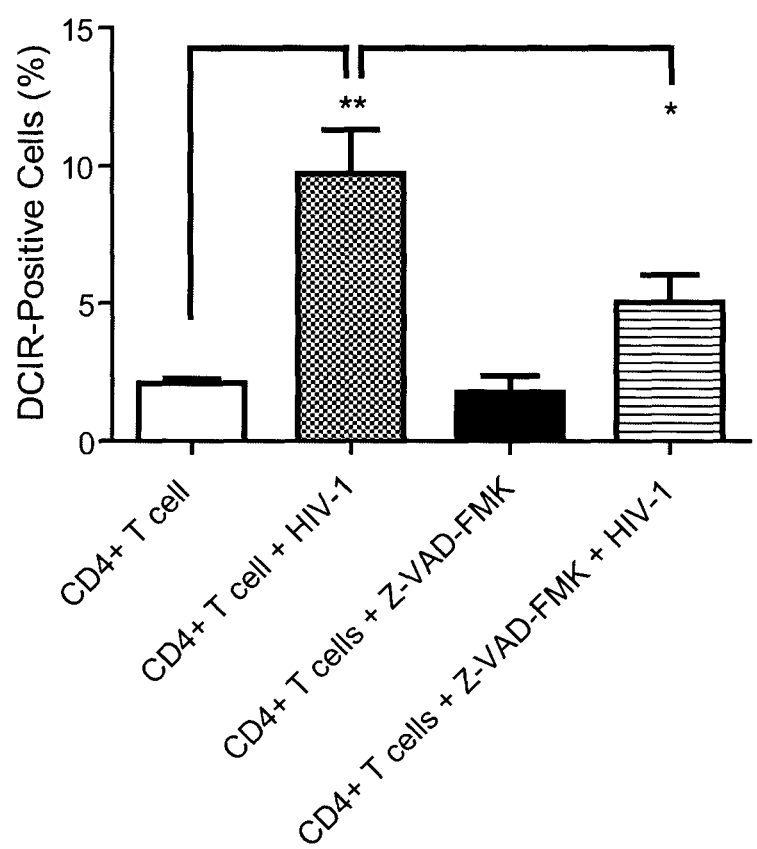
FIG. 12 shows that virus-mediated induction of DCIR is partly prevented by a caspase inhibitor. Mitogen-activated CD4$^+$ T cells (1×10$^6$) were first either left untreated or treated for 1 h with the caspase inhibitor Z-VAD-FMK (50 nM), after which HIV-1 was added (100 ng of p24), where indicated. DCIR expression was monitored 3 days later by flow cytometry. Data shown represent the means±SD of triplicate samples from three independent experiments. Asterisks denote statistically significant data (*, P<0.05; **, P<0.01).

Correlation Between HIV-1-Mediated DCIR Expression and Apoptosis Through Both Caspase-Dependent and -Independent Intrinsic Pathways The HIV-1-mediated induction of apoptosis in both infected and bystander CD4⁺ T cells is a well-described phenomenon [90, 91, 92]. The peak of apoptosis is observed usually after 2 to 3 days [80], the same time frame in which we detected the HIV-1-dependent induction of DCIR. Therefore, we next assessed whether there might be a connection between the virus-induced DCIR expression and apoptosis. We initially assessed the ability of NL4-3-IRES-HSA reporter virus to drive apoptosis in CD4⁺ T cells using FITC-VAD-FMK staining. This fluorochrome-labeled pan-caspase inhibitor is a specific and convenient-to-use marker of apoptotic cells, which can identify very early events of apoptosis associated with caspase activation (i.e. pre-apoptotic cells) [93]. Our studies indicate that NL4-3-IRES-HSA virions can potently mediate apoptosis in human primary CD4⁺ T cells (data not shown). As expected, the percentages of apoptotic cells in both virus-infected (i.e. HSA-positive) and bystander cells (HSA-negative) were significantly reduced upon EFV treatment (data not shown). To establish a link between DCIR expression and apoptosis following HIV-1 infection, we carried out a series of investigations with the broad-spectrum caspase inhibitor Z-VAD-FMK [94]. As illustrated in FIG. 12, the HIV-1-mediated DCIR up-regulation was partially reduced in presence of Z-VAD-FMK, thus suggesting that the virus-directed increased expression of DCIR is associated with both caspase-dependent and -independent apoptotic pathways.

Figure 13:
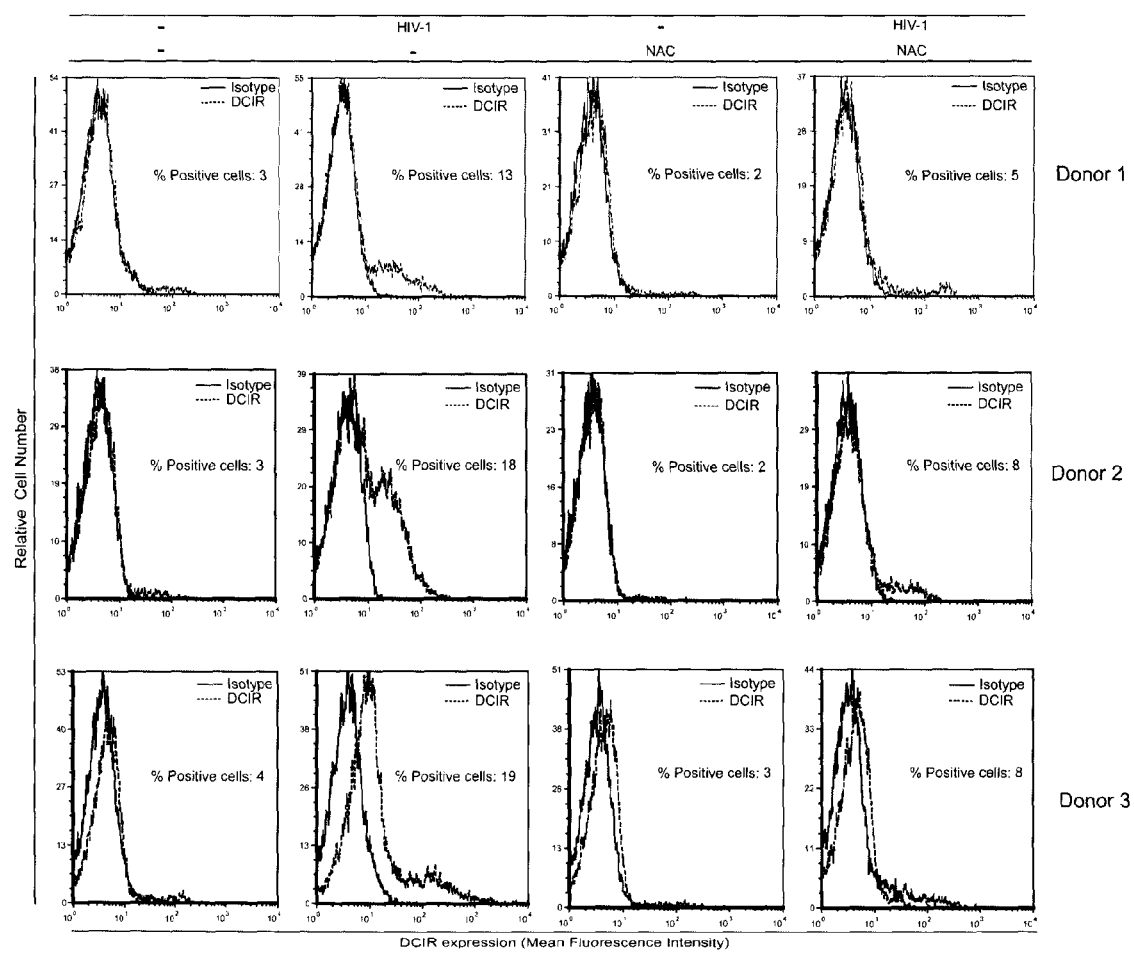
FIG. 13 shows that HIV-1-dependent DCIR induction is due also to a caspase-independent process involving AIF. Cells (1×10$^6$) were first either left untreated or treated for 1 h with NAC, after which HIV-1 (100 ng of p24) was added. DCIR expression was monitored 3 days later by flow cytometry. Expression of DCIR is shown as a dotted line, whereas the continuous line represents staining obtained with an isotype-matched irrelevant control Ab. Data shown correspond to a single experiment representative of 3 independent experiments.

To shed light on the nature of the caspase-independent death mechanism, we studied the involvement of the apoptotic effector protein AIF based on the previous report showing that HIV-1 induces a mitochondrial-mediated but caspase-independent apoptosis controlled by AIF [95]. The possible contribution of AIF was investigated through the use of the inhibitor of apoptosis N-acetyl-L-cystein (NAC), which blocks nuclear translocation of AIF. Our results demonstrate that the HIV-1-induced expression of DCIR on the surface of human primary CD4⁺ T cells is inhibited but not completely by a NAC treatment (i.e. 16.2±3.4% in HIV-1-infected cells compared to 6.7±1.7% in virus-infected cells also treated with NAC) (n=3) (a representative donor is depicted in FIG. 13). Experiments were performed also with both Z-VAD-FMK and NAC to see if this double treatment can totally inhibit the virus-mediated induction of DCIR expression. Unfortunately the concomitant use of the two compounds is leading to cell toxicity (data not shown). It should be noted that no toxicity is seen when each compound are tested individually (data not shown). Nevertheless, we provide evidence that there is a close connection between DCIR expression and apoptosis (through caspase-dependent and -independent pathways) after acute infection of CD4+ T cells with HIV-1.

Example 12

Figure 14:
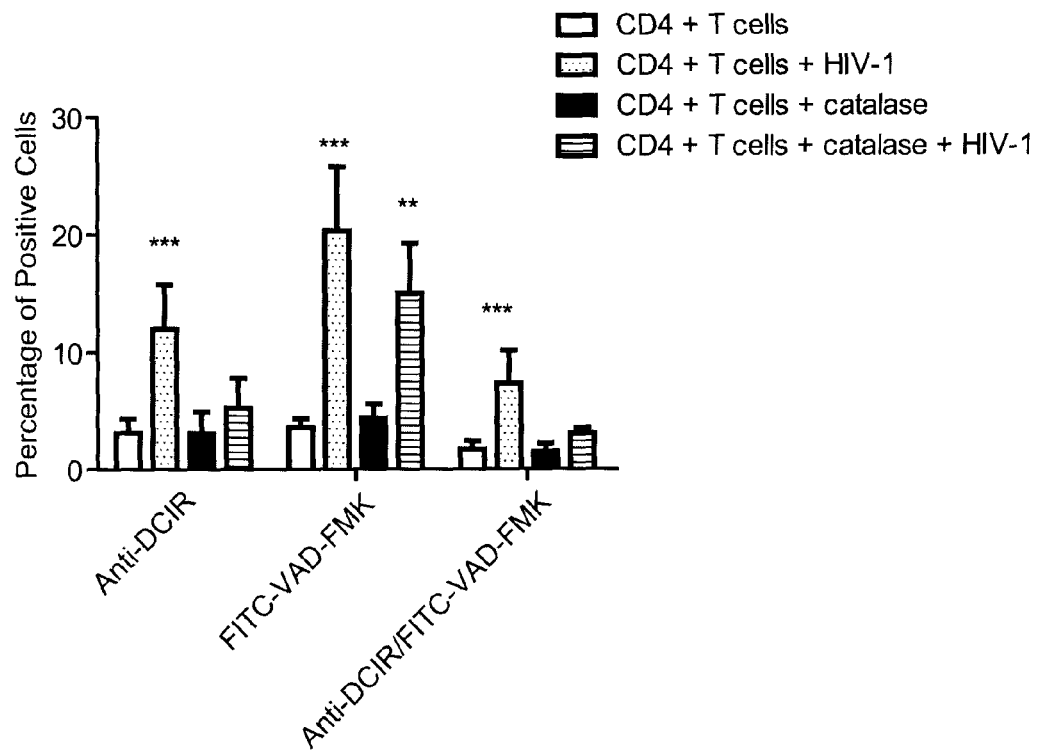
FIG. 14 shows that $H_2O_2$ produced by HIV-1-infected cells promotes DCIR expression. Mitogen-stimulated CD4$^+$ T cells (1×10$^6$) were either left untreated or treated with catalase before HIV-1 infection. Three days after virus infection, DCIR expression was measured by flow cytometry. Data shown represent the means±SD of triplicate samples from three independent experiments. Asterisks denote statistically significant data (, P<0.01; *, P<0.001).

HIV-1 Infection of CD4+ T Cells Results in DCIR Expression Partly Due to a Free Radical, Caspase-Dependent Apoptosis Pathway In HIV-1-infected patients, the hyperactivation status is accompanied by an increased production of free radicals (e.g. superoxide anion, hydroxyl radical and hydrogen peroxide). This excess of reactive oxygen species (ROS) damages cell membranes and generates apoptosis [96]. To establish a putative relationship between DCIR expression and apoptosis induced by free radicals after HIV-1 infection, we performed a double staining with anti-DCIR and FITC-VAD-FMK in virus-infected CD4+ T cells treated with catalase because this enzyme is a known scavenger of ROS (including hydrogen peroxide). Results depicted in FIG. 14 suggest that free radicals are indeed playing a functional role in the HIV-1-mediated induction of DCIR seen in apoptotic cells (i.e. positive for both DCIR and FITC-VAD-FMK).

Figure 15:
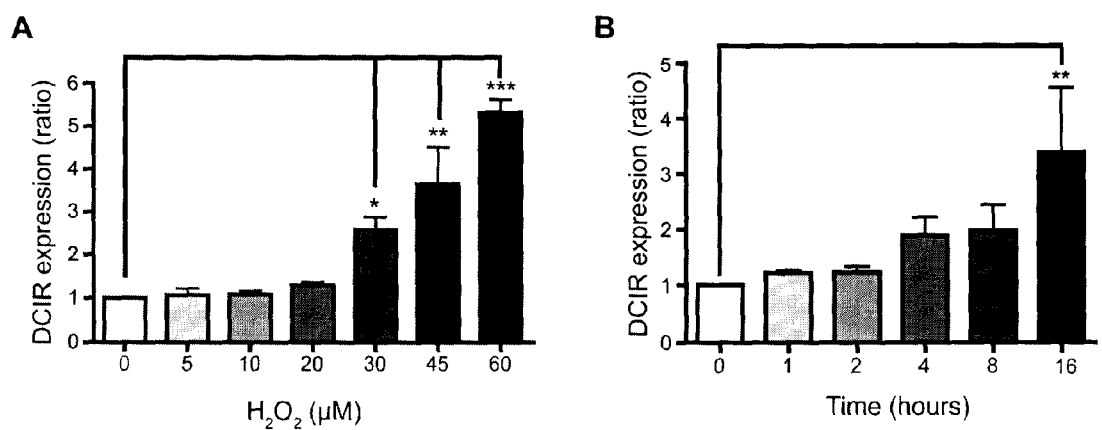
FIG. 15 shows that $H_2O_2$ mediates both apoptosis and DCIR expression. Mitogen-stimulated CD4+ T cells (1×10$^6$) were exposed to increasing concentrations of $H_2O_2$ for 16 h (FIG. 15A) or treated with a constant dose of $H_2O_2$ (i.e. 30 µM) for the indicated time lengths (FIG. 15B). Next, DCIR expression was assessed by flow cytometry. Data shown represent the ratio of DCIR expression over basal expression. The ratio is calculated from the means±SD of triplicate samples from three independent experiments. Asterisks denote statistically significant data (*, P<0.05; , P<0.01; *, P<0.001).

Hydrogen peroxide ($H_2O_2$), a representative ROS, has been extensively used to study apoptosis following an oxidative stress [97]. Thus, additional experiments were performed in human primary CD4+ T cells using $H_2O_2$ as an inducer of an apoptotic-like cell death. Exposure of mitogen-stimulated CD4+ T cells to concentrations of $H_2O_2$ ranging from 20 to 60 µM led to a dose-dependent increased in DCIR expression (FIG. 15A). Cell viability was reduced when using doses of $H_2O_2 \geq 45$ µM (data not shown). Consequently, the subsequent experiments were performed using $H_2O_2$ at a final concentration of 30 µM. A time-course analysis indicated that the $H_2O_2$-mediated expression of DCIR is maximal at 16 h post-treatment and reached a plateau at a longer time period (i.e. 32 h) (FIG. 15B and data not shown). The specificity of the relation between DCIR expression and apoptosis was addressed by estimating surface expression of two other HIV-1 receptors, namely DC-SIGN (used as a negative control) and CD4. Our data demonstrate that both cell surface molecules are not modulated upon induction of apoptosis by $H_2O_2$ (data not shown). Importantly, DCIR was promoted as well by staurosporine (data not shown), a well-known inducer of apoptosis in a wide range of cell lines [98], which further confirms the connection between DCIR and apoptosis.

Figure 16:
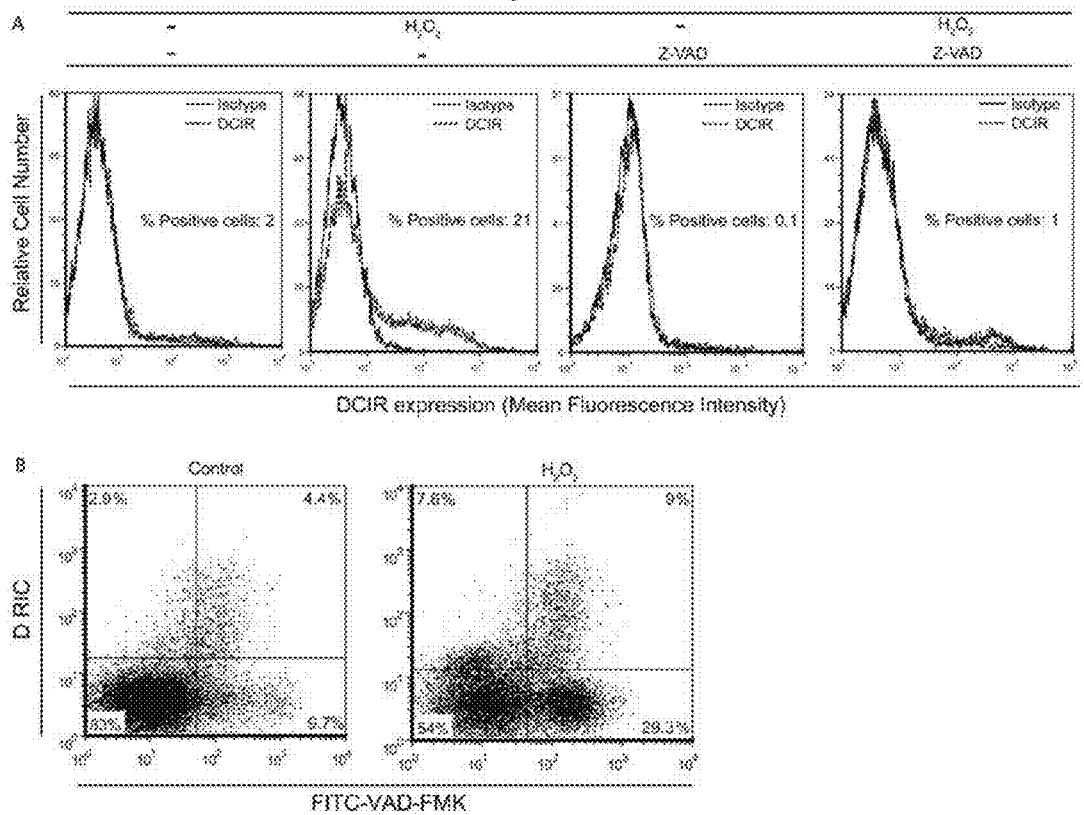
FIG. 16 shows that $H_2O_2$ treatment drives DCIR expression in both nonapoptotic and apoptotic cells.

Given that $H_2O_2$ induces also necrosis and mediates apoptosis primarily via a caspase-dependent pathway [99, 100], we performed experiments with Z-VAD-FMK. A pretreatment with Z-VAD-FMK prevented DCIR expression in activated CD4+ T cells after $H_2O_2$ stimulation (i.e. 21.4±3.4% in $H_2O_2$-treated cells compared to 1.0±0.2% in cells treated with both $H_2O_2$ and Z-VAD-FMK) (n=3) (a representative donor is depicted in FIG. 16A). Experiments were repeated in quiescent CD4+ T cells and we made similar observations (data not shown). Overall our results indicate that the $H_2O_2$-driven induction of DCIR is not due to necrosis and occurs through a caspase-mediated signal transduction pathway. Moreover, we estimated the percentages of apoptotic cells that express DCIR following $H_2O_2$ treatment. For this purpose, human primary CD4+ T cells were labeled with FITC-VAD-FMK and anti-DCIR. We found that 12.2±3.2% of apoptotic cells are also positive for DCIR (n=3) (a representative donor is depicted in FIG. 16B), which confirms the relationship between DCIR and apoptosis in CD4+ T cells.

Example 13

Figure 17:
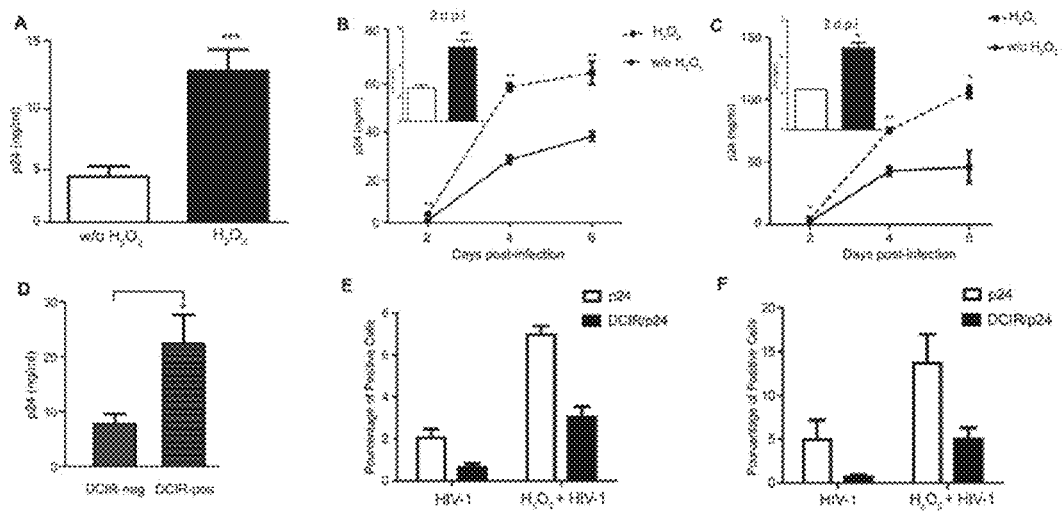
FIG. 17 shows that HIV-1 attachment/entry, replication and transfer processes are all promoted in $H_2O_2$-treated CD4+ T cells. Target CD4+ T cells (1×10$^6$) were treated for 16 h with $H_2O_2$ (30 µM) to induce surface expression of DCIR.

HIV-1 Binding/Entry, Infection and Transfer Processes are all Promoted by ROS-Mediated Induction of DCIR Taken together, our findings demonstrated that the HIV-1-mediated apoptosis promotes DCIR surface expression in CD4+ T cells. Previous results indicate that DCIR can capture HIV-1 on DCs, enhance de novo virus production by DCs (i.e. infection in cis), and increase DC-mediated virus transmission to CD4+ T cells (i.e. infection in trans) [18]. Experiments were thus carried out to define first whether HIV-1 attachment/entry in CD4+ T cells can be affected by the $H_2O_2$-dependent increase in DCIR expression. As illustrated in FIG. 17A, the early steps in the virus life cycle (i.e. binding and entry) are enhanced in CD4+ T cells following exposure to $H_2O_2$ (i.e. 12.5±1.8 versus 3.8±0.8 ng/ml of p24). We next set out to determine whether acute HIV-1 infection was also affected under these conditions. A statistically significant increase in virus production was seen in cells treated with $H_2O_2$ (FIG. 17B). Similarly, virus transfer was also enhanced when DCIR-expressing CD4 T cells are used as transmitter cells (FIG. 17C). To further strengthen the contribution of DCIR in the virus trans-infection pathway, CD4+ T cells were first exposed to $H_2O_2$ to induce DCIR expression. Thereafter, DCIR-negative and DCIR-positive cells were isolated and used separately in HIV-1 transfer experiments. Data shown in FIG. 17D demonstrate that HIV-1 transmission toward uninfected CD4+ T cells (i.e. recipient cells) is augmented when using, as transmitter cells, DCIR-positive CD4+ T cells. Finally, to substantiate the participation of DCIR in HIV-1 replication, $H_2O_2$-treated/virus-infected CD4+ T cells were subjected to a dual staining immunofluorescence method to detect both intracellular HIV-1 p24 and surface DCIR. An increase in virus binding/entry was detected in $H_2O_2$-treated cells expressing DCIR (FIG. 17E). A similar augmentation in cells expressing both DCIR and p24 was detected following acute virus infection (FIG. 17F).

Discussion

We report here that DCIR is expressed on CD4+ T cells originating from aviremic/treated and viremic/untreated seropositive patients, whereas, no expression was detected in cells from healthy donors. These results suggest that DCIR expression on the surface of circulating CD4+ T cells seems to be a generalized phenomenon in the context of various inflammatory diseases.

To acquire additional information about the ability of HIV-1 to induce DCIR expression in a cell subpopulation that is infected under physiological conditions, we performed in vitro experiments where human primary CD4+ T cells were acutely infected with X4- and R5-tropic virions and monitored DCIR expression. We showed that HIV-1 drives DCIR expression in both infected and bystander cells. Moreover, we monitored DCIR levels in the CD4+ T cell subpopulation following acute HIV-1 infection of unseparated peripheral blood mononuclear cells. Therefore, we defined whether expression of the immunoreceptor DCIR on the surface of CD4+ T cells in the context of HIV-1 infection could perhaps be considered as a possible marker of apoptosis for these cells. We performed experiments and discovered effectively that there is a certain correlation between HIV-1 infection, DCIR expression and induction of apoptosis. We provide evidence that there is a connection between HIV-1-mediated induction of DCIR expression and apoptosis, the latter being caused by a caspase-dependent pathway in response possibly to a mitochondrial $H_2O_2$ generation by virus-infected cells and a caspase-independent process involving AIF. Our data are in agreement with published reports since Vpr has been shown to induce cell death via the mitochondrial caspase-independent death effector AIF [95] and Vpr can also induce a decrease of mitochondrial membrane potential along with the release of cytochrome c [101].

We corroborated that human primary CD4+ T cells are sensitive to apoptosis caused by $H_2O_2$, a representative ROS that has been extensively used to study apoptosis following an oxidative stress [97]. Based on this information and the previous demonstration that free radicals are actively produced by CD4+ T cells from HIV-1-carrying patients [96], we showed here that $H_2O_2$ induces also DCIR expression. The $H_2O_2$-mediated induction of apoptosis was not only detected in human primary CD4+ T cells but also in Raji and 293T cells (data not shown). No increase in DCIR expression was seen when using a previously reported anti-Fas monoclonal antibody [105] (data not shown), which is an effector of the extrinsic apoptosis pathway [106]. These results indicate that the DCIR induction in CD4+ T cells seen after HIV-1 infection is partly associated with a caspase-dependent intrinsic apoptotic process.

An increased expression of DCIR was also observed in a proportion of bystander cells undergoing apoptosis. Experiments carried out with cell-free supernatants from HIV-1-infected cells revealed that soluble factors are sufficient to drive not only apoptosis but also DCIR expression.

More relevant to the pathogenesis of HIV-1 infection, we demonstrated that the $H_2O_2$-mediated induction of DCIR and apoptosis is coupled with an increased virus binding/entry and higher replication of HIV-1 in CD4+ T cells. Additionally, the noticed up-regulated DCIR expression is also leading to more efficient virus propagation. It can be proposed that DCIR, once expressed onto such CD4+ T cells, can participate actively to HIV-1 propagation. Although it might seem irrational that apoptotic cells would be more susceptible to productive HIV-1 infection, it should be stated that the fluorochrome-labeled pan-caspase inhibitor FITC-VAD-FMK, which was used to monitor the link between HIV-1-mediated DCIR expression and apoptosis, permits to identify the very early events of apoptosis (i.e. pre-apoptotic cells). Thus it is possible that virus binding/entry and replication processes can still occur during a certain time period in CD4+ T cells that are in a pre-apoptotic state. It is known that HIV-1 exploits different strategies to escape the immune response including a rapid/high mutation rate, down-regulation of major histocompatibility complex class-1 molecules, broad coreceptor usage and destruction of both CD4- and CD8-expressing T cells [111]. We suggest that HIV-1 can utilize DCIR as another tactic for escaping the immune system and/or increasing its infectivity. Different hypotheses may be formulated with respect to the role(s) played by DCIR once expressed on the surface of CD4+ T cells.

Figure 18:
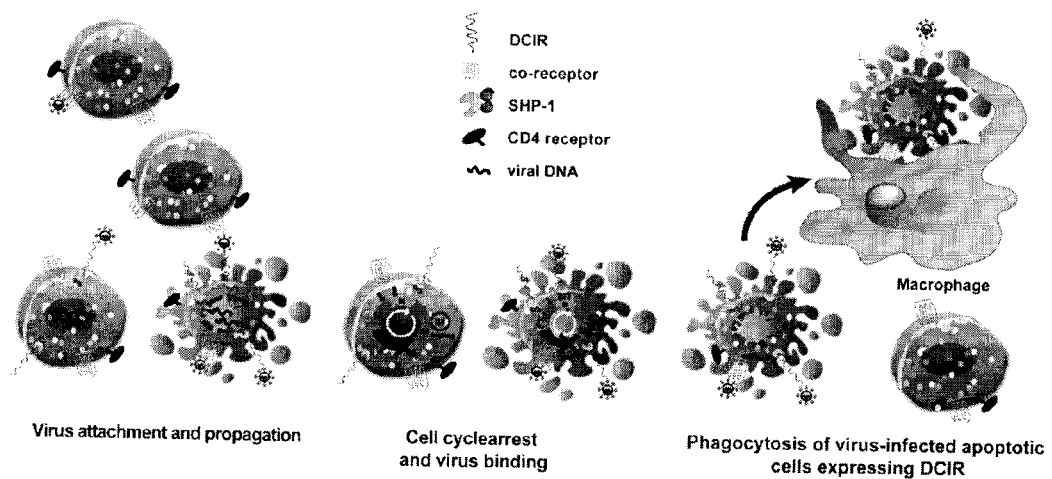
FIG. 18 is a schema illustrating a proposed working models for DCIR involvement in HIV-1 infection. DCIR expression is promoted not only in cells productively infected with HIV-1 but also in bystander cells via both a mitochondrial (intrinsic) caspase-dependent apoptotic pathway and a caspase-independent apoptotic process relying on AIF. The resulting DCIR induction on the surface of CD4+ T cells can affect virus replication by various means. For example, virus binding can be increased through DCIR, a process leading to a more efficient HIV-1 propagation. Moreover, the cell cycle arrest seen in DCIR-expressing cells can also promote virus attachment and the ensuing HIV-1 transmission despite apoptosis induction because of the association between DCIR and SHP-1. It can also be postulated that DCIR expression on the surface of apoptotic CD4+ T cells also infected with HIV-1 might facilitate phagocytosis by macrophages and DCs, thereby favoring infection of such antigen-presenting cells and viral propagation and establishment of reservoir.

It can be hypothesized that induction of apoptosis increases virus attachment/entry likely through DCIR expression on the surface of CD4+ T cells (FIG. 18). This theory is supported by our results showing that the $H_2O_2$-mediated induction of apoptosis in CD4+ T cells and DCIR expression are not accompanied by a modulation of surface expression of two other attachment factors for HIV-1, i.e. DC-SIGN and CD4. DCIR carries an immunoreceptor tyrosine-based inhibitory motif (ITIM) in its cytoplasmic tail that is thought to be responsible for the immunoregulatory role played by this cell surface molecule. The intracellular ITIM motif of DCIR is involved in SHP-1 recruitment [26], a tyrosine phosphatase known for its important role in maintaining cellular homeostasis [112]. The protein tyrosine phosphatase SHP-1 has also been shown to regulate HIV-1 transcription [113] and inhibit antigen-receptor-induced apoptosis [114]. Interestingly, DCIR-expressing cells following acute HIV-1 infection display a cell cycle arrest (data not shown), which might permit virus attachment despite the appearance of a pre-apoptotic state. Thus, the life cycle of HIV-1 can be affected in several ways by the newly expressed DCIR and recruited SHP-1 molecules.

It can also be postulated that DCIR expression may lead to phagocytosis by macrophages and DCs of apoptotic CD4+ T cells also infected with HIV-1, thereby promoting viral propagation and infection of such antigen-presenting cells. It is well established that macrophages play a central role in the pathogenesis of HIV-1 infection, functioning as stable viral reservoir due to their ability to resist HIV-1-mediated cytopathicity. Of importance to note is the previous report showing that phagocytosis of apoptotic cells induced an increase in HIV-1 replication in macrophages [115]. Similarly, we observed that HIV-1 replication in macrophages is enhanced when such cells are co-cultured with DCIR-positive apoptotic CD4+ T cells treated with $H_2O_2$ (data not shown).

Additionally, instead of inducing an inflammatory immune response, phagocytosis of DCIR-expressing apoptotic cells might promote the generation of suppressor macrophages as described previously for bacterial infections [116] and tumor cells [117]. This would allow microorganisms such as HIV-1 to escape the immune system. Alternatively, it is possible that DCIR is induced after HIV-1 infection because it acts as a death signal for the cell and/or as a sign to promote phagocytosis. It can also be proposed that DCIR facilitates HIV-1 attachment before cell death, a process leading to more extensive virus dissemination across the organism.

Together, our work represents the first evidence that DCIR can serve as a marker for apoptosis in the context of an HIV-1 infection.

Despite intensive efforts to improve understanding of HIV-1 pathogenesis and immune protection, the pandemic continues to expand and no effective vaccine is available or appears likely to become available in the near future. Our study provides novel and cogent insight into salient aspects of HIV-1 transmission by DC and more particularly into the role of DCIR signalling event in this process. Furthermore, molecular and functional characterization of signal transducer by DCIR after HIV-1 capture, provide fundamental information to the development of novel approaches to the control of HIV-1 transmission. Intracellular protein phosphorylation represents one of the most critical and dynamic mechanisms by which cellular functions are regulated. The present study examined the signalling cascade induced by DCIR upon its engagement by HIV-1. We provide novel and relevant insight into significant aspects of DCIR signalling, more particularly into the nature of intracellular biochemical events involved in HIV-1-mediated DCIR signalling. This study also identified for the first time and by using several innovative approaches several components of the signal transduction involved in DCIR stimulation. Briefly, the importance of PTPs such as SHP-1 and SHP-2, Syk, Src kinases (Src, Fyn and Hck), PKC-α, MAP kinases (ERK1/2 and p38) was showed, as well as the pivotal role of the tyrosine and threonine residues located in the intracellular ITIM motif of DCIR.

We speculated that another amino acid of DCIR ITIM domain upstream from the tyrosine could be important in conferring the ability to signal. We thus performed site-directed mutagenesis on the threonine preceding the tyrosine and showed the importance of this residue in DCIR signalling upon engagement by HIV-1.

As a complementary experiment to site-directed mutagenesis, we introduced ITIM peptides bearing a phosphorylated tyrosine or threonine in primary human cells known to express high levels of DCIR (i.e. DCs). This allowed us to observe a decrease of both HIV-1 binding and infection. So it can be proposed that soluble peptides containing the ITIM sequence of DCIR interfere with the recruitment of signalling proteins to the receptor.

Knowing that engagement of DCIR by HIV-1 can leads to phosphorylation of two amino acids of the ITIM intracellular domain, the obvious next question is the identity of the phosphatase(s) and/or kinase(s) involved in this process. This goal was reached by using pharmacological inhibitors and well as antisense oligonucleotides. We provide evidence here that the Syk and Src families of tyrosine kinases are implicated in the HIV-1-mediated DCIR signalosome. The Src family comprises eight members of NRTKs like Src, Fyn, Yes, Lyn, Fgr, Hck, Lck, Blk and Csk. Three of them (Src, Fyn and Yes) are ubiquitously expressed, while the other five display a tissue-specific expression. For example, Hck is only expressed in hematopoietic cells. Among the Src family members tested, only three of them seem to be involved in DCIR signalling (i.e. Scr, Fyn and Hck).

Likewise, our results indicate that PKC-α participates in DCIR signalling. The PKC family constitutes a large group of Ser/Thr kinases but nothing is known about the implication of PKC-α in DCIR signalling. We hypothesize that, among other possible roles discussed below, PKC-α phosphorylates the threonine of the ITIM motif in order to induce signalling.

Subtle differences in ITIM sequences can result in the differential recruitment of phosphatases by various receptor systems, presumably because of differences in the binding specificity of the phosphatase SH2 domains. Therefore, some ITIMs recruit the tyrosine phosphatases SHP-1 and SHP-2, whereas others bind the inositol polyphosphate 5'-phosphatase, SHIP, and some bind all three[24,25]. Previous observations in neutrophils had shown the tyrosine-phosphorylated ITIM of DCIR to bind to SHP-1 and SHP-2[26]. Our results show that ligation of DCIR by HIV-1 also leads to activation of SHP-1 and SHP-2, since blocking them either with an inhibitor or antisense oligonucleotide causes a significant diminution of HIV-1 binding/entry and infection. It is noteworthy that SHP-1 can be a substrate of PKC-α[46]. In fact, phosphorylation of S591 by PKC-α decreases phosphatase activity of SHP-1 and consequently increases TK activity by inhibition of phosphatase. Finally, it has recently been described that PKC-α mediates serine phosphorylation of Syk and that this event is necessary for tyrosine phosphorylation and activity[58]. Thus, PKC-α is likely to be involved in different pathways of DCIR signalling.

In addition, we provide evidence that MAP kinases ERK1/2 and p38 are implicated in the signalosome of DCIR as previously described for DCAL-2[57], another C-type lectin with an ITIM domain that is also expressed in DCs.

Altogether, the data presented herein suggest that there is a relationship between phosphorylation events, the tyrosine and threonine of ITIM motif of DCIR with HIV-1 infection.

These studies bear a clinical relevance, since blocking HIV-1 attachment to DCIR may represent a useful new strategy for fighting this retrovirus. Indeed, preventing the virus to bind DCIR can lead to a significant decrease of transmission during primo-infection, a period during which the virus is disseminated by mucosal DCs expressing DCIR and ultimately transferred to $CD4^+$ T cells. This study contributes to the identification of new therapeutic targets against the pathogens recognized by this lectin.

TABLE 1

Sequences of sense and antisense oligonucleotides

| Target | Antisense/ Sense | Sequence (5'-3') | SEQ ID NO.: | Ref. |
|---|---|---|---|---|
| Syk | Antisense | CATGCTTCAGGGGCCGG | 30 | ([35]) |
| | Sense | CCGGCCCCTGAAGCATG | 31 | |
| SHP-1 | Antisense | CTTGAGCAGGGTCTCTGCATCC | 32 | ([59]) |
| | Sense | GGATGCAGAGACCCTGCTCAAG | 33 | |
| SHP-2 | Antisense | CTCCGCGATGTCATGTTCCT | 34 | ([60]) |
| | Sense | AGGAACATGACATCGCGGAG | 35 | |
| PKC-α | Antisense | CCAGTCACTCGCACCATCGC | 36 | ([61]) |
| | Sense | CAGCCATGGTTCCCCCCAAC | 37 | |
| PKC-α | Antisense | GCGCGCGTTCATCCGACT | 38 | ([61]) |
| | Sense | TCAGCCATCTTGCGCGCG | 39 | |
| PKC-α | Antisense | AGCACCAACAATCAACGG | 40 | ([62]) |
| | Sense | GGCCCCACCAGTCTACTG | 41 | |
| PKC-α | Antisense | TTTTCCGAGGTAGTACCGTG | 42 | ([61]) |
| | Sense | GTGCCATGATGGAGCCTTTT | 43 | |
| PKC-α | Antisense | ATTGAACACTACCATGGT | 44 | ([61]) |
| | Sense | TGGTACCATCACAAGTTA | 45 | |
| Erk | Antisense | AGCCGCCGCCGCCGCCGCCA | 46 | ([63]) |
| | Sense | ATGGCGGCGGCGGCGGCGGCA | 47 | |
| Fgr | Antisense | ACACACAGCCCATTCCAGGT | 48 | ([64]) |
| | Sense | ACCTGGAATGGGCTGTGTGT | 49 | |
| Fyn | Antisense | GATAAAGAAGCAGCGAA | 50 | ([65]) |
| | Sense | TTCGCTGCTTCTTTATC | 51 | |
| Lyn | Antisense | CCATATTTCCCGCTCGCGTG | 52 | ([64]) |
| | Sense | CACGCGAGCGGGAAATATGG | 53 | |
| Hck | Antisense | TTCTCGACCCCATCCTGGC | 54 | ([64]) |
| | Sense | GCCAGGATGGGGTCGAGAA | 55 | |
| p38 | Antisense | GTCTTGTTCAGCTCCTGC | 56 | ([66]) |
| | Sense | GCAGGAGCTGAACAAGAC | 57 | |
| Src | Antisense | ATAGAGGGCCACAAAGGT | 58 | ([67]) |
| | Sense | ACCTTTGTGGCCCTCTAT | 59 | |

TABLE 2A

Additional amino acid sequences described in the present application

| Name | Sequence | SEQ ID NO.: |
|---|---|---|
| ITIM peptide consensus | $Xaa_1Xaa_2Xaa_3Xaa_4Xaa_5Xaa_6$ Wherein $Xaa_1$ is S, I, V or L | 2 |

TABLE 2A-continued

Additional amino acid sequences described in the present application

| Name | Sequence | SEQ ID NO.: |
|---|---|---|
| | wherein Xaa$_2$ is any amino acid or phospho-threonine;<br>wherein Xaa$_3$ is tyrosine or phospho-tyrosine;<br>wherein Xaa$_4$ or Xaa$_5$ are independently any amino acid<br>wherein Xaa$_6$ is I, V or L;<br>wherein at least one of Xaa$_2$ or Xaa$_3$ is a phospho-amino acid | |
| ITIM peptide | EIX$_1$X$_2$AEVRFKNEFKS<br>wherein X$_1$ is threonine or phospho-threonine;<br>wherein X$_2$ is tyrosine or phospho-tyrosine;<br>wherein at least one of X$_1$ or X$_2$ is a phospho-amino acid. | 3 |
| TAT splice-F | GAAGCATCCAGGAAGTCAGC | 4 |
| TAT splice-R | CTATTCCTTCGGGCCTGTC | 5 |
| 18S-F | TAGAGGGACAAGTGGCGTTC | 6 |
| 18S-R | CGCTGAGCCAGTCAGTGT | 7 |
| TAT probe | 5' d FAM-TATCAAAGCAACCCACCCACCTCC-BHq-1 3' | 8 |
| 18S probe | 5' d FAM-AACAGGTCTGTGATGCCCTT-BHQ-1 3' | 9 |
| non-phosphorylated ITIM peptide | X$_3$-EITYAEVRFKNEFKS-OH<br>Wherein X$_3$ is absent or is a label for detection purposes | 10 |
| ITIM peptide phosphorylated on tyrosine | X$_3$-EITY(PO$_3$H$_2$)AEVRFKNES-OH<br>Wherein X$_3$ is absent or is a label for detection purposes. | 11 |
| ITIM peptide phosphorylated on threonine | X$_3$-EIT(PO$_3$H$_2$)YAEVRFKNEFKS-OH<br>Wherein X$_3$ is absent or is a label for detection purposes. | 12 |
| control peptide | TAMRA-KENFKRFVAYETIES-OH | 13 |
| ITIM target sequence | EITYAEVRFKNEFKS | 14 |
| ITIM more specific target sequence | ITYAEV | 15 |

TABLE 2A

Additional polypeptides envisioned according to in the present application

| Control | PO-Y | PO-T | PO-Y (mix) | PO-T (mix) |
|---|---|---|---|---|
| ITYAEV -OH (SEQ ID NO: 15) | ITY(PO$_3$H$_2$)AEV -OH (SEQ ID NO: 16) | IT(PO$_3$H$_2$)YAEV -OH (SEQ ID NO: 17) | VAY(PO$_3$H$_2$)ETI-OH (SEQ ID NO: 18) | VAYET(PO$_3$H$_2$)I-OH (SEQ ID NO: 19) |
| ITYAEVRFKN (SEQ ID NO: 20) | EITY(PO$_3$H$_2$)AEV RFKN-OH (SEQ ID NO: 21) | EIT(PO$_3$H$_2$)YAEV RFKN-OH (SEQ ID NO: 22) | VAY(PO3H2)ETIK NFR-OH (SEQ ID NO: 23) | VAYET(PO$_3$H$_2$)IK NFR-OH (SEQ ID NO: 24) |
| EITYAEVRFK NEFKS-OH (SEQ ID NO: 25) | EITY(PO$_3$H$_2$)AEV RFKNEFKS-OH (SEQ ID NO: 26) | EIT(PO$_3$H$_2$)YAEV RFKNEFKS-OH (SEQ ID NO: 27) | KENFKRFVAY (PO$_3$H$_2$)ETIES-OH (SEQ ID NO: 28) | KENFKRFVAYET (PO$_3$H$_2$)IES-OH (SEQ ID NO: 29) |

TABLE 3

| Inhibitor | Target | Binding/entry | Infection |
|---|---|---|---|
| SSG | Tyrosine phosphatases SHP-1 et SHP-2 | — | — |
| PP2 | Src kinases | — | — |
| Pic | Syk | — | — |
| Go6976 | PKCα | — | — |
| H89 | PKA | Ø | Ø |
| PD98059 | P38 | — | — |
| SB203580 | Erk1/2 | — | — |
| Wortmanin | PI3kinase | Ø | Ø |
| LFM-A13 | BTK | Ø | Ø |

TABLE 4

| Protein | Binding/entry | Infection |
|---|---|---|
| SHP-1 | — | — |
| SHP-2 | — | — |
| Src | — | — |
| Fyn | — | — |
| Hck | — | — |
| Fgr | Ø | Ø |
| Lyn | Ø | Ø |
| Syk | — | — |
| PKCα | — | — |
| PKCα | Ø | Ø |
| PKCα | Ø | Ø |
| PKCα | Ø | Ø |
| PKCα | Ø | Ø |
| Erk1/2 | — | — |
| p38 | — | — |

TABLE 5

HIV-1 induces DCIR expression in CD4+ T cells[a].

| | Mock Mean ± SD[b] | NL4-3-IRES-HSA Mean ± SD |
|---|---|---|
| DCIR | 1.0 ± 0.2 | 5.0 ± 0.8 |
| HSA | 1.2 ± 0.8 | 15.8 ± 3.1 |
| DCIR/HSA | 0.6 ± 0.5 | 2.3 ± 0.2 |

[a]CD4+ T cells (1 × 10⁶) were either left uninfected (mock) or infected with NL4-3-IRES-HSA (100 ng of p24). Three days later, a double-staining method was used to estimate DCIR and HSA expression by flow cytometry.
[b]Data shown correspond to the means ± SD of triplicate samples from 3 distinct donors.

REFERENCES

1. Bobardt, M. D. et al. Cell-free human immunodeficiency virus type 1 transcytosis through primary genital epithelial cells. *J Virol* 81, 395-405 (2007).
2. Steinman, R. M. et al. The interaction of immunodeficiency viruses with dendritic cells. *Curr Top Microbiol Immunol* 276, 1-30 (2003).
3. Patterson, B. K. et al. Susceptibility to human immunodeficiency virus-1 infection of human foreskin and cervical tissue grown in explant culture. *Am J Pathol* 161, 867-873 (2002).
4. Brenchley, J. M. et al. CD4+ T cell depletion during all stages of HIV disease occurs predominantly in the gastrointestinal tract. *J Exp Med* 200, 749-759 (2004).
5. Mattapallil, J. J. et al. Massive infection and loss of memory CD4+ T cells in multiple tissues during acute SIV infection. *Nature* 434, 1093-1097 (2005).
6. Guadalupe, M. et al. Severe CD4+ T-cell depletion in gut lymphoid tissue during primary human immunodeficiency virus type 1 infection and substantial delay in restoration following highly active antiretroviral therapy. *J Virol* 77, 11708-11717 (2003).
7. Hazenberg, M. D. et al. Persistent immune activation in HIV-1 infection is associated with progression to AIDS. *AIDS* 17, 1881-1888 (2003).
8. Clapham, P. R. & McKnight, A. HIV-1 receptors and cell tropism. *Br Med Bull* 58, 43-59 (2001).
9. Ugolini, S., Mondor, I. & Sattentau, Q. J. HIV-1 attachment: another look. *Trends Microbiol* 7, 144-149 (1999).
10. Turville, S., Wilkinson, J., Cameron, P., Dable, J. & Cunningham, A. L. The role of dendritic cell C-type lectin receptors in HIV pathogenesis. *J Leukoc Biol* 74, 710-718 (2003).
11. de Witte, L. et al. Syndecan-3 is a dendritic cell-specific attachment receptor for HIV-1. *Proc Natl Acad Sci USA* 104, 19464-19469 (2007).
12. Geijtenbeek, T. B., Engering, A. & Van Kooyk, Y. DC-SIGN, a C-type lectin on dendritic cells that unveils many aspects of dendritic cell biology. *J Leukoc Biol* 71, 921-931 (2002).
13. Ancuta, P. et al. Opposite effects of IL-10 on the ability of dendritic cells and macrophages to replicate primary CXCR4-dependent HIV-1 strains. *J Immunol* 166, 4244-4253 (2001).
14. Canque, B. et al. The susceptibility to X4 and R5 human immunodeficiency virus-1 strains of dendritic cells derived in vitro from CD34(+) hematopoietic progenitor cells is primarily determined by their maturation stage. *Blood* 93, 3866-3875 (1999).
15. Donaghy, H., Gazzard, B., Gotch, F. & Patterson, S. Dysfunction and infection of freshly isolated blood myeloid and plasmacytoid dendritic cells in patients infected with HIV-1. *Blood* 101, 4505-4511 (2003).
16. Geijtenbeek, T. B. et al. DC-SIGN, a dendritic cell-specific HIV-1-binding protein that enhances trans-infection of T cells. *Cell* 100, 587-597. (2000).
17. Granelli-Piperno, A., Finkel, V., Delgado, E. & Steinman, R. M. Virus replication begins in dendritic cells during the transmission of HIV-1 from mature dendritic cells to T cells. *Curr Biol* 9, 21-29 (1999).
18. Lambert, A. A., Gilbert, C., Richard, M., Beaulieu, A. D. & Tremblay, M. J. The C-type lectin surface receptor DCIR acts as a new attachment factor for HIV-1 in dendritic cells and contributes to trans- and cis-infection pathways. *Blood* 112, 1299-1307 (2008).
19. Yokoyama, W. M. & Plougastel, B. F. Immune functions encoded by the natural killer gene complex. *Nat Rev Immunol* 3, 304-316 (2003).
20. Drickamer, K. & Taylor, M. E. Biology of animal lectins. *Annu Rev Cell Biol* 9, 237-264 (1993).
21. Kanazawa, N. Dendritic cell immunoreceptors: C-type lectin receptors for pattern-recognition and signaling on antigen-presenting cells. *J Dermatol Sci* 45, 77-86 (2007).
22. Bates, E. E. et al. APCs express DCIR, a novel C-type lectin surface receptor containing an immunoreceptor tyrosine-based inhibitory motif. *J Immunol* 163, 1973-1983 (1999).
23. Richard, M., Veilleux, P., Rouleau, M., Paquin, R. & Beaulieu, A. D. The expression pattern of the ITIM-bearing lectin CLECSF6 in neutrophils suggests a key role in the control of inflammation. *J Leukoc Biol* 71, 871-880 (2002).
24. Ravetch, J. V. & Lanier, L. L. Immune inhibitory receptors. *Science* 290, 84-89 (2000).
25. Unkeless, J. C. & Jin, J. Inhibitory receptors, ITIM sequences and phosphatases. *Curr Opin Immunol* 9, 338-343 (1997).
26. Richard, M., Thibault, N., Veilleux, P., Gareau-Page, G. & Beaulieu, A. D. Granulocyte macrophage-colony stimulat- 26. ing factor reduces the affinity of SHP-2 for the ITIM of CLECSF6 in neutrophils: a new mechanism of action for SHP-2. *Mol Immunol* 43, 1716-1721 (2006).
27. Gilbert, C., Barat, C., Cantin, R. & Tremblay, M. J. Involvement of Src and Syk tyrosine kinases in HIV-1 transfer from dendritic cells to CD4+ T lymphocytes. *J Immunol* 178, 2862-2871 (2007).
28. Caparros, E. et al. DC-SIGN ligation on dendritic cells results in ERK and PI3K activation and modulates cytokine production. *Blood* 107, 3950-3958 (2006).
29. Kerrigan, A. M. & Brown, G. D. Syk-coupled C-type lectin receptors that mediate cellular activation via single tyrosine based activation motifs. *Immunol Rev* 234, 335-352.
30. Cantin, R., Fortin, J. F., Lamontagne, G. & Tremblay, M. The acquisition of host-derived major histocompatibility complex class II glycoproteins by human immunodeficiency virus type 1 accelerates the process of virus entry and infection in human T-lymphoid cells. *Blood* 90, 1091-1100 (1997).
31. Cantin, R., Fortin, J. F., Lamontagne, G. & Tremblay, M. The presence of host-derived HLA-DR1 on human immunodeficiency virus type 1 increases viral infectivity. *J Virol* 71, 1922-1930 (1997).
32. Dornadula, G., Zhang, H., Shetty, S. & Pomerantz, R. J. HIV-1 virions produced from replicating peripheral blood lymphocytes are more infectious than those from nonproliferating macrophages due to higher levels of intravirion reverse transcripts: implications for pathogenesis and transmission. *Virology* 253, 10-16 (1999).
33. Bounou, S., Dumais, N. & Tremblay, M. J. Attachment of human immunodeficiency virus-1 (HIV-1) particles bearing host-encoded B7-2 proteins leads to nuclear factor-kappa B- and nuclear factor of activated T cells-dependent activation of HIV-1 long terminal repeat transcription. *J Biol Chem* 276, 6359-6369 (2001).
34. Gilbert, C., Rollet-Labelle, E., Caon, A. C. & Naccache, P. H. Immunoblotting and sequential lysis protocols for the analysis of tyrosine phosphorylation-dependent signaling. *J Immunol Methods* 271, 185-201 (2002).
35. Yousefi, S., Hoessli, D. C., Blaser, K., Mills, G. B. & Simon, H. U. Requirement of Lyn and Syk tyrosine kinases for the prevention of apoptosis by cytokines in human eosinophils. *J Exp Med* 183, 1407-1414 (1996).
36. Zar, J. H. *Biostatistical Analysis*. (2nd edn. Englewood Cliffs: Prentice-Hall International, Inc, New Jersey 1984).
37. Sokal, R. R. & Rohlf, F. J. *Biometry*. (W.H. Freeman and company, New York; 1995).
38. Wu, L., Martin, T. D., Carrington, M. & KewalRamani, V. N. Raji B cells, misidentified as THP-1 cells, stimulate DC-SIGN-mediated HIV transmission. *Virology* 318, 17-23 (2004).
39. Pathak, M. K. & Yi, T. Sodium stibogluconate is a potent inhibitor of protein tyrosine phosphatases and augments cytokine responses in hemopoietic cell lines. *J Immunol* 167, 3391-3397 (2001).
40. Yamadori, T. et al. Bruton's tyrosine kinase activity is negatively regulated by Sab, the Btk-SH3 domain-binding protein. *Proc Natl Acad Sci USA* 96, 6341-6346 (1999).
41. Li, Z. et al. Phosphatidylinositol 3-kinase-gamma activates Bruton's tyrosine kinase in concert with Src family kinases. *Proc Natl Acad Sci USA* 94, 13820-13825 (1997).
42. Meyer-Wentrup, F. et al. DCIR is endocytosed into human dendritic cells and inhibits TLR8-mediated cytokine production. *J Leukoc Biol* 85, 518-525 (2009).
43. Fuller, G. L. et al. The C-type lectin receptors CLEC-2 and Dectin-1, but not DC-SIGN, signal via a novel YXXL-dependent signaling cascade. *J Biol Chem* 282, 12397-12409 (2007).
44. Popa-Nita, O. et al. Crystal-induced neutrophil activation. IX. Syk-dependent activation of class Ia phosphatidylinositol 3-kinase. *J Leukoc Biol* 82, 763-773 (2007).
45. Brumell, J. H. et al. Regulation of Src homology 2-containing tyrosine phosphatase 1 during activation of human neutrophils. Role of protein kinase C. *J Biol Chem* 272, 875-882 (1997).
46. Popa-Nita, O., Proulx, S., Pare, G., Rollet-Labelle, E. & Naccache, P. H. Crystal-induced neutrophil activation: XI. Implication and novel roles of classical protein kinase C. *J Immunol* 183, 2104-2114 (2009).
47. Scott, J. D. Cyclic nucleotide-dependent protein kinases. *Pharmacol Ther* 50, 123-145 (1991).
48. Alessi, D. R., Cuenda, A., Cohen, P., Dudley, D. T. & Saltiel, A. R. PD 098059 is a specific inhibitor of the activation of mitogen-activated protein kinase kinase in vitro and in vivo. *J Biol Chem* 270, 27489-27494 (1995).
49. Cuenda, A. et al. SB 203580 is a specific inhibitor of a MAP kinase homologue which is stimulated by cellular stresses and interleukin-1. *FEBS Lett* 364, 229-233 (1995).
50. Lanier, L. L. & Bakker, A. B. The ITAM-bearing transmembrane adaptor DAP12 in lymphoid and myeloid cell function. *Immunol Today* 21, 611-614 (2000).
51. Chen, C. H. et al. Dendritic-cell-associated C-type lectin 2 (DCAL-2) alters dendritic-cell maturation and cytokine production. *Blood* 107, 1459-1467 (2006).
52. Kanazawa, N. et al. DCIR acts as an inhibitory receptor depending on its immunoreceptor tyrosine-based inhibitory motif. *J Invest Dermatol* 118, 261-266 (2002).
53. Barrow, A. D. & Trowsdale, J. You say ITAM and I say ITIM, let's call the whole thing off: the ambiguity of immunoreceptor signalling. *Eur J Immunol* 36, 1646-1653 (2006).
54. Hamerman, J. A. & Lanier, L. L. Inhibition of immune responses by ITAM-bearing receptors. *Sci STKE* 2006, re1 (2006).
55. O'Brien, C. D., Cao, G., Makrigiannakis, A. & DeLisser, H. M. Role of immunoreceptor tyrosine-based inhibitory motifs of PECAM-1 in PECAM-1-dependent cell migration. *Am J Physiol Cell Physiol* 287, C1103-1113 (2004).
56. Walter, R. B. et al. ITIM-dependent endocytosis of CD33-related Siglecs: role of intracellular domain, tyrosine phosphorylation, and the tyrosine phosphatases, Shp1 and Shp2. *J Leukoc Biol* 83, 200-211 (2008).
57. Ryan, E. J. et al. Dendritic cell-associated lectin-1: a novel dendritic cell-associated, C-type lectin-like molecule enhances T cell secretion of IL-4. *J Immunol* 169, 5638-5648 (2002).
58. Jones, M. L., Craik, J. D., Gibbins, J. M. & Poole, A. W. Regulation of SHP-1 tyrosine phosphatase in human platelets by serine phosphorylation at its C terminus. *J Biol Chem* 279, 40475-40483 (2004).
59. Krotz, F. et al. The tyrosine phosphatase, SHP-1, is a negative regulator of endothelial superoxide formation. *J Am Coil Cardiol* 45, 1700-1706 (2005).
60. Mannell, H. et al. Inhibition of the tyrosine phosphatase SHP-2 suppresses angiogenesis in vitro and in vivo. *J Vasc Res* 45, 153-163 (2008).
61. Chen, C. C., Wang, J. K. & Lin, S. B. Antisense oligonucleotides targeting protein kinase C-alpha, -beta I, or -delta but not -eta inhibit lipopolysaccharide-induced nitric oxide synthase expression in RAW 264.7 macrophages:

involvement of a nuclear factor kappa B-dependent mechanism. *J Immunol* 161, 6206-6214 (1998).
62. Sale, G., Sale, E., Hodgkinson, C. & Jones, N. P.
63. Berrou, E. & Bryckaert, M. Platelet-derived growth factor inhibits smooth muscle cell adhesion to fibronectin by ERK-dependent and ERK-independent pathways. *J Biol Chem* 276, 39303-39309 (2001).
64. Wei, S. et al. Critical role of Lyn kinase in inhibition of neutrophil apoptosis by granulocyte-macrophage colony-stimulating factor. *J Immunol* 157, 5155-5162 (1996).
65. Li, Y. & Chen, B. Differential regulation of fyn-associated protein tyrosine kinase activity by macrophage colony-stimulating factor (M-CSF) and granulocyte-macrophage colony-stimulating factor (GM-CSF). *J Leukoc Biol* 57, 484-490 (1995).
66. Wang, X., Wu, H. & Miller, A. H. Interleukin 1alpha (IL-1alpha) induced activation of p38 mitogen-activated protein kinase inhibits glucocorticoid receptor function. *Mol Psychiatry* 9, 65-75 (2004).
67. Manabe, N. et al. Src transduces signaling via growth hormone (GH)-activated GH receptor (GHR) tyrosine-phosphorylating GHR and STAT5 in human leukemia cells. *Leuk Res* 30, 1391-1398 (2006).
68. Eklow C, Makrygiannakis D, Backdahl L, Padyukov L, Ulfgren A K, et al. (2008) Cellular distribution of the C-type II lectin dendritic cell immunoreceptor (DCIR) and its expression in the rheumatic joint: identification of a subpopulation of DCIR+ T cells. Ann Rheum Dis 67: 1742-1749.
69. Boasso A, Shearer G M (2008) Chronic innate immune activation as a cause of HIV-1 immunopathogenesis. Clin Immunol 126: 235-242
70. Arnoult D, Petit F, Lelievre J D, Estaquier J (2003) Mitochondria in HIV-1-induced apoptosis. Biochem Biophys Res Commun 304: 561-574
71. Andrew K. Sewell D A P, Annette Oxenius, Anthony D. Kelleher, Rodney E. Phillips, (2000) Cytotoxic T Lymphocyte Responses to Human Immunodeficiency Virus: Control and Escape. Stem Cells 18: 230-244
72. Heinkelein M, Sopper S, Jassoy C (1995) Contact of human immunodeficiency virus type 1-infected and uninfected CD4+ T lymphocytes is highly cytolytic for both cells. J Virol 69: 6925-6931.
73. Gougeon M L, Lecoeur H, Dulioust A, Enouf M G, Crouvoiser M, et al. (1996) Programmed cell death in peripheral lymphocytes from HIV-infected persons: increased susceptibility to apoptosis of CD4 and CD8 T cells correlates with lymphocyte activation and with disease progression. J Immunol 156: 3509-3520.
74. Sousa A E, Carneiro J, Meier-Schellersheim M, Grossman Z, Victorino R M (2002) CD4 T cell depletion is linked directly to immune activation in the pathogenesis of HIV-1 and HIV-2 but only indirectly to the viral load. J Immunol 169: 3400-3406.
75. Raff M C (1992) Social controls on cell survival and cell death. Nature 356: 397-400.
76. Movassagh M, Foo R S (2008) Simplified apoptotic cascades. Heart Fail Rev 13: 111-119.
77. Susin S A, Lorenzo H K, Zamzami N, Marzo I, Snow B E, et al. (1999) Molecular characterization of mitochondrial apoptosis-inducing factor. Nature 397: 441-446.
78. Finkel T H, Tudor-Williams G, Banda N K, Cotton M F, Curiel T, et al. (1995) Apoptosis occurs predominantly in bystander cells and not in productively infected cells of HIV- and SIV-infected lymph nodes. Nat Med 1: 129-134.
79. Gougeon M L (2005) To kill or be killed: how HIV exhausts the immune system. Cell Death Differ 12: 845-854.
80. Genini D, Sheeter D, Rought S, Zaunders J J, Susin S A, et al. (2001) HIV induces lymphocyte apoptosis by a p53-initiated, mitochondrial-mediated mechanism. FASEB J 15: 5-6.
81. Ameisen J C (2001) Apoptosis subversion: HIV-Nef provides both armor and sword. Nat Med 7: 1181-1182.<
82. Nardelli B, Gonzalez C J, Schechter M, Valentine F T (1995) CD4+ blood lymphocytes are rapidly killed in vitro by contact with autologous human immunodeficiency virus-infected cells. Proc Natl Acad Sci USA 92: 7312-7316.
83. Nie Z, Bren G D, Vlahakis S R, Schimnich A A, Brenchley J M, et al. (2007) Human immunodeficiency virus type 1 protease cleaves procaspase 8 in vivo. J Virol 81: 6947-6956.
84. Moon H S, Yang J S (2006) Role of HIV Vpr as a regulator of apoptosis and an effector on bystander cells. Mol Cells 21: 7-20.
85. Castedo M, Perfettini J L, Andreau K, Roumier T, Piacentini M, et al. (2003) Mitochondrial apoptosis induced by the HIV-1 envelope. Ann N Y Acad Sci 1010: 19-28.
86. Beaulieu S, Kessous A, Landry D, Montplaisir S, Bergeron D, et al. (1996) In vitro characterization of purified human thymic dendritic cells infected with human immunodeficiency virus type 1. Virology 222: 214-226.
87. Azad A A (2000) Could Nef and Vpr proteins contribute to disease progression by promoting depletion of bystander cells and prolonged survival of HIV-infected cells? Biochem Biophys Res Commun 267: 677-685.
88. Roshal M, Zhu Y, Planelles V (2001) Apoptosis in AIDS. Apoptosis 6: 103-116.
89. Imbeault M, Lodge R, Ouellet M, Tremblay M J (2009) Efficient magnetic bead-based separation of HIV-1-infected cells using an improved reporter virus system reveals that p53 up-regulation occurs exclusively in the virus-expressing cell population. Virology 393: 160-167.
90. Cotton M F, Cassella C, Rapaport E L, Tseng P O, Marschner S, et al. (1996) Apoptosis in HIV-1 Infection. Behring Inst Mitt: 220-231.
91. Mehandru S, Poles M A, Tenner-Racz K, Horowitz A, Hurley A, et al. (2004) Primary HIV-1 infection is associated with preferential depletion of CD4+ T lymphocytes from effector sites in the gastrointestinal tract. J Exp Med 200: 761-770.
92. Varbanov M, Espert L, Biard-Piechaczyk M (2006) Mechanisms of CD4 T-cell depletion triggered by HIV-1 viral proteins. AIDS Rev 8: 221-236.
93. Pozarowski P, Huang X, Halicka D H, Lee B, Johnson G, et al. (2003) Interactions of fluorochrome-labeled caspase inhibitors with apoptotic cells: a caution in data interpretation. Cytometry A 55: 50-60.
94. Slee E A, Zhu H, Chow S C, MacFarlane M, Nicholson D W, et al. (1996) Benzyloxycarbonyl-Val-Ala-Asp (OMe) fluoromethylketone (Z-VAD.FMK) inhibits apoptosis by blocking the processing of CPP32. Biochem J 315 (Pt 1): 21-24.
95. Roumier T, Vieira H L, Castedo M, Ferri K F, Boya P, et al. (2002) The C-terminal moiety of HIV-1 Vpr induces cell death via a caspase-independent mitochondrial pathway. Cell Death Differ 9: 1212-1219.
96. Rabaud C, Tronel H, Fremont S, May T, Canton P, et al. (1997) [Free radicals and HIV infection]. Ann Biol Clin (Paris) 55: 565-571.

97. Pyo C W, Yang Y L, Yoo N K, Choi S Y (2008) Reactive oxygen species activate HIV long terminal repeat via post-translational control of NF-kappaB. Biochem Biophys Res Commun 376: 180-185.
98. Bertrand R, Solary E, O'Connor P, Kohn K W, Pommier Y (1994) Induction of a Common Pathway of Apoptosis by Staurosporine. Experimental Cell Research 211: 314-321.
99. Gupta S, Young T, Yel L, Su H, Gollapudi S (2007) Differential sensitivity of naive and subsets of memory CD4+ and CD8+ T cells to hydrogen peroxide-induced apoptosis. Genes Immun 8: 560-569.
100. Matsura T, Kai M, Fujii Y, Ito H, Yamada K (1999) Hydrogen peroxide-induced apoptosis in HL-60 cells requires caspase-3 activation. Free Radic Res 30: 73-83.
101. Cossarizza A (2008) Apoptosis and HIV infection: about molecules and genes. Curr Pharm Des 14: 237-244.
102. Stephensen C B, Marquis G S, Douglas S D, Wilson C M (2005) Plasma cytokines and oxidative damage in HIV-positive and HIV-negative adolescents and young adults: a protective role for IL-10? Free Radic Res 39: 859-864.
103. Suresh D R, Annam V, Pratibha K, Prasad B V (2009) Total antioxidant capacity—a novel early bio-chemical marker of oxidative stress in HIV infected individuals. J Biomed Sci 16: 61.
104. Dobmeyer T S, Findhammer S, Dobmeyer J M, Klein S A, Raffel B, et al. (1997) Ex vivo induction of apoptosis in lymphocytes is mediated by oxidative stress: role for lymphocyte loss in HIV infection. Free Radic Biol Med 22: 775-785.
105. Sloand E M, Young N S, Kumar P, Weichold F F, Sato T, et al. (1997) Role of Fas Ligand and Receptor in the Mechanism of T-Cell Depletion in Acquired Immunodeficiency Syndrome Effect on CD4+ Lymphocyte Depletion and Human Immunodeficiency Virus Replication. Blood 89: 1357-1363.
106. Petit F, Arnoult D, Viollet L, Estaquier J (2003) Intrinsic and extrinsic pathways signaling during HIV-1 mediated cell death. Biochimie 85: 795-811.
107. Li C J, Friedman D J, Wang C, Metelev V, Pardee A B (1995) Induction of apoptosis in uninfected lymphocytes by HIV-1 Tat protein. Science 268: 429-431.
108. Levy D N, Refaeli Y, MacGregor R R, Weiner D B (1994) Serum Vpr regulates productive infection and latency of human immunodeficiency virus type 1. Proc Natl Acad Sci USA 91: 10873-10877.
109. Levy D N, Refaeli Y, Weiner D B (1995) Extracellular Vpr protein increases cellular permissiveness to human immunodeficiency virus replication and reactivates virus from latency. J Virol 69: 1243-1252.
110. Lenassi M, Cagney G, Liao M, Vaupotic T, Bartholomeeusen K, et al. (2009) HIV Nef is secreted in exosomes and triggers apoptosis in bystander CD4+ T cells. Traffic 11: 110-122.
111. Gougeon M L (2003) Apoptosis as an HIV strategy to escape immune attack. Nat Rev Immunol 3: 392-404.
112. Shultz L D, Rajan T V, Greiner D L (1997) Severe defects in immunity and hematopoiesis caused by SHP-1 protein-tyrosine-phosphatase deficiency. Trends Biotechnol 15: 302-307.
113. Fortin J F, Barbeau B, Robichaud G A, Pare M E, Lemieux A M, et al. (2001) Regulation of nuclear factor of activated T cells by phosphotyrosyl-specific phosphatase activity: a positive effect on HIV-1 long terminal repeat-driven transcription and a possible implication of SHP-1. Blood 97: 2390-2400.
114. Zhang J, Somani A K, Watt S, Mills G B, Siminovitch K A (1999) The Src-homology domain 2-bearing protein tyrosine phosphatase-1 inhibits antigen receptor-induced apoptosis of activated peripheral T cells. J Immunol 162: 6359-6367.
115. Lima R G, Van Weyenbergh J, Saraiva E M, Barral-Netto M, Galvao-Castro B, et al. (2002) The replication of human immunodeficiency virus type 1 in macrophages is enhanced after phagocytosis of apoptotic cells. J Infect Dis 185: 1561-1566.
116. Savill J, Dransfield I, Gregory C, Haslett C (2002) A blast from the past: clearance of apoptotic cells regulates immune responses. Nat Rev Immunol 2: 965-975.
117. Mantovani A, Sica A, Allavena P, Garlanda C, Locati M (2009) Tumor-associated macrophages and the related myeloid-derived suppressor cells as a paradigm of the diversity of macrophage activation. Hum Immunol 70: 325-330.

Headings are included herein for reference and to aid in locating certain sections. These headings are not intended to limit the scope of the concepts described therein under, and these concepts may be applicable in other sections throughout the entire specification. Thus, the present invention is not intended to be limited to the embodiments shown herein but is to be accorded the widest scope consistent with the principles and novel features disclosed herein.

Unless otherwise indicated, all numbers expressing quantities of ingredients, reaction conditions, concentrations, properties, and so forth used in the specification and claims are to be understood as being modified in all instances by the term "about". At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

It is understood that the examples and embodiments described herein are for illustrative purposes only and that various modifications or changes in light thereof will be suggested to persons skilled in the art and are to be included within the present invention and scope of the appended claims.

The invention claimed is:

1. A method for the treatment of a human immunodeficiency virus (HIV) infection, the method comprising administering to a subject in need thereof a compound consisting of a polypeptide, or a mixture of polypeptides, comprising an amino acid sequence as set forth in SEQ ID NO.2:

Xaa$_1$Xaa$_2$Xaa$_3$Xaa$_4$Xaa$_5$Xaa$_6$    (SEQ ID NO.: 2)

wherein
Xaa$_1$ is S, I, V or L;
Xaa$_2$ is any amino acid or phospho-threonine;
Xaa$_3$ is tyrosine or phospho-tyrosine;
Xaa$_4$ or Xaa$_5$ is any amino acid;
Xaa$_6$ is I, V or L;
at least one of Xaa$_2$ or Xaa$_3$ is a phosphorylated residue;
wherein said polypeptide is other than SEQ ID NO: 1, 60, 61, or 62.

2. The method of claim 1, wherein said compound consists of a polypeptide, or a mixture of polypeptides, comprising an amino acid sequence as set forth in SEQ ID NO.15:

ITYAEV    (SEQ ID NO.: 15)

wherein at least one of the threonine (T) or tyrosine (Y) residue is phosphorylated.

3. The method of claim 1, wherein said compound consists of a polypeptide, or a mixture of polypeptides, selected from the group consisting of:
(i) EITYAEVRFKNEFKS (SEQ ID NO: 12), wherein the threonine is phosphorylated;
(ii) EITYAEVRFKNES (SEQ ID NO: 11), wherein the tyrosine is phosphorylated;
(iii) ITYAEV (SEQ ID NO: 16), wherein the tyrosine is phosphorylated;
(iv) ITYAEV (SEQ ID NO: 17), wherein the threonine is phosphorylated;

(v) VAYETI (SEQ ID NO: 18), wherein the tyrosine is phosphorylated;
(vi) VAYETI (SEQ ID NO: 19), wherein the threonine is phosphorylated;
(vii) EITYAEVRFKN (SEQ ID NO: 21), wherein the tyrosine is phosphorylated;
(viii) EITYAEVRFKN(SEQ ID NO: 22), wherein the threonine is phosphorylated;
(ix) VAYETIKNFR (SEQ ID NO: 23), wherein the tyrosine is phosphorylated;
(x) VAYETIKNFR (SEQ ID NO: 24), wherein the threonine is phosphorylated;
(xi) EITYAEVRFKNEFKS (SEQ ID NO: 26), wherein the tyrosine is phosphorylated;
(xii) EITYAEVRFKNEFKS (SEQ ID NO: 27), wherein the threonine is phosphorylated;
(xiii) KENFKRFVAY (PO$_3$H$_2$)ETIES (SEQ ID NO: 28), wherein the tyrosine is phosphorylated; and
(xiv) KENFKRFVAYETIES (SEQ ID NO: 29) wherein the threonine is phosphorylated.

4. A method for the treatment of a virus infection, the method comprising administering to a subject in need thereof a polypeptide, or a mixture of polypeptides, comprising an amino acid sequence as set forth in SEQ ID NO.2:

```
Xaa₁Xaa₂Xaa₃Xaa₄Xaa₅Xaa₆        (SEQ ID NO.: 2)
``` wherein
Xaa$_1$ is S, I, V or L;
Xaa$_2$ is any amino acid or phospho-threonine;
Xaa$_3$ is tyrosine or phospho-tyrosine;
Xaa$_4$ or Xaa$_5$ is any amino acid;
Xaa$_6$ is I, V or L;
at least one of Xaa$_2$ or Xaa$_3$ is a phosphorylated residue;
wherein said polypeptide is other than SEQ ID NO: 1, 60, 61, or 62.

5. The method of claim 4, wherein said polypeptide or mixture of polypeptides, comprises an amino acid sequence as set forth in SEQ ID NO.15:

```
ITYAEV            (SEQ ID NO.: 15)
``` wherein at least one of the threonine (T) or tyrosine (Y) residue is phosphorylated.

6. The method of claim 4, wherein said polypeptide or mixture of polypeptides, comprises a polypeptide selected from the group consisting of:
(i) EITYAEVRFKNEFKS (SEQ ID NO: 12), wherein the threonine is phosphorylated;
(ii) EITYAEVRFKNES (SEQ ID NO: 11), wherein the tyrosine is phosphorylated;
(iii) ITYAEV (SEQ ID NO: 16), wherein the tyrosine is phosphorylated;
(iv) ITYAEV (SEQ ID NO: 17), wherein the threonine is phosphorylated;
(v) VAYETI (SEQ ID NO: 18), wherein the tyrosine is phosphorylated;
(vi) VAYETI (SEQ ID NO: 19), wherein the threonine is phosphorylated;
(vii) EITYAEVRFKN (SEQ ID NO: 21), wherein the tyrosine is phosphorylated;
(viii) EITYAEVRFKN(SEQ ID NO: 22), wherein the threonine is phosphorylated;
(ix) VAYETIKNFR (SEQ ID NO: 23), wherein the tyrosine is phosphorylated;
(x) VAYETIKNFR (SEQ ID NO: 24), wherein the threonine is phosphorylated;
(xi) EITYAEVRFKNEFKS (SEQ ID NO: 26), wherein the tyrosine is phosphorylated;
(xii) EITYAEVRFKNEFKS (SEQ ID NO: 27), wherein the threonine is phosphorylated;
(xiii) KENFKRFVAY (PO$_3$H$_2$)ETIES (SEQ ID NO: 28), wherein the tyrosine is phosphorylated; and
(xiv) KENFKRFVAYETIES (SEQ ID NO: 29) wherein the threonine is phosphorylated.

7. The method of claim 4, wherein the virus is an immunodeficiency virus.

8. The method of claim 4, wherein the virus is selected from the group consisting of human HIV, feline FIV, bovine BIV, equine infectious anemia virus (EIAV), murine leukemia virus (MLV)), hepatitis C virus, and herpes viruses.

9. The method of claim 4, wherein the virus is a human immunodeficiency virus (HIV).

10. A method for the treatment of a human immunodeficiency virus (HIV) infection, the method comprising administering to a subject in need thereof a polypeptide, or a mixture of polypeptides, comprising an amino acid sequence as set forth in as set forth in SEQ ID NO.15:

```
ITYAEV            (SEQ ID NO.: 15)
``` wherein at least one of the threonine (T) or tyrosine (Y) residue is phosphorylated;
wherein said polypeptide is other than SEQ ID NO: 1, 60, 61, or 62.

11. The method of claim 1, wherein said polypeptide is linked to a moiety or compound enhancing cellular uptake of the polypeptide by a cell.

12. The method of claim 1, wherein said polypeptide is formulated with a vehicle enhancing cellular uptake of the polypeptide by a cell.

13. The method of claim 4, wherein said polypeptide is linked to a moiety or compound enhancing cellular uptake of the polypeptide by a cell.

14. The method of claim 4, wherein said polypeptide is formulated with a vehicle enhancing cellular uptake of the polypeptide by a cell.

15. The method of claim 10, wherein said polypeptide is linked to a moiety or compound enhancing cellular uptake of the polypeptide by a cell.

16. The method of claim 10, wherein said polypeptide is formulated with a vehicle enhancing cellular uptake of the polypeptide by a cell.

17. A method for inhibiting human immunodeficiency virus (HIV) cell infection, comprising inserting into a cell expressing dendritic cell immunoreceptor (DCIR) a polypeptide, or a mixture of polypeptides comprising an amino acid sequence as set forth in SEQ ID NO.2:

```
                                  (SEQ ID NO.: 2)
Xaa₁Xaa₂Xaa₃Xaa₄Xaa₅Xaa₆
``` wherein
Xaa$_1$ is S, I, V or L;
Xaa$_2$ is any amino acid or phospho-threonine;
Xaa$_3$ is tyrosine or phospho-tyrosine;
Xaa$_4$ or Xaa$_5$ is any amino acid;
Xaa$_6$ is I, V or L;
at least one of Xaa$_2$ or Xaa$_3$ is a phosphorylated residue;
wherein said polypeptide is other than SEQ ID NO: 1, 60, 61, or 62.

* * * * *